US011666288B2

United States Patent
Abrol et al.

(10) Patent No.: US 11,666,288 B2
(45) Date of Patent: Jun. 6, 2023

(54) SYSTEMS AND METHODS FOR GRAPHICAL USER INTERFACES FOR MEDICAL DEVICE TRENDS

(71) Applicant: GE Precision Healthcare LLC, Milwaukee, WI (US)

(72) Inventors: Sidharth Abrol, Bangalore (IN); John Page, Verona, WI (US); Sohan Rashmi Ranjan, Bangalore (IN); Abhijit Patil, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 56 days.

(21) Appl. No.: 16/802,366

(22) Filed: Feb. 26, 2020

(65) Prior Publication Data

US 2021/0059616 A1 Mar. 4, 2021

Related U.S. Application Data

(63) Continuation-in-part of application No. 16/557,943, filed on Aug. 30, 2019.

(51) Int. Cl.
*G06F 3/00* (2006.01)
*A61B 5/00* (2006.01)
(Continued)

(52) U.S. Cl.
CPC .......... *A61B 5/7435* (2013.01); *A61B 5/7275* (2013.01); *G16H 40/67* (2018.01); *G16H 50/30* (2018.01); *G06F 3/0482* (2013.01)

(58) Field of Classification Search
CPC .... A61B 5/7435; A61B 5/7275; G16H 40/67; G16H 50/30; G16H 20/17; G06F 3/0482;
(Continued)

(56) References Cited

U.S. PATENT DOCUMENTS 8,620,418 B1 * 12/2013 Kuppuraj ............. A61B 5/0006
600/523
8,690,771 B2 4/2014 Wekell et al.
(Continued)

OTHER PUBLICATIONS

Page, J., "Systems and Methods for Graphical User Interfaces for Supervisory Application," U.S. Appl. No. 16/557,919, filed Aug. 30, 2019, 119 pages.
(Continued)

*Primary Examiner* — Tadesse Hailu
*Assistant Examiner* — Andrew Chung

(57) ABSTRACT

Systems and methods are provided for perioperative care in a medical facility. In an example, a system includes a display and a computing device operably coupled to the display and storing instructions executable to output, to the display, a graphical user interface (GUI) that includes real-time medical device data of a patient, at least some of the real-time medical device data displayed via the GUI as a plurality of patient monitoring parameter tiles, the GUI including a risk score indicative of a relative likelihood that the patient will exhibit a condition within a period of time, and responsive to a user input, display, on the GUI, a set of trend lines each showing values for a respective patient monitoring parameter over a time range, each trend line of the set of trend lines selected based on a contribution of each respective patient monitoring parameter to the risk score.

16 Claims, 34 Drawing Sheets

(51) Int. Cl.
*G16H 40/67* (2018.01)
*G16H 50/30* (2018.01)
*G06F 3/0482* (2013.01)

(58) Field of Classification Search
CPC .... G06F 3/04847; G06F 9/451; A61M 16/01; A61M 2205/18; A61M 2205/3303; A61M 2205/505
See application file for complete search history.

(56) References Cited

U.S. PATENT DOCUMENTS

| | | | | |
|---|---|---|---|---|
| 9,131,881 | B2* | 9/2015 | Diab | A61B 5/7405 |
| 9,778,079 | B1* | 10/2017 | Al-Ali | G01D 7/02 |
| 9,946,840 | B1* | 4/2018 | Kemp | G16H 10/60 |
| 2010/0100848 | A1* | 4/2010 | Ananian | G06F 3/0482 |
| | | | | 715/834 |
| 2013/0246950 | A1* | 9/2013 | Freestone | G06F 16/958 |
| | | | | 715/765 |
| 2013/0265327 | A1* | 10/2013 | Vann | G06F 40/106 |
| | | | | 345/629 |
| 2014/0012117 | A1* | 1/2014 | Mensinger | A61B 5/742 |
| | | | | 600/365 |
| 2014/0184422 | A1* | 7/2014 | Mensinger | A61B 5/742 |
| | | | | 340/870.02 |
| 2014/0222400 | A1* | 8/2014 | Coleman | G16C 20/30 |
| | | | | 703/2 |
| 2015/0145691 | A1* | 5/2015 | Eshelman | G16H 10/40 |
| | | | | 340/870.07 |
| 2016/0345874 | A1* | 12/2016 | Raisoni | A61M 5/1723 |
| 2017/0000412 | A1 | 1/2017 | Scott | |
| 2017/0181694 | A1* | 6/2017 | Niklewski | A61M 5/1723 |
| 2017/0235910 | A1* | 8/2017 | Cantillon | G16H 40/63 |
| | | | | 705/2 |
| 2018/0046637 | A1* | 2/2018 | Koopman | G06F 16/958 |
| 2018/0082036 | A1 | 3/2018 | Hanrahan et al. | |
| 2018/0193579 | A1 | 7/2018 | Hanrahan et al. | |
| 2018/0228408 | A1* | 8/2018 | Raisoni | A61B 5/7435 |
| 2018/0267700 | A1* | 9/2018 | Kaditz | G16H 50/20 |
| 2018/0310822 | A1* | 11/2018 | Indorf | A61B 5/02438 |
| 2019/0320988 | A1* | 10/2019 | Ahmed | A61B 5/002 |
| 2020/0000396 | A1* | 1/2020 | Madabhushi | A61B 5/7267 |
| 2020/0005900 | A1* | 1/2020 | Cha | G16H 50/30 |
| 2020/0090485 | A1* | 3/2020 | Casse | G16H 20/40 |
| 2020/0168338 | A1* | 5/2020 | Forsberg | G06N 5/04 |
| 2020/0242566 | A1* | 7/2020 | Agarwal | G06Q 10/1095 |
| 2021/0005321 | A1* | 1/2021 | Hwang | G16H 50/20 |

OTHER PUBLICATIONS

Page, J., "Systems and Methods for Medical Device Monitoring," U.S. Appl. No. 16/557,930, filed Aug. 30, 2019, 120 pages.
International Bureau of WIPO, International Preliminary Report on Patentability Issued in Application No. PCT/US2020/047934, dated Mar. 1, 2022, WIPO, 7 pages.

* cited by examiner

SYSTEMS AND METHODS FOR GRAPHICAL USER INTERFACES FOR MEDICAL DEVICE TRENDS

RELATED APPLICATIONS

The present application is a continuation-in-part of U.S. patent application Ser. No. 16/557,943, entitled "SYSTEMS AND METHODS FOR GRAPHICAL USER INTERFACES FOR MEDICAL DEVICE TRENDS" and filed Aug. 30, 2019. The entire contents of the above-referenced application are hereby incorporated by reference for all purposes.

FIELD

Embodiments of the subject matter disclosed herein relate to patient monitoring during perioperative care, and more specifically to graphical user interfaces for medical device predictive functions.

BACKGROUND

Certain medical procedures, such as surgery, may require various sub-procedures to be performed to prep the patient for surgery, maintain the patient in a certain condition during surgery (e.g., anesthetized), and help the patient recover after surgery. Such sub-procedures that are performed in support of a main procedure may be referred to as perioperative care. Perioperative care of patients in a hospital or other medical facility may include multiple patient monitoring devices monitoring multiple patients. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources. Additionally, the presentation of patient medical information to the care providers may require multiple time-consuming and cumbersome requests or searches for information.

BRIEF DESCRIPTION

In one embodiment, a system includes a display and a computing device operably coupled to the display and storing instructions executable to output, to the display, a graphical user interface (GUI) that includes real-time medical device data determined from output of one or more medical devices each monitoring a patient, and where at least some of the real-time medical device data displayed via the GUI is displayed as a plurality of patient monitoring parameter tiles, the GUI further including a predictive tile including a risk score indicative of a relative likelihood that the patient will exhibit a specified condition within a predetermined period of time, and responsive to a user input, display, on the GUI, a set of trend lines each showing values for a respective patient monitoring parameter over a time range, each trend line of the set of trend lines selected based on a contribution of each respective patient monitoring parameter to the risk score.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
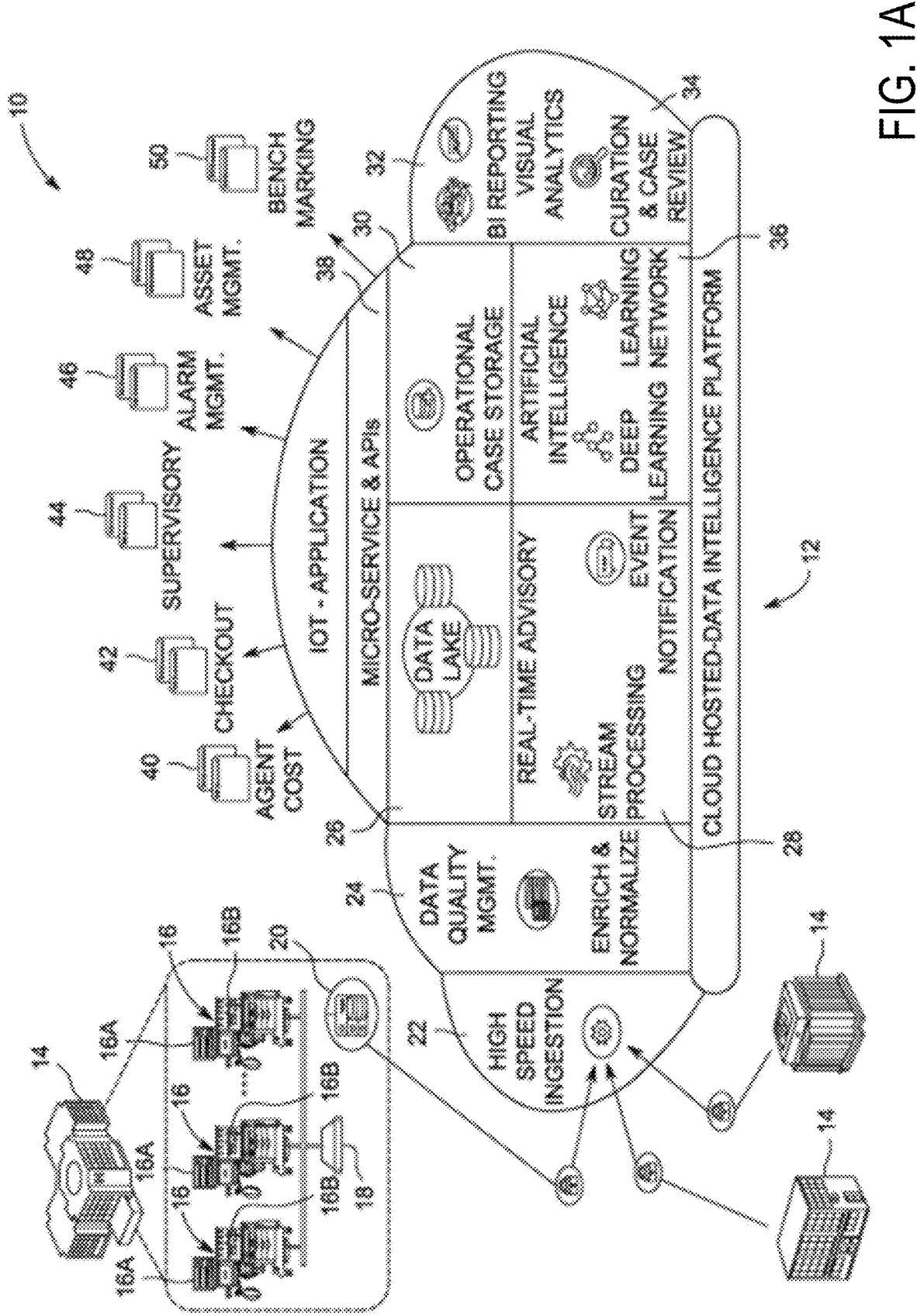
FIGS. 1A and 1B schematically show an example system for perioperative care and supervision including a supervisory application.

Embodiments of systems and methods as disclosed herein operate to facilitate perioperative care for a plurality of patients, and supervision of a plurality of care providers attending to the plurality of patients. To facilitate the perioperative care and supervision described herein, the systems and methods as disclosed herein collect and process a wide variety of medical device data. Medical device data includes physiological data (also referred to as patient monitoring data) that is acquired from a patient by a medical device and machine data collected internally from the medical device itself. Machine data may include alarms, device status, settings, messages, and measured operational data. Machine data may further include settings and values that represent specific actions taken with the medical device for example, in response to automated controls or due to clinician inputs. For example, in an anesthesia delivery machine, this may include changes to oxygen and/or anesthetic agent concentrations. The machine data may further include clinical and/or technical alarms initiated by the medical device or device diagnostic information. Still further examples of the machine data include proactive or predictive service alerts from the medical device, maintenance checkout information, and/or processor clock cycle signals or power signals or other operational signals from various components of the medical device indicative that the medical device is turned on, in use, in operation, held in a stand by condition, or turned off.

The medical device data can be collected in time series format as provided from the medical devices themselves. As used herein, the time series format of the medical device data can include waveforms, binary data, numeric data, and/or textual data in a time series format. Embodiments of the systems and methods as disclosed herein receive the medical device data from the medical devices at a frequency similar to the frequency at which it is produced by the medical device. In embodiments, this increased velocity of the received data and the monitoring and analysis of medical device machine data can enable improved monitoring systems and methods as disclosed herein. As described in further detail herein, embodiments of systems and methods support high speed data ingestion, enrichment, normalization, and data curation of the medical device data. The medical device data can undergo real time analysis and further enrichment of the data with event detection and notation. While all of the medical device data can be saved for retrospective and automated machine learning and analysis, event detection and notation can be used to create further exemplary files of medical device data stemming from particular events or conditions which can be used as exemplary or case study data for further analysis.

The medical device data may be supplied to one or more care providers, such as a supervising anesthesiologist, nurse anesthesiologists, and other care providers. In particular, the medical device data may be supplied to the supervising anesthesiologist or other supervising care provider via a supervisory application that facilitates presentation of the medical device data in real-time or near real-time via one or more graphical user interfaces that may be displayed on a device of the supervising care provider, such as a mobile device (e.g., smart phone, tablet, wearable). The supervisory application may facilitate display of medical device data, including physiological data and medical device setting/parameter data, for a plurality of patients and for a plurality of different patient monitoring parameters to the supervising care provider. The displayed medical device data for the plurality of patients may be displayed simultaneously in a multi-patient graphical user interface (GUI), which may allow the supervising care provider to easily monitor patient status for each patient, even if the care provider is located away from the patient(s). When additional information for a specific patient is desired, the supervisory application may generate a single-patient GUI that provides more detailed medical device data for the patient.

The supervisory application may also monitor patient status, via the medical device data, and may output various notifications, such as alarms, when patient status is predicted to change (e.g., deteriorate), patient status changes, or a specified patient monitoring parameter or combination of parameters (such as blood oxygenation) reaches a predefined condition relative to a threshold (e.g., drops below a threshold) or changes over time. The supervisory application may also facilitate communication between the supervising care provider and one or more subordinate care providers that may be in a room with a patient while the supervising care provider is located in a different room or area of the medical facility. For example, a subordinate care provider may send a request, via an in-room GUI of the supervisory application that is executed on a device of the subordinate care provider, for a consultation from the supervising care provider, which may be received by the supervising care provider's device and output to the supervising care provider via a GUI of the supervisory application. The in-room GUI may also facilitate text or voice messaging between the subordinate care provider and the supervising care provider.

The supervisory application may also generate a trends GUI that may be output on the supervising care provider's device. Via the trends GUI, the supervising care provider may assess, for a plurality of selected patient monitoring parameters, change in medical device data over time. The trend for each selected patient monitoring parameter may be displayed simultaneously in a time-aligned fashion. Further, a relative change in each patient monitoring parameter over a specified time duration may be determined and displayed in response to a single user input.

The various GUIs and functions of the supervisory application described above may allow for a single supervising care provider to simultaneously monitor multiple patients during respective medical procedures, such as surgery. While each patient may be attended to by multiple care providers during the medical procedure, such as one or more surgeons, nurses, medical technicians, etc., certain supervising care providers, such as anesthesiologists, may attend to multiple patients at once and may oversee a plurality of subordinate care providers, such as nurse anesthesiologists. As the number of subordinate care providers increases relative to the number of supervising care providers, and as medical procedures become more complex, the need for a supervising care provider to be able to monitor patients and oversee subordinate care providers remotely has increased. For example, a supervising anesthesiologist may be scheduled to initiate and monitor an induction phase of anesthesia for a patient, which may demand the supervising anesthesiologist be in the operating room with the patient during that time. However, the supervising anesthesiologist may also be attending to six other patients that are in the maintenance phase of anesthesia, with each of the six other patients being monitored by an in-room nurse anesthesiologist. If an event were to occur to one of the six other patients that demanded the care of the supervising anesthesiologist, there may be a delay from when the supervising anesthesiologist is notified of the event to when the supervising anesthesiologist could actually arrive to care for the patient. However, via the supervisory application described herein, the supervising care provider may be able to monitor patient status for all patients from any location, and may be able to adjust medical therapy device settings and/or instruct subordinate care providers from afar. In doing so, patient care may be improved.

The supervisory application may facilitate the display of real-time medical device data obtained and/or determined from a plurality of medical devices monitoring a plurality of patients. The real-time medical device data may be displayed via various graphical user interfaces (GUIs). As an example, a single-patient GUI may be displayed on a care provider device (e.g., mobile phone, tablet, and/or wearable). Via the single-patient GUI, real-time medical device data for a patient may be displayed via a plurality of patient monitoring parameter tiles. The plurality of patient monitoring parameter tiles may be scalable, modular, and customizable by the user and/or by the supervisory application to allow for easy customizability, and ease of adding new patient monitoring parameters/medical device data in the future. For example, a user of the supervisory application (e.g., a care provider such as an anesthesiologist) may create a set of rules or an algorithm (where the rules or algorithm may be referred to as an insight or as a function) that may be executed using the real-time medical device data to determine a result (e.g., a determination of procedure phase, a prediction of patient state, a recommended course of action, etc.) or a notification of patient status. When the user selects to apply the insight, the result of the insight may be displayed as a tile on the patient-specific GUI going forward, and the other patient monitoring parameter tiles on the patient-specific GUI may be adjusted (e.g., moved, resized, scaled, and so forth) to accommodate the new insight result tile. For example, an insight may include a predictive function that utilizes the medical device data for a patient as inputs and determines a likelihood (referred to as a risk score) that the patient will exhibit a given condition (e.g., hypoxia) within a certain time window. The risk score may be displayed as part of a predictive tile on the patient-specific GUI. As another example, the user may select to include a real time video feed from the patient's room as a tile in the single-patient GUI (larger variety), which may require a relatively large sized tile. The remaining tiles may be rearranged (whether automatically or in response to the user) to accommodate the larger tile.

Figure 1B:
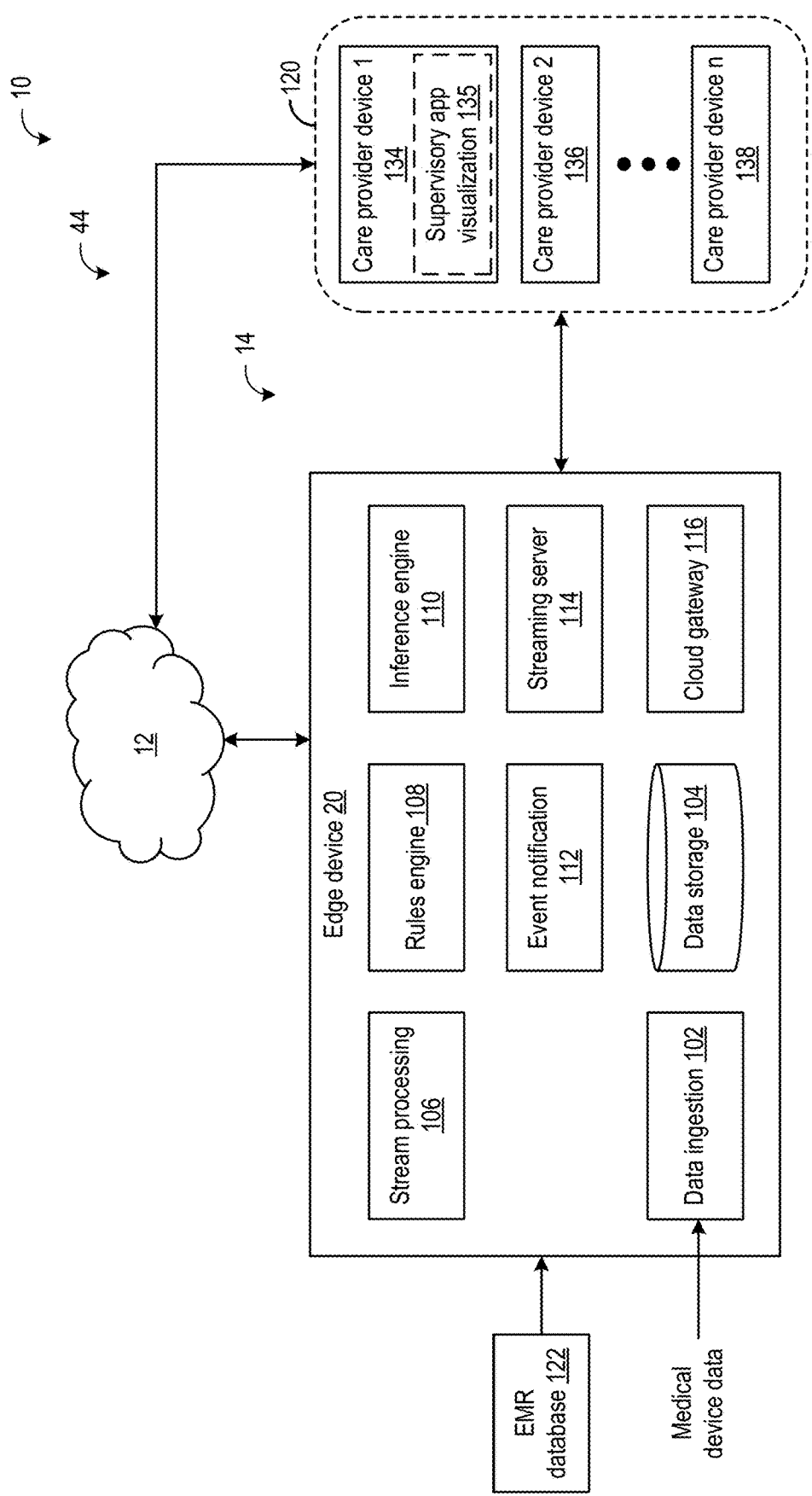

FIGS. 1A and 1B depict an exemplary embodiment of a system 10 for perioperative care and supervision. Referring first to FIG. 1A, system 10 includes a medical device data (MDD) processing system 12. The MDD processing system 12 can be implemented in a variety of hardware and/or software implementations and it should be noted that such implementations are not considered to be limiting. For example, it is contemplated that any or all of the MDD processing system 12 may be embodied exclusively in hardware, exclusively in software, exclusively in firmware or in any combination of hardware, software, and/or firmware. While the following describes exemplary methods and systems, the examples provided herein are not the only way to implement such methods and systems.

In embodiments wherein any of the claims are read to cover an entirely software and/or firmware implementation, in any embodiment, at least one of the elements is hereby expressly defined to include a tangible and non-transient computer readable medium. As used herein, the term tangible computer readable medium is expressly defined to include any type of computer readable storage and to exclude propagating signals. Additionally or alternatively, the example methods and systems may be implemented using coded instruction (e.g., computer readable instructions) stored on a non-transitory computer readable medium such as a flash memory, a read-only memory (ROM) a random-access memory (RAM), a cache, or any other storage media in which information is stored for any duration (e.g. for extended period time periods, permanently, brief instances, for temporarily buffering, and/or for caching of the information). As used herein, the term non-transitory computer readable medium is expressly defined to include any type of computer readable medium and to exclude propagating signals.

In exemplary and non-limiting embodiments of the medical device data processing system 12, the system 12 is implemented by one or more networked processors or computing devices. Processing system 12 may be implemented in a cloud computing platform and/or infrastructure. Memory and processors as referred to herein can be stand-alone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

The MDD processing system 12 is communicatively connected to at least one hospital network 14. Such communicative connections as well as the hospital network itself may include, but are not limited to, a wide area network (WAN); a local area network (LAN); the internet; wired or wireless (e.g. optical, Bluetooth, radio frequency (RF) network; a cloud-based computer infrastructure of computers, routers, servers, gateways, etc.; or any combination thereof associated therewith that allows the system or portions thereof to communicate with one or more computing devices.

The hospital network 14 may exemplarily be a network associated with a portion of a hospital, for example a surgery unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments, while individual hospitals or groups of hospitals may use the MDD processing system 12, the MDD processing system 12 may receive and process information from a plurality of hospital networks including those unaffiliated with one another at the same time.

As depicted in FIG. 1A, the hospital network 14 includes a plurality of medical devices 16. The medical devices 16 may include physiological monitoring devices 16a as well as patient therapy devices 16b. Physiological monitoring devices 16a may include, but are not limited to, heart rate monitors, blood pressure oxygenation monitors, respiration monitors, ECG monitors, EEG monitors, or EMG monitors. An exemplary embodiment of an anesthesia delivery machine will be used for discussion purposes as the medical device, and more specifically as the patient therapy device 16*b*, although it will be recognized by a person of ordinary skill in the art that other devices, including but not limited to patient respiratory assistance devices or dialysis machines, may be further non-limiting examples of patient therapy devices. However, it will be recognized that therapy devices may also include capabilities to not only deliver patient therapy, but also to measure physiological parameters of a patient. For example, embodiments of anesthesia delivery machines may include gas analysis modules operable to measure gas concentrations expired by the patient. In some embodiments, imaging devices, including but not limited to X-ray, CT, MRI, and ultrasound devices, may be examples of medical devices 16 as contemplated within the present disclosure. Still further examples of medical devices may include video and/or audio recording devices.

In an exemplary embodiment, a limited version of the MDD processing system 12 as described herein may be implemented locally, for example as an anesthesia delivery management system 18. In such an embodiment, the anesthesia delivery management system 18 may operate to collect medical device data from a plurality of anesthesia delivery machines 16*b* inter alia to monitor anesthesia agent use between anesthesia delivery machines and across procedures performed by the anesthesia delivery machines in an effort to visualize anesthetic agent consumption and use as well as to quantify, monitor, and evaluate trends across all of the anesthesia delivery machines in the hospital or surgical unit.

The medical devices 16 may be communicatively connected to one or more edge devices, such as edge device 20. Edge device 20 may exemplarily be an edge processing device, cloud processing device, or internet gateway. The edge device 20 may include an internet of things (IOT) gateway which facilitates a secure communications link between the medical devices 16 at the hospital network 14 with the servers, processors, and computer readable media implementing the MDD processing system 12. In exemplary embodiments, the edge device 20 may communicate directly with one or more of the medical devices 16, or may communicate with the medical devices 16 through an intermediate network, for example, the anesthesia delivery management system 18 or another medical device data system or network.

The edge device 20 receives the medical device data as time series data for any of the medical device data available from the medical devices. As noted above, the data streams of medical device data (e.g., machine data, monitored patient physiological parameter data) are available in time series format as acquired from the medical devices and may include, but are not limited to time series information of alarms, device status, device settings, messages, and measured data. In embodiments, the medical devices may be equipped with sensors that improve the self-awareness of the medical device, e.g. sensors that monitor the function, inputs and/or outputs of various components of the medical device itself. Many such sensors are already incorporated into medical devices such as to measure compressor speeds and/or cycle times, internal pressures, voltages, clock speeds, or temperatures, or other sensors as will be recognized by a person of ordinary skill in the art or as disclosed in further detail herein.

The edge device 20 encrypts the time series formatted data and the encrypted data is transmitted using wired and/or wireless communication techniques for encrypted data to the server, processors, and data storage carrying out the MDD processing system 12. The edge device 20 continuously transmits de-identified medical device data in time series format over an encrypted communication channel to a high speed data ingestion module 22 of the MDD processing system 12. While the exemplary embodiment described herein may reference de-identified data, it will be recognized that other embodiments may use patient-identified data with appropriate considerations taken for handling patient data. The high speed data ingestion module 22 takes in the real time streams of medical device data. The data ingestion can be performed in an automated fashion and can preprocess the received streams of real time data in the time series for later processing by the MDD processing system 12. The high speed ingestion module 22 can receive concurrent data streams from multiple connected devices across multiple sites at a high incoming velocity, for example at or near the frequency at which medical devices can output data. In exemplary embodiments the high speed ingestion module 22 is scalable to continue to ingest increased bandwidth of medical device data without significant decrease in ingestion speeds.

The high speed ingestion module 22 takes the time series medical device data from the medical devices of one or more hospital networks and formats it for further processing by a data quality management module 24. In exemplary and non-limiting embodiments, the high speed injection module 22 supports open standard such as ASTMF 2761 or integrated clinical environmental (ICE). The data quality management module 24 may normalize, enrich, and tag the data streams without negatively impacting data latency. In a healthcare environment, a variety of healthcare information products and/or systems may be used to provide medical services, collect medical data, conduct medical exams, etc. However, many healthcare information systems operate using various messaging standards (e.g., Health Level 7 International (HL7 V2.x/v3), Clinical Document Architecture/Continuity Of Care Document (CDA/CCD), American Society for Testing Materials (ASTM), Digital Imaging and Communications in Medicine (DICOM), etc.)) and various standards and/or protocols (e.g., cross-enterprise document sharing (XDS.A/B) cross-enterprise document media interchange (XDM) cross-enterprise document reliable interchange (XDR), patient identifier cross-referencing/patient demographics query (PIX/PDQ) patient administration management (PAM), query for existing data (QED), national counsel for prescription drug programs (NCPDP), etc.)) that make system integration and/or communication more difficult. Thus, normalization may include reformatting of medical data to a consistent or compatible format for use within the MDD processing system 12. In an exemplary embodiment, the medical device data may be normalized into the ISO/IEEE 11073-10101 nomenclature and its extensions. In a still further exemplary embodiment, the data quality management module 24 can normalize the streams of incoming time series data by converting units of measure. The data quality management module 24 can further operate to identify and tag various types of medical device data, locations from which the medical device data was received, or time series data streams originating from the same medical device. These tags can be used as further detailed herein to identify and analyze groups of streams of time series data.

In an exemplary embodiment, the data quality management module 24 normalizes the received incoming data by transforming and/or translating the clinical data streamed from the source healthcare system or device into a canonical data model with associated metadata. The processed medical device data is stored in a data lake 26 which is exemplarily implemented in computer readable storage embodying capability to store terabytes of data. The data lake 26 is a long-term computer storage repository that holds large amounts of raw data in a native format until the data is needed. The native format may include the time series data from the medical devices which may be in waveform or binary format, audio data, image data, and/or video data. In embodiments, this can help to facilitate the ingestion of the data that may not be processed in real time but may still be taken in in real time or near real time and instead stored in the data lake until further needed. This may be facilitated by identifying particular data streams and limiting the processing of those data streams, for example by the data quality management module 24, if it is known at that time that such data stream is not being used in real time analysis. In an exemplary embodiment, the data quality management module 24 may not convert the data to a canonical data model but may still attempt to tag, enrich, or index the data to facilitate later retrieval of that data in a standardized way from the data lake 26.

In a still further embodiment, portions of the data that are stored in the data lake 26 may also be additionally stored in a graph database which may be a separate database residing on the same computer readable storage, or may be embodied on separate computer readable storage from the data lake 26. The graph database may receive the data streams of which it is known that the system may analyze trends in that data stream. The graph database may store the streams of data in a time series format in a way that facilitates trending of the data over time and appending the data with events either identified in the data itself, in one or more of the other data streams, or received by the system from an external source. These events may include, but are not limited to, medical device or clinician actions, clinical events, situations, or complications that arise during the medical procedure. The graph database may later be used by a clinician or technician to identify further relationships between trends and the data streams with other analysis as disclosed herein.

At the same time that the data is stored in the data lake 26, the enriched and normalized medical device data may be provided to a stream processing engine 28. The stream processing engine 28 identifies cases and events in the time series streams of medical device data. Identified clinical cases may be stored in an operational case database 30. Clinical cases may exemplarily include surgical and intensive care unit (ICU) cases. The clinical cases may be identified by the medical device used and the timing of the medical data in the time series of the medical device data. For example, a time series of medical device data from an anesthesia delivery machine showing a change in status turning the machine on and followed by changes to device settings and delivery and/or consumption of anesthetic agent all indicate that a clinical case has begun or is ongoing.

As noted above, the streams of time series medical device data originating from the same medical device or from the same location in a hospital may be tagged or otherwise identified as being related. These tags can be used to simultaneously analyze related data streams or combine analysis of related data streams to identify clinical cases. For example, a device status data stream analysis may be combined with a user input data stream, device setting data stream, and operational data streams to identify when the device is used and how it is used in the clinical case. This information may help to distinguish between a maintenance or checkout of the medical device by a technician from the use of the device for clinical case.

The analysis of the data streams of multiple medical devices, particularly those identified as being related or co-located may further be used to identify clinical cases. For example, coordinated or similar actions in data streams of an anesthesia delivery device and a related patient monitoring device, and/or respiratory support device and/or imaging device, etc., may further be used to identify that these devices are being used together for a clinical case. In still further embodiments, the streaming time series medical device data may be combined with information regarding scheduled clinical cases to help to further identify when and how the medical devices are used during clinical cases.

In embodiments, knowledge of a scheduled use of the medical device (e.g. anesthesia delivery machine) can be used to further identify clinical cases in the streams of medical device data. For example, input or received knowledge regarding a type and time of a scheduled procedure may help to identify the start and end of the clinical case in particular streams of medical device machine data. In an embodiment, a known schedule of use for the medical device may help to identify clinical cases from maintenance or calibration actions which may similarly require powering up and at least partial operation of the medical device.

The medical device data associated with the actions by the anesthesia delivery device and/or other medical devices during the identified clinical case may be stored in the operational case database 30. In an example, the identification of the clinical case is stored along with the other time series streams of medical device data from that anesthesia delivery machine as well as time series streams of medical device data from any physiological monitors and/or other medical devices associated with the use of that anesthesia delivery machine. In another exemplary embodiment as described in further detail, a clinical case summary with links or identifiers to the associated time series medical device data stored in the data lake 26 can be created and stored in the operational case database 30.

In an embodiment, prior to storing the clinical cases in the clinical case database 30, the clinical cases may be classified or profiled which is a technique used for data curation. The profiling of the clinical cases may be based upon, in part, the information in the clinical case summary, and as described in further detail herein, may be used to group the clinical cases into groups, for example normal cases, edge cases, and outlier cases. These determinations may be made in view of a comparison between the time series data in the clinical case against normal distributions of the same type of time series machine data in other similar clinical cases. Edge cases may be identified as borderline or ambiguous cases, not clearly defined as either normal or an outlier. In a merely exemplary embodiment, for a particular measured value or occurrence, a distribution of such occurrences may be used to establish normal, edge, and outlier cases. In a merely exemplary embodiment, a normal case may be within a standard deviation of a median value in the normal distribution while edge cases are between one and two standard deviations and outlier cases are greater than two standard deviations from the median. The categorized cases, as explained in further detail herein, for example, identified edge cases may be further investigated to create or improve event detection algorithms, rules for clinical decision support, alert algorithms, and predictive algorithms.

The stream processing engine 28 also identifies events in the time series streams of medical device data, for example in the manners as described in further detail herein and presented in business intelligence and visual analytics tools 32 which exemplarily may be presented on a graphical display communicatively connected to the medical device data processing system 12.

Once clinical cases are stored in the operational case database 30, clinical cases may be reviewed manually by a clinician or technician using a curation and case review tool 34. The curation and case review tool 34 may be presented in a graphical user interface on a graphical display and further provide inputs exemplarily through the graphical user interface for the user or technician to curate or otherwise assess the clinical cases. This can be performed for investigative, educational, and data curation purposes.

The reporting and visual analytics tool 32 can present the detected events in a variety of channels of communication. For example, the detected events may be presented visually through graphical user interfaces and graphical displays. The detected events or notifications of the detected events can also be reported by communication of events/event notifications to wearable or mobile devices and presentation of medical device data and identified events in visual form in reports and/or dashboards presented in a graphical user interface on a graphical display, as will be explained in more detail below.

The results of the streaming analytics and event detection in the time series of medical device data may be provided to an application programming interface (API) 38 for use by application developers to provide monitoring, reporting, and/or control applications based upon the analyzed streams of medical device data. Such applications may operate through a computer operating system, a website browser, or operate on a mobile computing device or wearable computing device. Non-limiting examples of applications that may leverage the analysis of the time series medical device data include, but are not limited to, an anesthetic agent cost dashboard 40, a checkout dashboard 42, a supervisory application 44, an alarm management application 46, an asset management application 48, and a benchmarking application 50.

The agent cost dashboard 40 may present medical device data regarding anesthetic agent use across clinical cases as well as between anesthesia delivery machines within a hospital network or comparatively between hospital networks. By comparatively presenting this information, anesthetic agent use and behavioral changes can be understood and undertaken to promote efficient use of anesthetic agent.

The checkout dashboard 42 may assist in monitoring the inspection and maintenance of the monitored medical devices. Medical device data such as device status and settings, as well as messages and information in machine data, may provide insight into the inspection processes for maintaining medical devices at a hospital network. The checkout dashboard may identify maintenance and/or testing events in the streams of machine data and note these identified testing events against a testing schedule, requirement (e.g., daily), or other criterion.

The supervisory application 44 may be used by attending and/or supervising anesthesiologists to more efficiently manage remote personnel, nurse anesthetists, and/or other care providers simultaneously working across multiple locations or theatres. The alarm management application 46 may report and present medical device data regarding alarm notifications and silences of alarm notifications in order to better understand and adjust alarms to improve signal to noise in alarm events and to reduce alarm fatigue by clinicians. Additional information about the supervisory application 44 is presented below.

The asset management applications 48 may present use, status, maintenance, and/or inspection information regarding medical devices (e.g. anesthesia delivery machines) or consumables used by medical devices, including components that may be frequently replaced, refilled, or refurbished during normal operation of the medical device (e.g. filters, absorbers). The benchmarking application 50 may provide further operational and quality performance across providers and/or organizations or in a comparative manner for example between hospital networks versus averages or between specific locations.

The supervisory application 44 allows for users (e.g., clinicians such as anesthesiologists, nurses, and other care providers) to view ventilator, anesthesia, and vital parameters of a plurality of patients in different locations (e.g., in different operating rooms) on various smart phones, tablets, or other computing devices associated with the users. The supervisory application 44 may include a backend that is hosted on edge device 20 and/or MDD processing system 12 as dockers/micro services and may be rendered on a user's device (such as care provider device 134 shown in FIG. 1B) using a suitable visualization platform.

FIG. 1B schematically shows example devices of system 10 via which supervisory application may be executed, including edge device 20 in communication with a plurality of care provider devices 120 via hospital network 14 and also in communication with MDD processing system 12.

As mentioned above, the edge device 20 receives the medical device data from the medical devices 16. The medical device data received by the edge device 20 may be ingested by a data ingestion module 102, which may be similar to ingestion module 22 of FIG. 1A, and stored in data storage 104. Data storage 104 may be an ephemeral datastore where the received data is stored temporarily rather than persistently. (The received data, such as the medical device data from the medical devices 16, may be sent to the MDD processing system 12 for long-term storage). Further, the received medical device data may be allocated to various micro services on the edge device 20 in order to carry out aspects of supervisory application 44, including a stream processing module 106, a rules engine 108, an inference engine 110, an event notification service 112, a streaming server 114, and a cloud gateway 116.

As explained above, the supervisory application 44 may be used by attending and/or supervising anesthesiologists to manage other care providers, such as nurse anesthesiologists and/or other subordinate care providers. The hospital/medical facility may rely on a relatively high supervision ratio (e.g., 4-10 subordinate care providers for each supervising anesthesiologist), which may increase the need for the supervising anesthesiologists to have high mobility among operating rooms while still overseeing all subordinate care providers and monitoring patient status for all procedures that may be simultaneously ongoing. The supervisory application 44 may facilitate this mobility and management by allowing supervising anesthesiologists to monitor patient status and communicate with subordinate care providers from a remote location. As will be explained in more detail below, the supervisory application 44 may present, via one or more graphical user interfaces displayed on a mobile or other device of a supervising anesthesiologist, patient monitoring parameters (e.g., ECG, heart rate, blood oxygenation) as determined from the received medical device data, procedure phase (e.g., induction, maintenance, and emergence), alarms, anesthesiology machine settings, and other relevant or selected information to a user (e.g., the supervising anesthesiologist). The processing and analysis of the time series streams of medical device data as described above in order to detect events relevant to identified cases (e.g., such as identifying a phase of anesthesia administration) may be utilized and the output of such processing and analysis may be provided to the supervisory application 44. The supervisory application 44 may provide determined values of specified patient monitoring parameters, indications of detected events, and other notifications as determined from the time series streams of medical device data to the user via the graphical user interfaces described herein.

For example, via the supervisory application 44, the user may toggle between graphical user interfaces that show limited information for a plurality of patients (a multi-patient GUI) and more detailed information for a selected patient (a single patient GUI). The user may also view, via the supervisory application 44, trends of patient monitoring data, detailed alarm/notification information, insights (including predictive functions), and/or other information. Further, the user may communicate with other care providers, such as a subordinate care provider that is in the room with a patient, via the supervisory application 44. The user may customize which patients/rooms to view, which patient monitoring parameters to view, which alarms and insights to apply, and other parameters of the graphical user interfaces used to present the above-described information, such as a layout of each graphical user interface.

The graphical user interfaces that are generated via the supervisory application 44 may be displayed on one or more suitable display devices associated with a respective care provider device and/or medical facility administration device. As shown in FIG. 1B, a plurality of care provider devices 120 may be included as part of hospital network 14, from a first care provider device 134, a second care provider device 136, and on up to an nth care provider device 138, and may be communicatively coupled to edge device 20 via hospital network 14. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility and substantially fixed in place (such as in a nurses station or in the room of a patient) and/or located locally or remotely from the medical facility and configured to move with the care provider (such as a care provider's mobile device).

When viewing graphical user interfaces generated via the supervisory application 44 via a display of a care provider device, a care provider may enter input (e.g., via the user input device, which may include a keyboard, mouse, microphone, touch screen, stylus, or other device) that may be processed by the care provider device and sent to edge device 20. In examples where the user input is a selection of a link or user interface control button of a graphical user interface, the user input may trigger progression to a desired view or state of the graphical user interface (e.g., trigger display of desired patient medical information), trigger updates to the configuration of the graphical user interface, trigger alarm, insight, and/or other notification settings to be saved, trigger changes to a machine (such as an anesthesia delivery machine), or other actions.

The devices disclosed herein, such as the care provider devices and/or aspects of the edge device 20, may each include a communication module, memory, and processor(s) to store and execute aspects of the supervisory application 44 as well as send and receive communications, graphical user interfaces, medical data, and other information.

Each communication module facilitates transmission of electronic data within and/or among one or more systems. Communication via the communication module can be implemented using one or more protocols. In some examples, communication via the communication module occurs according to one or more standards (e.g., Digital Imaging and Communications in Medicine (DICOM), Health Level Seven (HL7), ANSI X12N, etc.). The communication module can be a wired interface (e.g., a data bus, a Universal Serial Bus (USB) connection, etc.) and/or a wireless interface (e.g., radio frequency, infrared, near field communication (NFC), etc.). For example, a communication module may communicate via wired local area network (LAN), wireless LAN, wide area network (WAN), etc. using any past, present, or future communication protocol (e.g., BLUETOOTH®, USB 2.0, USB 3.0, etc.).

Each memory may include one or more data storage structures, such as optical memory devices, magnetic memory devices, or solid-state memory devices, for storing programs and routines executed by the processor(s) to carry out various functionalities disclosed herein. Memory may include any desired type of volatile and/or non-volatile memory such as, for example, static random access memory (SRAM), dynamic random access memory (DRAM), flash memory, read-only memory (ROM), etc. The processor(s) may be any suitable processor, processing unit, or microprocessor, for example. The processor(s) may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, edge device 20 is shown in FIG. 1B as constituting a single entity, but it is to be understood that edge device 20 may be distributed across multiple devices, such as across multiple servers.

The supervisory application 44 may provide various data, notifications, and messages to the plurality of care provider devices 120. The data, notifications, and/or messages may include historical data, real-time medical device data (e.g., provided by streaming server 114), and notifications that may be pushed to the plurality of care provider devices 120 from an event notification service 112 via MDD processing system 12 or another a cloud-based service.

Figure 2:
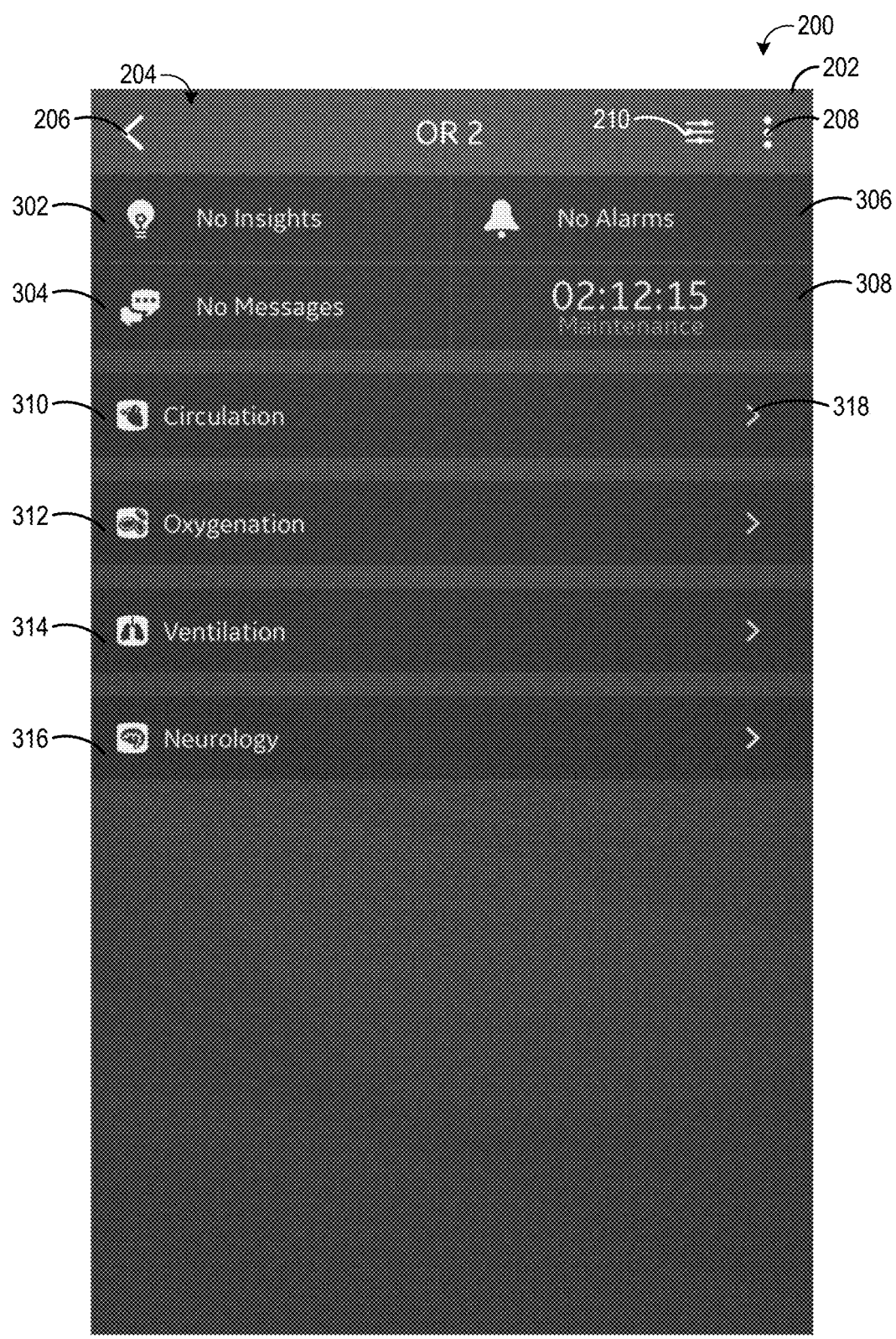
FIGS. 2-5 show an example display device displaying various views of a single-patient graphical user interface generated via the supervisory application.
Figure 4A:
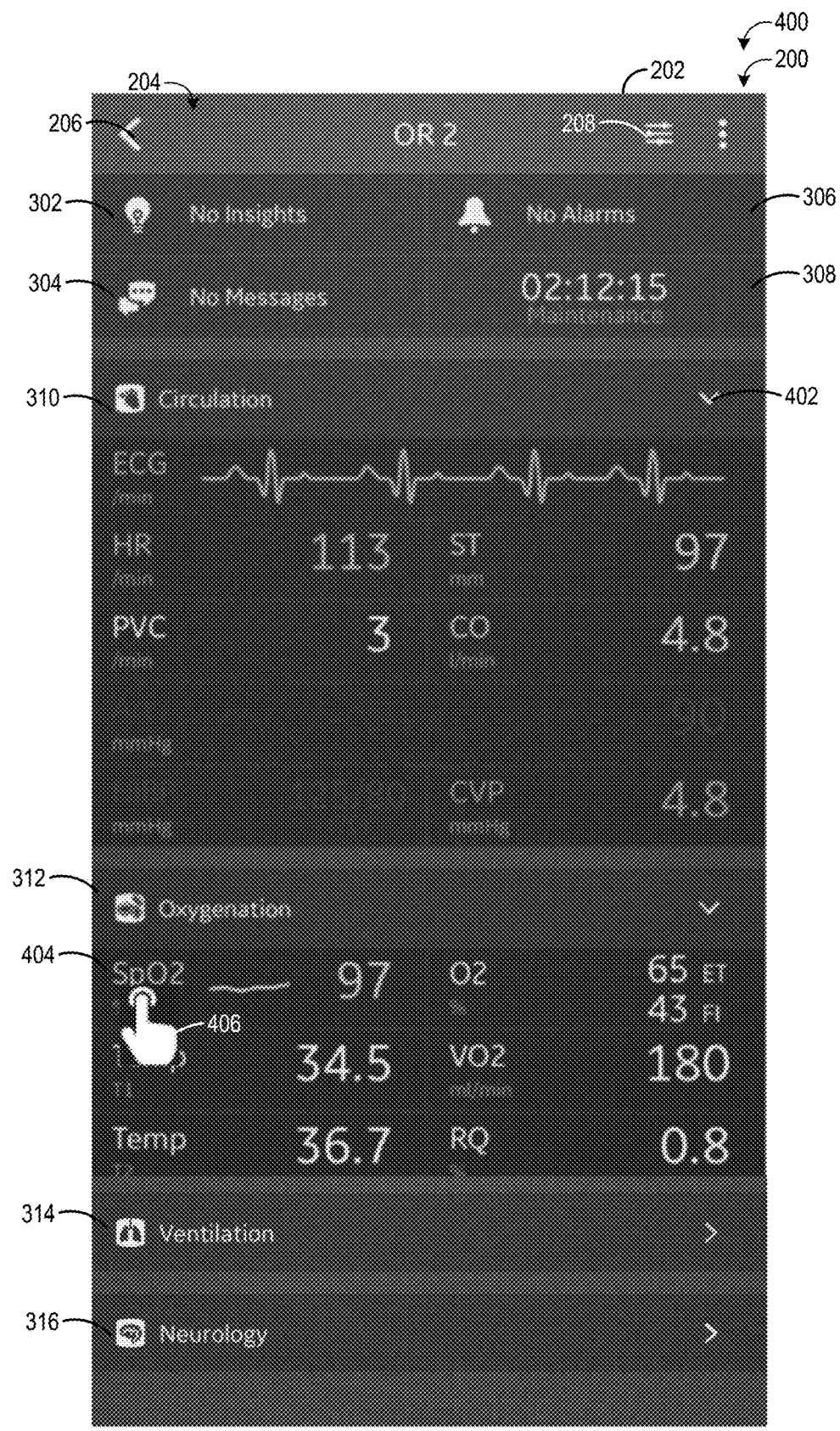

As will be explained in more detail below, the supervisory application 44 may be visualized on a care provider device in the form of one or more graphical user interfaces. The one or more graphical user interfaces may be populated with real-time patient monitoring parameters, such most-recently determined values or waveforms for heart rate, blood oxygen saturation, respiration rate, and so forth, obtained from the medical devices. When the medical device data is received by the edge device 20, some or all of the medical device data may be processed by stream processing module 106 and supplied to the streaming server 114, which may then supply the real-time patient monitoring parameter values and/or waveforms to a requesting care provider device. For example, when a user is viewing a patient-specific graphical user interface of the supervisory application 44 on care provider device 134, the graphical user interface may include tiles or other display areas where the most-recently determined values for selected patient monitoring parameters are displayed (for example, as shown in FIGS. 2 and 4A and explained in more detail below). The streaming server 114 may stream the most-recently determined values for the selected patient monitoring parameters to the care provider device 134, which may then populate the received values into the graphical user interface. The stream processing module 106 may include rule-based streaming analytics algorithms applying windowing functions (sliding, tumbling, hopping, etc.) used for waveform analysis and event detection, thereby triggering alerts, detection of surgical phases, flow analysis, triaging algorithms, etc. Furthermore, the stream processing module 106 coupled with inference engine 110 may perform predictions, referred to as predictive functions or predictive insights herein, such as continuously predictive scoring, patient deterioration scoring, calculate risk indexes, identify early signs of trouble, sepsis prediction, onset of respiratory distress, end-of-case prediction, and clinical decision support in general. Additional information regarding the predictions are presented below with respect to FIGS. 22-25 and 29-31.

The determination of which patient monitoring parameter values to send to which care provider device may be based at least in part on data requests sent by the care provider devices to the edge device 20. The edge device 20 may include a representational state transfer (REST) server, for example, that may receive data requests from the care provider devices 120 and may respond to the data requests by commanding the streaming server 114 to stream selected medical device data to a requesting care provider device(s). The streaming server 114 may maintain a stateful session (e.g., WebSocket) with each client (e.g., the care provider devices). The medical device data may be adapted (transformed and filtered) before being streamed to the client devices.

Figure 6:
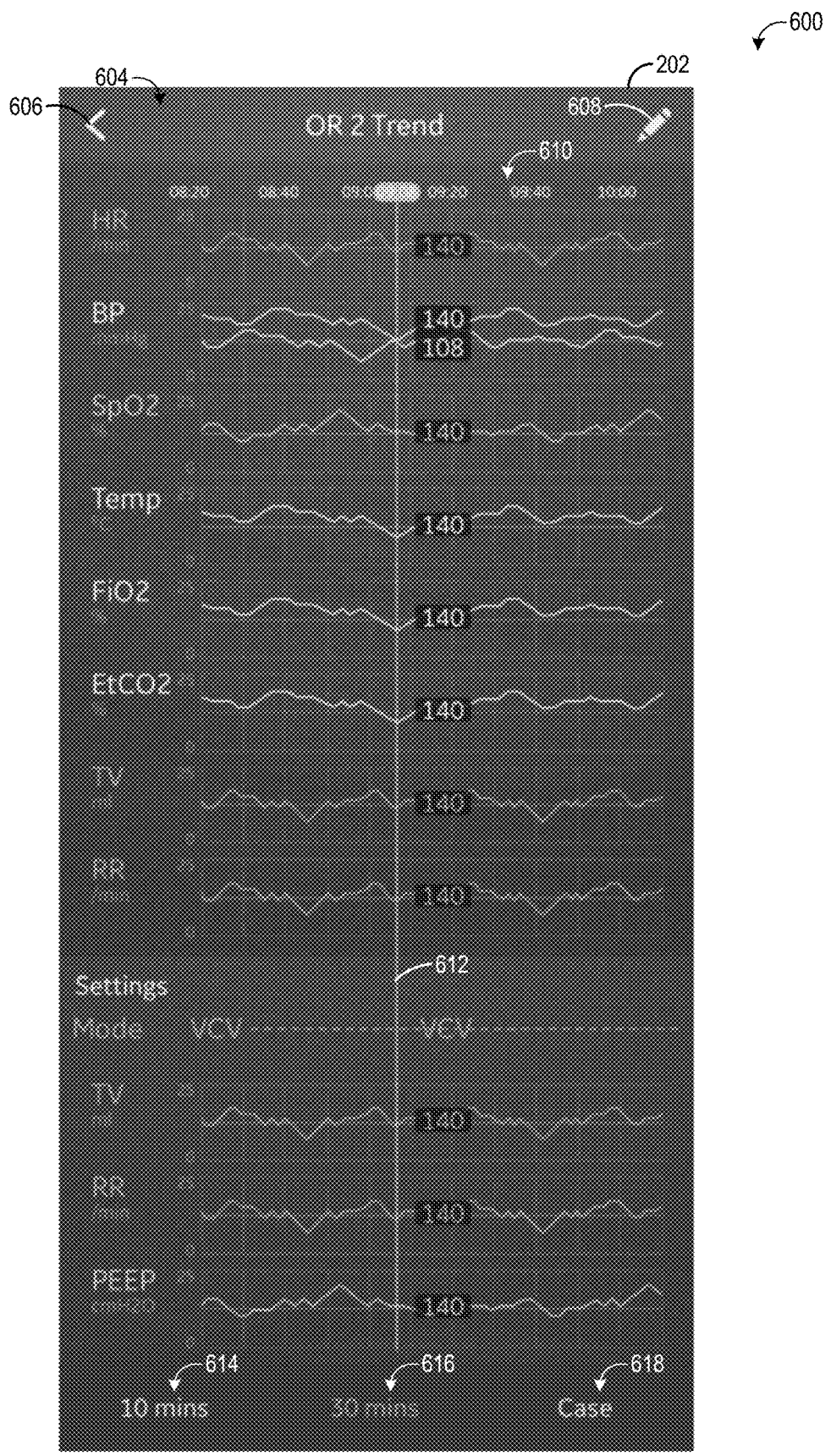
FIGS. 6 and 7 show the display device displaying various views of a trends graphical user interface generated via the supervisory application.

The data requests from the care provider devices 120 may also include requests for historical data (e.g., prior or non-real time patient monitoring parameter values). The historical data may include trends of selected patient monitoring parameters over time. For example, as shown in FIG. 6 and explained in more detail below, a trends graphical user interface may be displayed on a care provider device as part of the supervisory application 44 that shows values for selected patient monitoring parameters over time as trend lines. The trend lines may be assembled from stored medical device data (e.g., stored in data storage 104). When a user requests to view a trends graphical user interface on a care provider device, the care provider device may send a request for the trend lines that are to be displayed in the trends graphical user interface to the edge device 20, and the edge device 20 may obtain the trend lines from the data storage 104 or the edge device 20 may obtain relevant stored medical device data and the trend lines may be assembled at a different location (e.g., by the care provider device). Further, these trends may be entered as input to one or more predictive functions that are trained to output respective risk scores indicative of a likelihood that a patient will exhibit a given condition.

Figures 8, 9, 10:
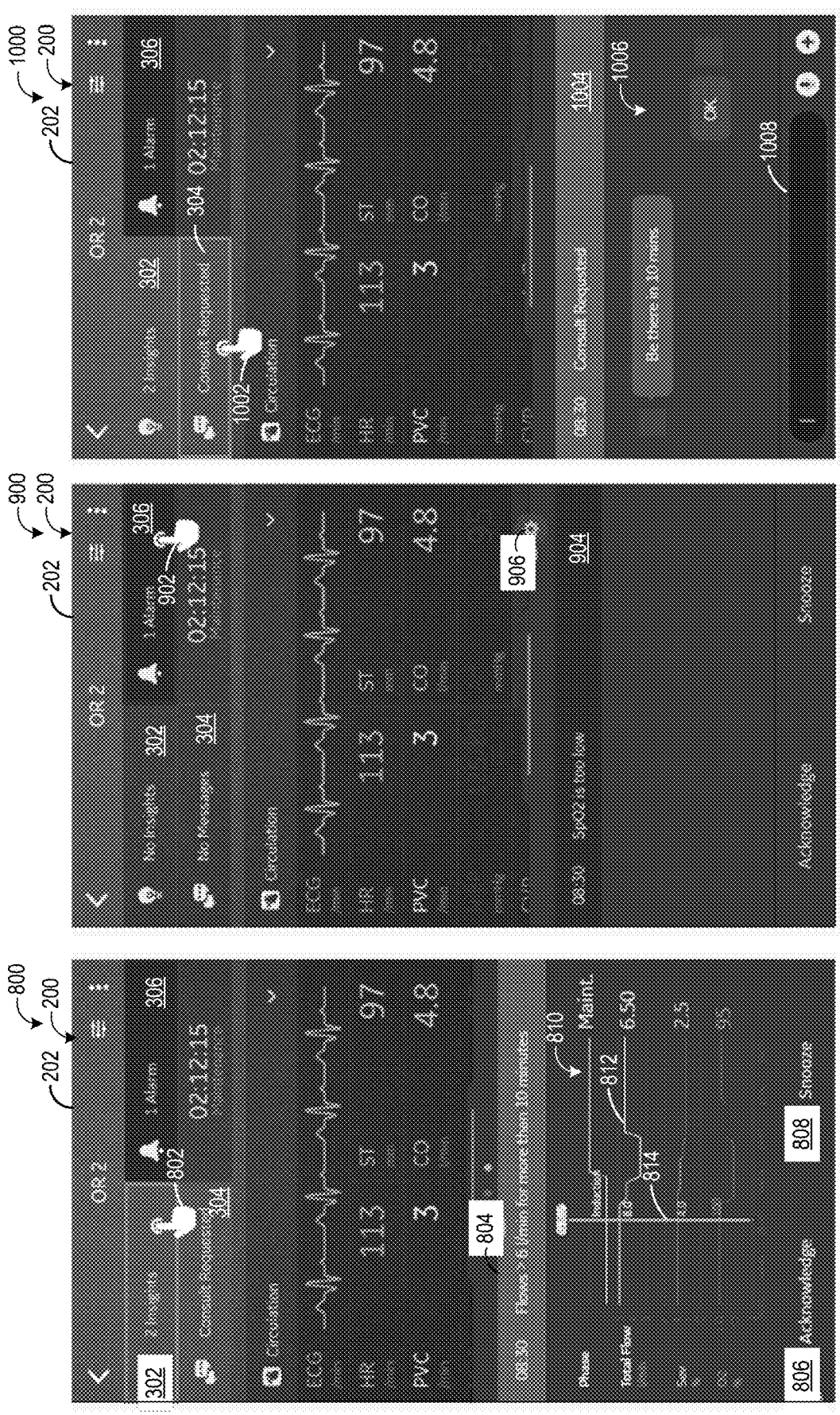
FIGS. 8-10 show the display device displaying various notifications output as part of the single-patient graphical user interface generated via the supervisory application.

The supervisory application 44 may generate and/or send various alarms and notifications based on the medical device data received from the various medical devices. The alarms may include threshold-based alarms, where a notification/alarm is generated and output to one or more care provider devices in response to a patient monitoring parameter value meeting a predetermined condition relative to a threshold (e.g., an alarm may be generated and sent to a care provider device in response to blood oxygen saturation for a particular patient dropping below a threshold saturation). For example, as shown in FIG. 9 and explained in more detail below, an alarm tile may be displayed as part of a single-patient or multi-patient graphical user interface of the supervisory application 44, where the alarm tile includes an indication of how many alarms have been triggered for a particular patient, where an alarm is generated by a medical device in response to a determination that a patient monitoring parameter for a particular patient has reached a predefined condition relative to a threshold.

The alarms described above may be triggered by a medical device monitoring the patient. For example, the patient may be monitored by a pulse oximeter, which may send SpO2 data to edge device 20 directly or via an anesthesia delivery machine. If the patient's blood oxygen saturation drops below a threshold, the pulse oximeter and/or anesthesia delivery machine may send a notification to edge device 20 indicating that the patient's SpO2 value has dropped below a threshold. Edge device 20, via event notification service 112 and/or cloud gateway 116, may send a notification of the alarm to the care provider device of the care provider attending to the patient. For example, the alarms that are generated may be sent to the appropriate care provider device(s) directly via event notification service 112 or via the cloud gateway 116, which may push the alarms (and other notifications that are generated by edge device 20, as explained in more detail below) via MDD processing system 12 to the appropriate care provider device(s), even when the supervisory application 44 is in an unlaunched state on the care provider device(s).

As mentioned above, the supervisory application 44 is configured to apply insights to the received medical device data in order to provide user-selected notifications, predictions, etc., of patient status. The insights may include the rule-based streaming analytics algorithms performed by the stream processing module 106 and/or inference engine 110 described above (e.g., waveform analysis and event detection, thereby triggering alerts, detection of surgical phases, flow analysis, triaging algorithms, continuously predictive scoring, patient deterioration scoring, calculate risk indexes, identify early signs of trouble, sepsis prediction, onset of respiratory distress, end-of-case prediction, and clinical decision support). The insights may include artificial intelligence based models, such as machine learning or deep learning models. In general, any algorithm, model, or set of rules that may be applied to the medical device data in order to monitor patient state may be considered an insight. In some examples, particularly where the insight requires a high amount of processing power, the insight may be stored/executed on a cloud based device such as the MDD processing system 12.

In some examples, insights may be defined by a user according to a predefined set of parameters and a predefined set of operators and saved as a set of rules. The predefined set of parameters may include all the patient monitoring parameters (including physiological data and machine parameters/settings) that are available to the system (e.g., all the patient monitoring parameters that can be measured, inferred, or otherwise determined from the medical device data). When a parameter is selected (e.g., when a patient monitoring parameter is selected), the user may be presented with a predefined scopes (e.g., timings) to select to limit the insight to specific procedures, timing, etc. Further, when a parameter is selected, the user may be presented with predefined or adjustable thresholds to apply to the parameter. The predefined set of operators may include an "and" operator, an "or" operator, a "while or during" operator, and/or any other suitable operators that allow the user to combine multiple parameters in an insight, or allow the user to select only one parameter for the insight.

Figure 20:
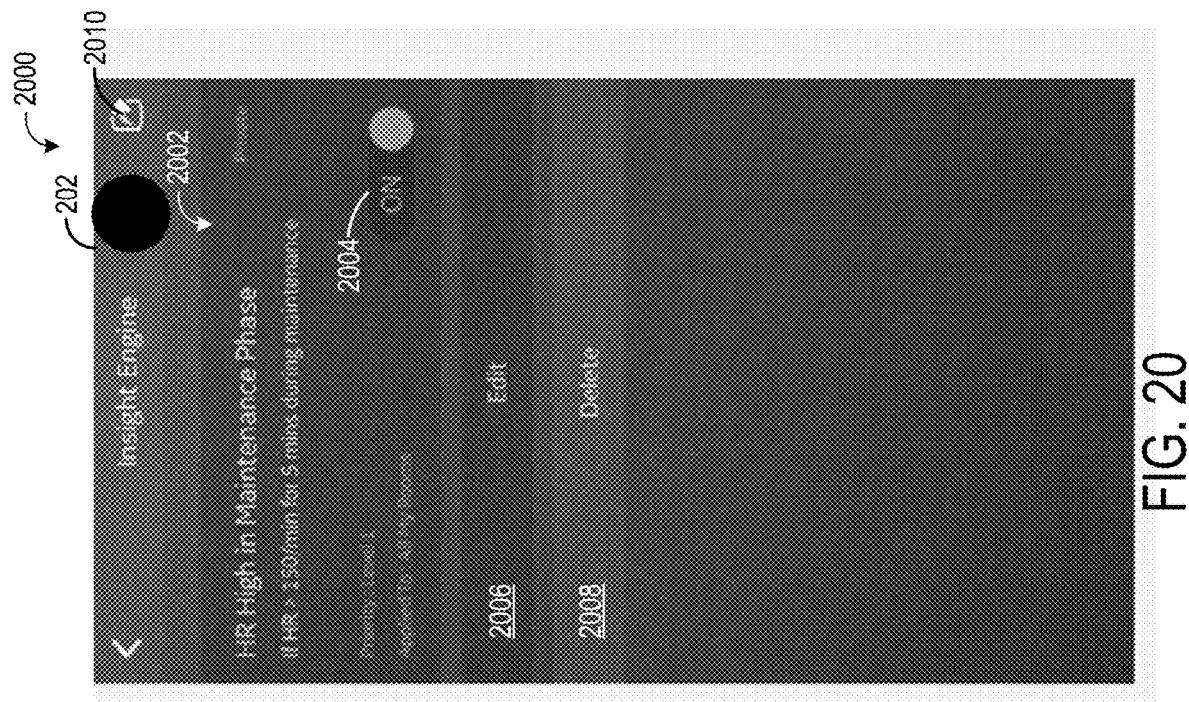

The rules engine 108 may include resources (e.g., memory and processors) of the edge device 20 allocated to store and apply sets of insight rules, which may be similar to alarms, but may be multi-modal and/or multi-parameter. The insights may be user-customized/defined. The insight rules may define a condition and a scope of each insight. For example, as shown in FIG. 20 and explained in more detail below, an insight may include a condition that defines a patient monitoring parameter and corresponding threshold value that may trigger the insight notification, such as patient heart rate being above 150 beats/minute. An insight may further include a scope, which may be a timing- or procedure-based limitation on when the condition of the insight will trigger a notification or result. For example, the scope may define the parameters during which the condition is to be applied, such as how long the condition is to persist before triggering the insight notification (e.g., five minutes), which stage of the procedure the condition is to occur in order to trigger the insight notification (e.g., in maintenance stage of anesthesia delivery), and so forth. As explained above, the user may define the condition and scope from the predefined set of parameters, and if more than one condition is desired in an insight, the user may select an operator from the predefined set of operators. When multiple conditions are included in an insight, after selecting an operator such as "and" or "or," the user may select another parameter from the set of parameters.

The insight rules may be customized by a user, and thus the insight rules may define which users (and hence which care provider devices) are to receive which insight notifications. The edge device 20 may distribute medical device data streams to the rules engine 108, and the rules engine 108 may apply the stored insight rules to the incoming streams of medical device data in order to determine if any insight notifications or results should be generated. If an insight notification is to be generated, an insight notification may be generated and sent to the appropriate care provider device(s) via the event notification service 112 and/or cloud gateway 116.

In some examples, an insight may include, as an input, the result of another insight. For example, a first insight may include an algorithm that determines a current anesthesia delivery phase for an anesthesia delivery machine. The output/result of the first insight may be displayed as a tile on a GUI of the supervisory application that is displayed on a care provider device, as will be explained in more detail below. The result of the first insight may also be used as input, along with the medical device data, to a second insight. For example, the second insight may dictate that a notification be output when a selected patient monitoring parameter value reaches a threshold value (or when a change in a selected patient monitoring parameter over a particular time period reaches a threshold) when the result from the first insight indicates that the patient is in maintenance phase of anesthesia delivery. A user may select to include the result of an insight as an input into another insight via the predefined set of parameters described above. For example, when the user creates an insight or applies an insight created by another user, that insight may be included in the predefined set of parameters.

Figure 17:
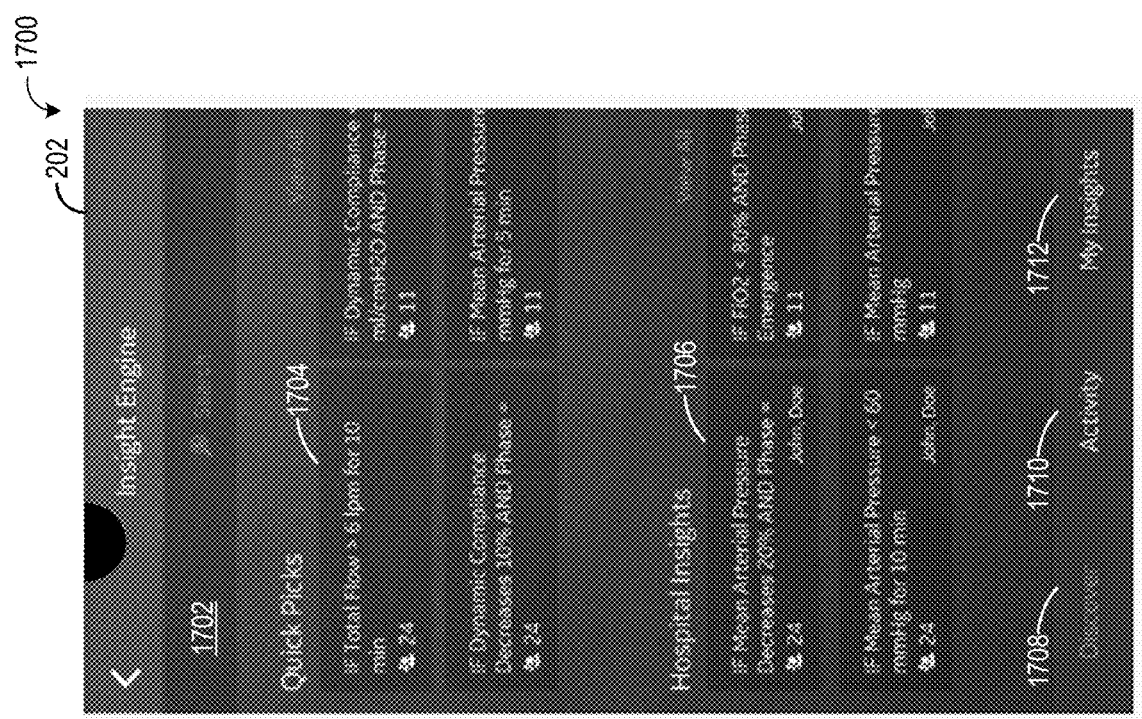

Further, insights may be shared with other users at the medical facility and/or other users at other medical facilities. Thus, when requested, insight rules may be saved at the MDD processing system 12. As shown in FIG. 17 and explained in more detail below, an insight graphical user interface of the supervisory application 44 may be displayed on a care provider device when requested. Via the insights graphical user interface, a user may search for insights defined by users at other medical facilities and/or for insights defined by users at the same medical facility as the user is located, as well as view insights defined by the user. If the user selects to apply an insight, the notification that the insight has been selected may be sent to the rules engine 108 and/or the inference engine 110 and saved as an insight rule to be applied for that user.

The inference engine 110 may be used with artificial intelligence (AI) based models, such as trained deep learning models, to process the incoming data and derive conclusions (insights) from the facts and rules contained in the various machine learning models. The inference engine 110 may be the run-time engine for AI based algorithms, such as prediction of patient deterioration/signs of trouble, and these will be part of the inference engine 110. In addition, there may be a deep learning and/or learning network in the cloud, e.g., MDD processing system 12, to train algorithms, where very high compute and resources are necessary.

As explained above, and will be explained in more detail below, via an insights engine feature of the supervisory application 44, users may create their own rules/algorithms from within a user interface and current available data to generate insights, based on their pre-configuration. The insights engine uses streaming, and applies windowing functions, to generate the insights. These insights are then notified to the respective users, based on the users' configuration (e.g., user-subscribed insights), using the event notification service 112. The available data to create a rule may include raw machine data, or the result of an AI algorithm powered by the inference engine 110 (e.g., another insight).

When a user creates their own insight (e.g., rule/algorithm) through the insights engine, they have the opportunity to share that the insight with other users, so other users can adopt and use the same insight. For example, a user may share an insight within the user's institution and other users can see how many people are using the insight and adopt the insight for their own patients/rooms. A user may also see rules (or "insights") that others on the platform outside the user's institution globally have set up, and see the popularity of each insight, and if desired, select one or more of the insights to be applied for their own patients/rooms.

Thus, as explained above, the supervisory application 44 may include a backend hosted on the edge device 20, where the backend includes a plurality of micro services, such as the rules engine 108, inference engine 110, event notification service 112, and streaming server 114. The supervisory application 44, via the backend/edge device 20, may output real-time medical device data to a plurality of care provider devices, trends of medical device data, messages, alarms, insight notifications/results, and/or other information as requested by the front end of the supervisory application 44 that is executed on the care provider devices. The front end of the supervisory application 44 may include a supervisory application visualization platform that may be stored on each care provider device. The supervisory application visualization platform, such as supervisory application visualization platform 135 stored on care provider device 134, may render the data received from the edge device 20 into one or more graphical user interfaces. Additionally, the aspects of the supervisory application 44 that are saved on each care provider device may include various container, component, and presentation layers to receive the data from the edge device 20, populate the graphical user interfaces with the received data, send and receive messages, display notifications, collect GUI settings and other requested customizations (and send the settings/configurations to the edge device 20) and so forth. As an example, the historical data received form the edge device 20 (e.g., the trends) may be sent to a first layer via a REST application programming interface (API), the real-time medical device data may be streamed to the first layer via a web socket, and the push notifications sent from the MDD processing system 12 may be received, processed, and displayed via the visualization platform. Further, when interacting with the graphical user interfaces of the supervisory application, the user may adjust various settings (such as which patient monitoring parameters to display) activate or deactivate alarm notifications, create insights, and so forth. These user-specific preferences/configurations may be saved on the edge device 20 in a preferences/configuration database.

In some embodiments, medical device data and/or other information requested via the supervisory application 44 may be obtained from an electronic medical records (EMR) database 122. For example, historical data (e.g., trend lines) may be obtained from the EMR database 122 in addition to or instead of data storage 104. EMR database 122 may be an external database via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR database 122 is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

The edge device 20 can be implemented in a variety of hardware and/or software implementations and it should be noted that such implementations are not considered to be limiting. For example, it is contemplated that any or all of the edge device 20 may be embodied exclusively in hardware, exclusively in software, exclusively in firmware, or in any combination of hardware, software, and/or firmware. The examples provided herein are not the only way to implement such methods and systems.

In exemplary and non-limiting embodiments of the edge device, the edge device 20 is implemented by one or more processors or computing devices. Memory and processors as referred to herein can be standalone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to, RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

Figure 13:
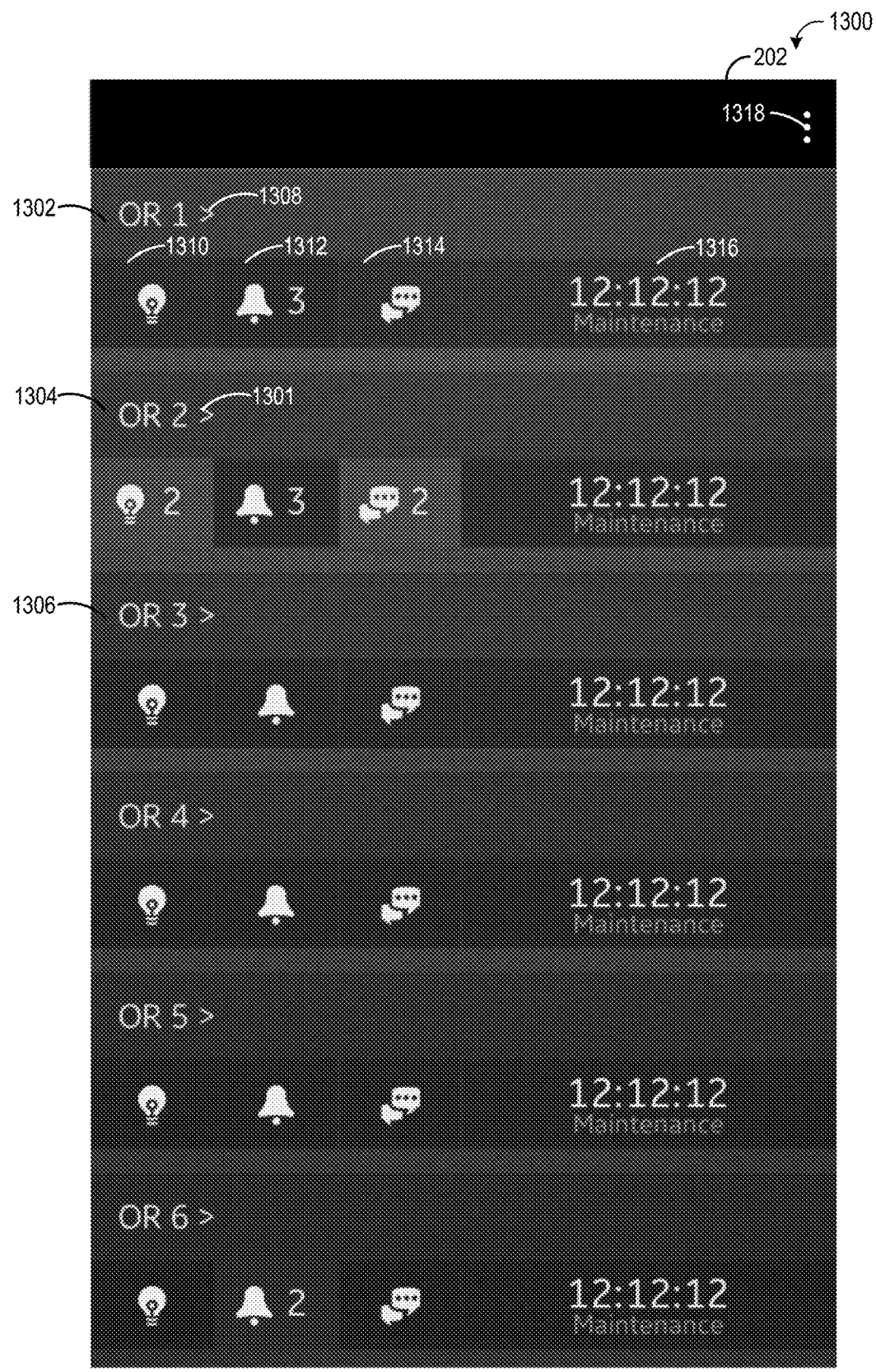

FIG. 2 shows an example single-patient graphical user interface (GUI) 200 that may be displayed when supervisory application 44 is launched on a supervising care provider device. Single-patient GUI 200 may be displayed on a display device 202. Display device 202 may include a screen on which the single-patient GUI is displayed and may be coupled to and/or included as a part of a computing device, such as care provider device 134. Single-patient GUI 200 may be displayed in response to a user request to display the GUI. For example, a user may launch the supervisory application 44 by selecting a supervisory application icon displayed on a home page of the display device. When the supervisory application 44 launches (at least initially), the user may be authenticated via a suitable authentication method, such as via a password, facial recognition, fingerprint recognition, etc. Upon authentication, the user may select to view the single-patient GUI 200 from a suitable menu. For example, the user may access a multi-patient interface that includes a global view of all patients the user has selected to monitor (which may include all patients at the medical facility the care provider is attending to) and may select a desired patient to view. An example multi-patient GUI 1300 is shown in FIG. 13. Multi-patient GUI 1300 may be displayed on display device 202 (or other suitable display device associated with a care provider device) and may include all patients/rooms selected by a user for monitoring. As shown, multi-patient GUI 1300 includes links to patient-specific interfaces. In the examples shown herein, rather than identifying each patient by name or a patient ID number, each patient-specific interface may be identified by the room that patient is currently located in. For example, as shown in FIG. 13, links are displayed for interfaces specific to patients located in a first operating room (OR 1), a second operating room (OR 2), a third operating room (OR 3), and so forth. Additional patient links may be viewed by scrolling the interface. Selection of a patient link may launch the single-patient GUI for that patient. For example, selection of forward button 1301 for OR 2 may cause the single-patient GUI 200 to be displayed.

Returning to FIG. 2, single-patient GUI 200 may include an identification header 204 that identifies the patient whose medical device data/status is being displayed, in the form of the room in which the patient is currently located. In the illustrated example, single-patient GUI 200 is specific to the patient located in the second operating room of the medical facility (OR 2). Identification header 204 may include a back button 206, which when selected via user input (e.g., via touch input to the back button) may cause display of a multi-patient GUI (such as multi-patient GUI 1300 of FIG. 13). Identification header 204 may further include one or more menu buttons, such as menu button 208. When menu button 208 is selected, a context menu may be displayed, which will be explained in more detail below with respect to FIG. 5.

Figure 3:
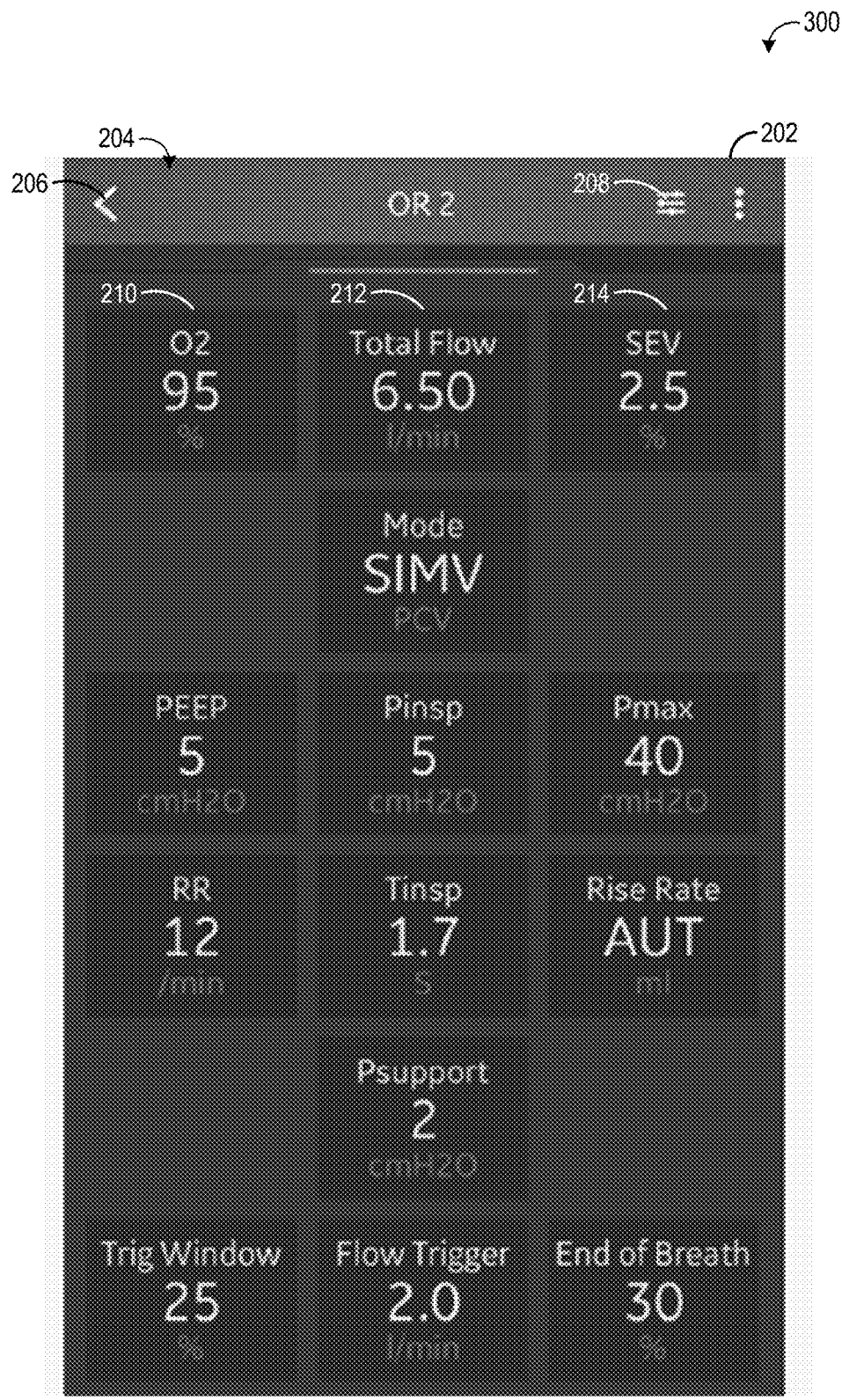

Identification header also includes a parameter view button 210 that, when selected causes display of a parameter view where machine settings/parameters for the one or more medical devices monitoring the patient and/or delivery therapy to the patient (such as machine settings for an anesthesia machine) are displayed. FIG. 3 shows an example parameter view 300 displayed on display device 202 in response to selection of the parameter view button 210. Parameter view 300 displays machine parameters in a first layout that includes an array of tiles. Each selected machine parameter may be displayed as a respective tile, such as a first tile 210, a second tile 212, and a third tile 214. In the example shown in FIG. 3, the first tile 210 displays a first parameter, oxygen percentage, the second tile 212 displays a second parameter, oxygen or medical gas flow rate to the patient, and the third tile 214 displays a third parameter, anesthetic agent type and concentration. Each parameter tile that is displayed via the parameter view 300 may present a most-recently determined value of the respective machine parameter. For example, the first tile 210 is presenting an oxygen concentration of 95%, the second tile 212 is presenting a gas flow rate of 6.50 L/min, and the third tile 214 is presenting a sevoflurane concentration of 2.5%. Each determined value that is presented via a machine parameter tile may be determined from the time series streams of medical device data described above with respect to FIGS. 1A and 1B, and as such may be sent to the care provider device from the edge device 20 via the supervisory application 44. The determined values that are displayed in the parameter view 300, as well as other determined values (such as the patient monitoring parameter values that will be explained in more detail below) may be measured values, estimated values, and/or inferred values. For example, SpO2 may be directly measured from a pulse oximeter, while respiration rate may be inferred from the output of a capnography or from the output form the pulse oximeter.

The patient monitoring parameter tiles included in the single-patient GUI 200 (described below) may present physiological data (e.g., SpO2, respiration rate) of the patient as obtained from one or more patient monitoring medical devices (e.g., a pulse oximeter, a capnograph). The machine parameter tiles included in the single-patient GUI 200 and/or parameter view 300 may present machine data of one or more therapy medical devices that are being utilized during a medical procedure being performed on the patient, such as an anesthesia delivery machine. The machine data may include machine settings or parameters (e.g., ventilator mode, anesthesia type and concentration).

Returning to FIG. 2, single-patient GUI 200 further includes an insights tile 302, a message tile 304, an alarms tile 306, and a procedure timing tile 308. The insights tile 302 may notify the user if any of the user's preset and saved insights have been triggered, which will be explained in more detail below. Briefly, the insights may be similar to threshold-based alarms, but may be multi-modal and/or multi-parameter such that an insight may only be triggered when more than one parameter meets a predetermined condition and/or when a selected parameter meets a predetermined condition during a particular stage of a medical procedure, meets the predetermined condition for a specified amount of time, changes at a specified rate, etc. The messages tile 304 may notify the user if any messages have been received, such as text messages from another care provider. The alarms tile 306 may notify the user if any alarms have been triggered. An alarm may be triggered when a select patient monitoring parameter, such as SpO2, reaches a predetermined condition relative to a threshold, such as SpO2 dropping below 90%. The procedure timing tile 308 may inform the user of the current progress on the medical procedure being performed on the patient. For example, as shown in FIG. 2, an amount of elapsed time since commencement of anesthesia delivery is shown (e.g., 02:12:15), as well as the current phase of the anesthesia delivery (e.g., maintenance phase). The phase of anesthesia delivery may be determined by a phase determining insight that may be executed by the MDD processing system 12 and/or edge device 20, as explained above with respect to FIGS. 1A and 1B.

Additional patient monitoring parameters that are displayable via single-patient GUI 200 may be organized into categories, and each patient monitoring category may be collapsed or expanded. When collapsed, no patient monitoring parameters for that category are displayed. When expanded, the patient monitoring parameters for that category are displayed. FIG. 2 shows each category in a collapsed configuration. The patient monitoring categories shown in FIG. 2 include a circulation category 310, an oxygenation category 312, a ventilation category 314, and a neurology category 316, although other categories are possible without departing from the scope of this disclosure. The displayed patient monitoring categories may be customized by the user, such that the user may select which categories will be displayed on that user's device. Each patient monitoring category includes a forward arrow, such as forward arrow 318, which when selected by the user causes the category to expand so that the patient monitoring parameters in that category may be viewed.

FIG. 4A shows a first view 400 of a progression through different views of single-patient GUI 200. In the first view 400, the user has selected two categories to expand (the circulation category 310 and the oxygenation category 312) and two categories remain collapsed (the ventilation category 314 and the neurology category 316). When a category is expanded, the associated forward arrow may switch to a down arrow, as shown by down arrow 402, to signify that the category has been expanded. User selection of the down arrow causes the category to collapse.

As appreciated by FIG. 4A, when a category is expanded, a plurality of patient monitoring parameters may be displayed. For example, the circulation category 310 includes eight patient monitoring parameters (e.g., an ECG waveform, a most-recently determined heart rate, and so forth) each related to circulation. The oxygenation category 312 includes six patient monitoring parameters (e.g., a most-recently determined SpO2), each related to oxygenation. The patient monitoring parameters that are included in each category may be selected by the user via an edit function, which may be executed via the context menu of FIG. 5 or by a user input made to a category. For example, a swipe motion on the circulation category 310 banner may trigger display of an edit button. Selection of the edit button may trigger control buttons to be displayed, via which patient monitoring parameters in the category may be deleted and/or additional patient monitoring parameters may be added. In this way, the edit/customization functionality gives the power to the user to view any parameter in the system using the single-patient GUI, including a trend of that parameter, within a tile. For example, via the edit function, the user may choose to view a patient monitoring parameter as a single value (e.g., most recently determined value), as a trend showing change in the patient monitoring parameter over time, or both. The user has the power to create their own views, their own insights, and so forth, as will be explained in more detail below.

As explained above, one or more of the patient monitoring parameters that are displayed in the expanded view of a category may include a most-recently determined value for that parameter. For example, in the oxygenation category 312, an SpO2 tile 404 may be displayed, showing the most-recently obtained SpO2 value. However, it may be beneficial for the user to view a change in the values of a patient monitoring parameter over time. To access a view where one or more patient monitoring parameter trends are displayed, the user may enter an input to a selected patient monitoring parameter tile, such as a single touch input (schematically shown by hand 406) to SpO2 tile 404. Selection of the patient monitoring parameter tile may trigger a trend view for the selected patient monitoring parameter, as shown in FIG. 4B.

Figure 4B:
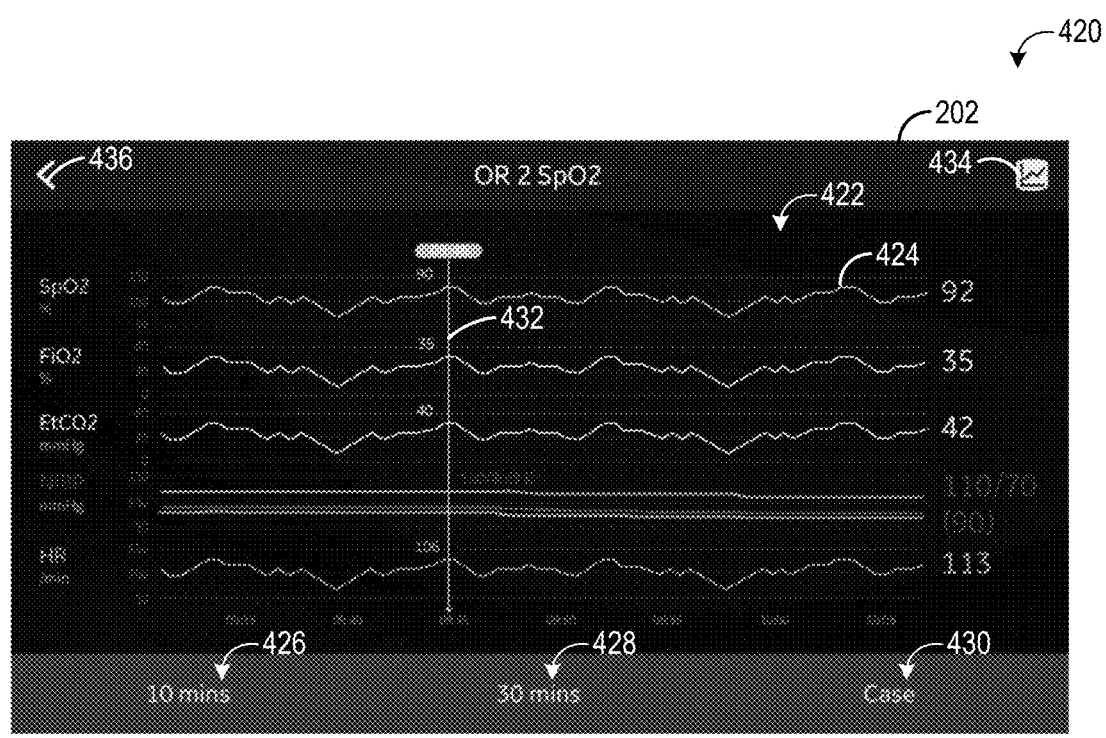

FIG. 4B shows a second view 420 of single-patient GUI 200 displayed on display device 202. Second view 420 includes a set of trends 422 that may be displayed in response to user selection of the SpO2 tile 404. The set of trends 422 may be displayed as an overlay on top of the first view 400, or the set of trends 422 may be displayed as a separate window, taking the place of or fully obscuring the first view 400. The set of trends 422 includes an SpO2 trend line 424 and a plurality of related trend lines, herein the fraction of inspired air comprised of oxygen (FiO2), end-tidal CO2 (EtCO2), blood pressure (NIBP, including diastolic and systolic measurements), and heart rate (HR). Each trend line is plotted on its own y-axis, such that the values of each patient monitoring parameter may be plotted on different scales and with different units where applicable. Each trend line is plotted on a common x-axis, so that the trend lines are time-aligned. The trend lines may be stacked vertically. In this way, relationships or correspondence of changes among the displayed patient monitoring parameters may be easily identified by a viewer.

The patient monitoring parameter trends that are displayed along with the SpO2 trend line 424 in response to the selection of the SpO2 tile 404 may include trends of patient monitoring parameters not necessarily included in the oxygenation category 312. For example, EtCO2 may be displayed as part of the ventilation category 314, while NIBP and HR are each displayed as part of the circulation category 310. FiO2 may not be displayed in any of the categories shown in FIG. 4A. In this way, the patient monitoring parameters may be grouped together in categories based on the relatedness of what each patient monitoring parameter is detecting, which may aid the user in being able to quickly navigate to view a desired patient monitoring parameter(s) when viewing the first view 400 or another view that shows the most-recently determined values for each patient monitoring parameter. Then, when the user wants to view a trend for a selected patient monitoring parameter, other patient monitoring parameters that have been predetermined to be related to the selected patient monitoring parameter, or otherwise have been predetermined to be informative about past or current patient status, may be presented along with the selected patient monitoring trend, without the user having to enter additional inputs.

The patient monitoring parameter trends that are displayed along with the selected patient monitoring trend may be predetermined by the user, e.g., via a settings menu. In other examples, the patient monitoring parameter trends that are displayed along with the selected patient monitoring trend may be automatically determined by the supervisory application 44. For example, the supervisory application 44 may include default sets of related patient monitoring parameters, and when one patient monitoring parameter in a set is selected, all other patient monitoring parameters in that set may also be displayed. In some examples, the supervisory application 44 may learn or otherwise adjust over time which patient monitoring parameter trends should be displayed together.

The second view 420 further includes time range control buttons displayed along a bottom of the set of trends 422. For example, a first time range control button 426 may be selected to show the set of trends over a first time range (e.g., 10 minutes), a second time range control button 428 may be selected to show the set of trends over a second time range (e.g., 30 minutes), and a third time range control button 430 may be selected to show the set of trends over a third time range (e.g., the entirety of the case/procedure). However, other time ranges are possible without departing from the scope of this disclosure.

In some examples, user input to the set of trends 422 may cause display of a timeline 432. The timeline 432 may include a vertical line bisecting each trend line at a given point in time. The timeline 432 may be moved (e.g., drug) along the x-axis to a desired time point. Further, instantaneous values of each patient monitoring parameter at the time point corresponding to the position of the timeline may be displayed alongside the timeline 432. For example, in FIG. 4B, the timeline 432 is positioned at 09:46, and thus values for SpO2, FiO2, EtCO2, NIBP, and HR determined at or near 09:46 (or, depending on the frequency at which each patient monitoring parameter is determined, an inference of the value at that time) are displayed next to the timeline 432.

The second view 420 further includes, at least in some examples, a trends icon 434. User selection of the trends icon 434 may cause a trends GUI to be displayed, which will be explained in more detail below with respect to FIGS. 6 and 7. Additionally, the second view 420 includes a back button 436. When selected, the back button 436 may trigger display of the first view 410 and/or other view of the single-patient GUI that was previously displayed.

Figure 4C:
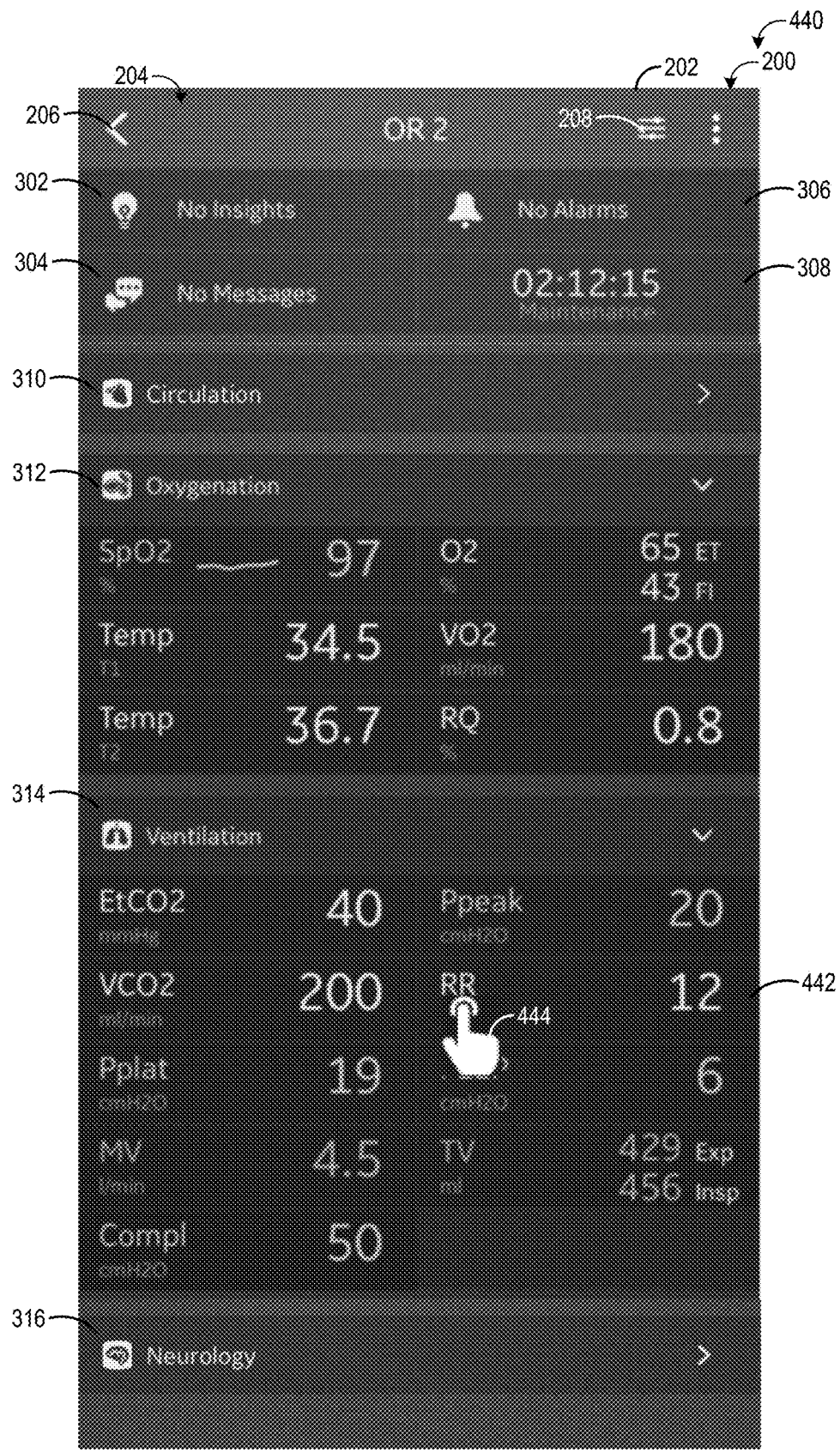

FIG. 4C shows a third view 440 of the single-patient GUI 200. In the third view 440, the circulation category 310 has been collapsed, the oxygenation category 312 remains expanded, the ventilation category 314 is expanded, and the neurology category 316 remains collapsed. In the example shown in FIG. 4C, the ventilation category 314 includes nine patient monitoring parameters (e.g., EtCO2, respiration rate (RR), plateau pressure (Pplat), and so forth) each related to ventilation.

As explained above, the user may select a patient monitoring parameter tile in order to view a trend for that patient monitoring parameter over time. In the example shown in FIG. 4C, the user is selecting a respiration rate (RR) tile 442 via a touch input (shown schematically by hand 444). Selection of the respiration rate tile 442 causes a set of trends to be displayed as an overlay across a portion of the third view 440, as shown in FIG. 4D.

Figure 4D:
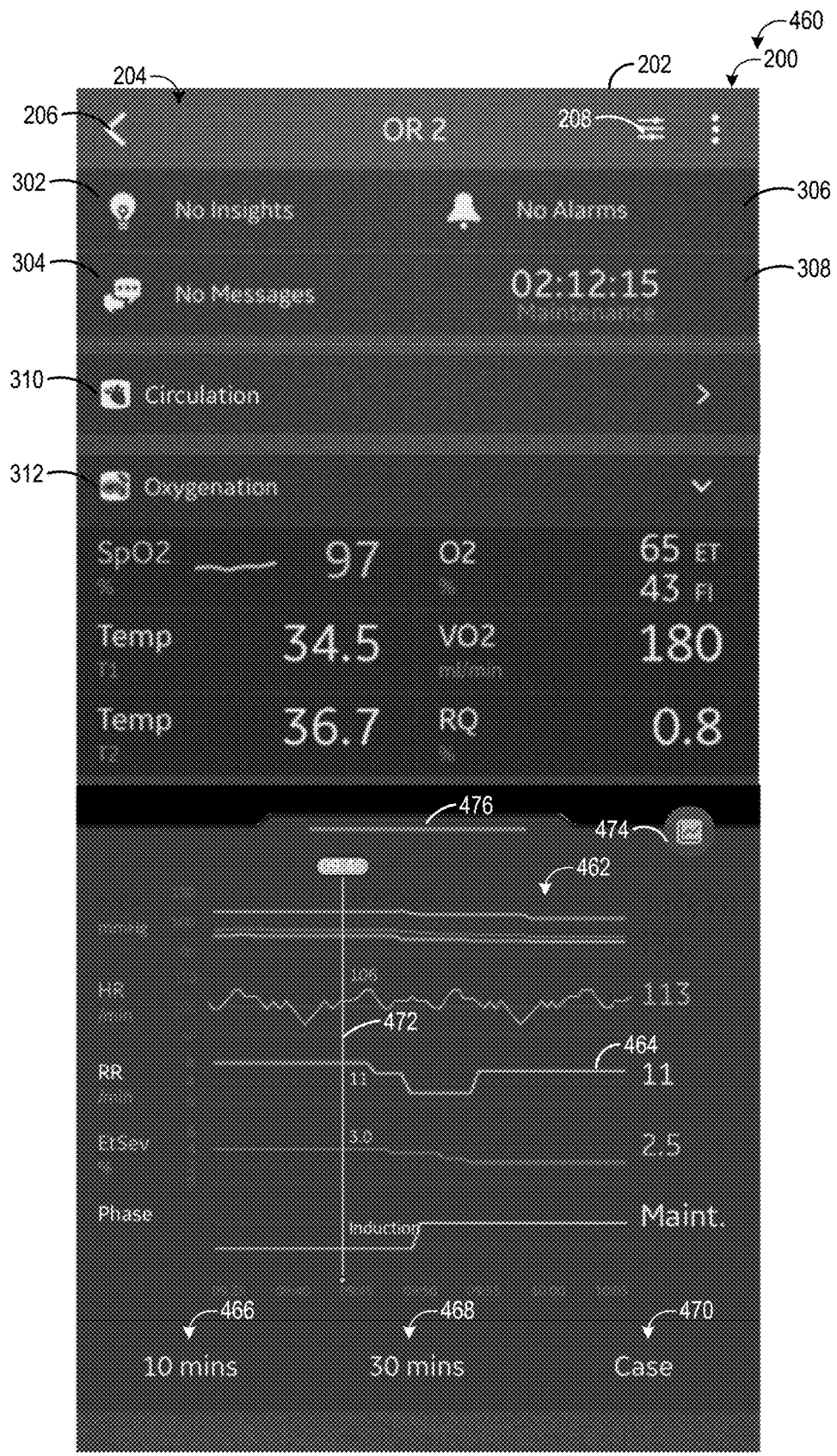

FIG. 4D shows a fourth view 460 of single-patient GUI 200. In the fourth view 460, a set of trends 462 is displayed at a bottom portion of the single-patient GUI 200. The set of trends 462 includes a trend line 464 for respiration rate, as the set of trends 462 was displayed in response to user selection of the respiration rate tile 442, as explained above with respect to FIG. 4C. The set of trends 462 includes a plurality of related trend lines, herein blood pressure (NIBP, including diastolic and systolic measurements), heart rate (HR), end-tidal concentration of sevoflurane (EtSev), and anesthesia phase (e.g., induction, maintenance, or emergence). Each trend line is plotted on its own y-axis, such that the values of each patient monitoring parameter may be plotted on different scales and with different units where applicable. Each trend line is plotted on a common x-axis, so that the trend lines are time-aligned. The trend lines may be stacked vertically. In this way, relationships or correspondence of changes among the displayed patient monitoring parameters may be easily identified by the user.

As explained previously, the patient monitoring parameter trends that are displayed along with the respiration rate trend line 464 may include trends of patient monitoring parameters not necessarily included in the same category as respiration rate. Further, the patient monitoring parameter trends that are displayed along with the respiration rate trend may be predetermined by the user or determined automatically by the supervisory application.

The fourth view 460 further includes time range control buttons displayed along a bottom of the set of trends 462. For example, a first time range control button 466 may be selected to show the set of trends over a first time range (e.g., 10 minutes), a second time range control button 468 may be selected to show the set of trends over a second time range (e.g., 30 minutes), and a third time range control button 470 may be selected to show the set of trends over a third time range (e.g., the entirety of the case/procedure). However, other time ranges are possible without departing from the scope of this disclosure. When prompted, a timeline 472 may be displayed, similar to the timeline 432 described above.

The fourth view 460 further includes, at least in some examples, a trends icon 474. Additionally, the fourth view 460 includes a swipe tab 476. When the user makes a down-swipe motion to the swipe tab 476, the set of trends 462 may collapse to reveal the categories/patient monitoring parameters displayed in the third view 440. When the set of trends is collapsed, the swipe tab 476 may be visible, and an up-swipe motion to the swipe tab 476 may cause the set of trends 462 to be displayed again.

In some examples, when the user selects a patient monitoring parameter tile, the resultant set of trends may be displayed in the manner shown in FIG. 4D when the display device 202 is at a first orientation (e.g., portrait, with the longitudinal axis of the display device oriented vertically with respect to the ground) and the set of trends may be displayed in the manner shown in FIG. 4B when the display device 202 is at a second orientation (e.g., landscape, with the longitudinal axis of the display device orientated horizontally with respect to the ground).

While FIGS. 4C and 4D illustrated a patient monitoring parameter trend and a set of additional trends of related patient monitoring parameters, in some examples, when a patient monitoring parameter tile is selected, a more detailed trend view for only that patient monitoring parameter may be shown. For example, referring back to FIG. 4A, one of the patient monitoring parameter tiles included in the circulation category is an ECG tile, where the patient's ECG signal is represented by a single waveform. However, ECG monitors may include multiple electrodes/leads, such as 12, each generating a respective ECG signal. Selection of the ECG tile may cause a trends view to be displayed where only ECG signals are shown, such as the signals from some or all of the ECG leads.

Figure 5:
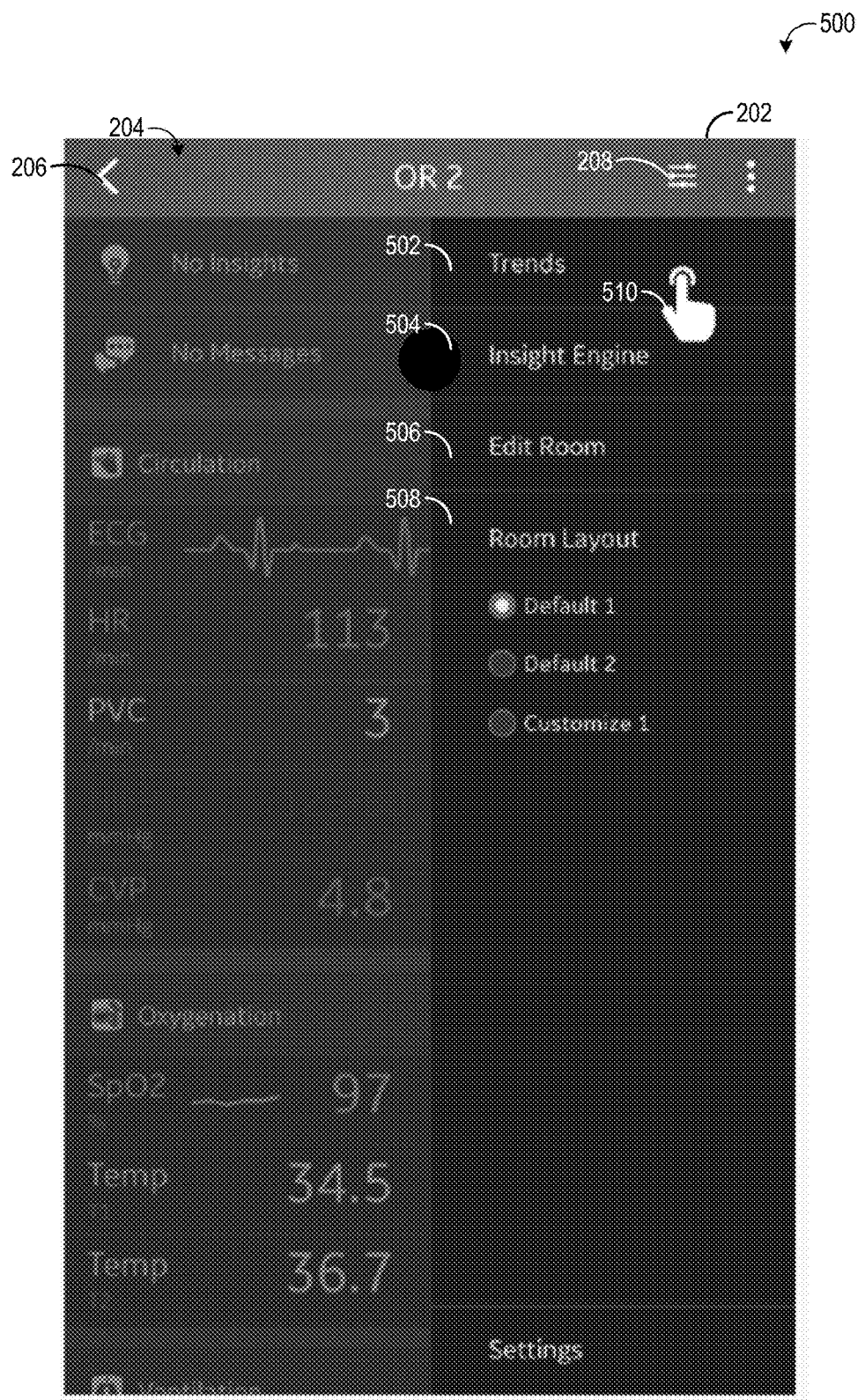

FIG. 5 shows a context menu 500 that may be displayed as part of a single-patient GUI, such as single-patient GUI 200. The context menu 500 may be displayed in response to user selection of the menu button 208. The context menu 500 may be displayed as an overlay on top of an existing view of the single-patient GUI (as shown in FIG. 5) or as a separate menu.

The context menu 500 may include a plurality of control buttons that may trigger different actions. For example, the context menu 500 may include a trends button 502, an insights engine button 504 (which may trigger display of an insights GUI, as will be described in more detail below with respect to FIGS. 17-20), an edit room button 506, and a room layout set of buttons 508. The room layout set of buttons 508 may include a button for each different possible layout for how the single-patient GUI is configured for display. For example, a first layout (e.g., corresponding to single-patient GUI 200) may be displayed when the "Default 1" button is selected, a second default/preconfigured layout may be displayed when the "Default 2" button is selected, and a third layout (which may be a layout customized by the user) may be displayed when the "Customize 1" button is selected. When a user makes adjustments to the layout of a single-patient GUI, including changing which patient monitoring parameter tiles are included in the single-patient GUI, the user may save the layout of the single-patient GUI, which may then be selectable as a customized layout from the context menu.

When the edit room button 506 is selected, the single-patient GUI (in the chosen layout) may be displayed with selectable control buttons displayed for each currently-selected patient monitoring parameter. User input to a control button may toggle that patient monitoring parameter between being selected (and thus included in the GUI) and not selected (and thus not included in the GUI). Additional patient monitoring parameter(s) may be added via an add control button. Further details of how patient monitoring parameters may be added to a GUI are presented below with respect to FIGS. 15 and 16. In some examples, when a patient monitoring parameter is added to the GUI or removed from the GUI, one or more of the remaining patient monitoring parameter tiles may be adjusted (e.g., moved from a first location to a second location, resized, rescaled, adjusted to show more or less information) in order to accommodate the new patient monitoring parameter tile, present a visually pleasing and easy to view arrangement of tiles, show as much information as possible on the display, etc. The adjustment of the one or more remaining tiles may be performed automatically, or the user may make desired adjustments in the manner described herein.

In the example shown in FIG. 5, a touch input is being entered to the trends button 502 (shown schematically by hand 510). Selection of the trends button 502 causes a trends GUI to be displayed. FIG. 6 shows an example trends GUI 600 that may be displayed in response to selection of a trends button from a context menu (e.g., selection of trends button 502) and/or in response to selection of a trends icon (e.g., trends icon 474). Trends GUI 600 is specific to a selected patient, herein the patient located in OR 2. Trends GUI 600 includes an identification header 604 that identifies the patient for which the trends are being displayed, including a back button 606 and an edit button 608. When selected, the edit button 608 may allow a user to select which trends to view via the trends GUI 600. The trends GUI 600 may be similar to the sets of trends that may be displayed in response to user selection of a patient monitoring parameter, as explained above with respect to FIGS. 4B and 4D. As such, the trends GUI 600 may include a set of trends 610 for each of a plurality of patient monitoring parameters, time-aligned and stacked vertically. When prompted, trends GUI 600 may display a timeline 612, similar to the timeline 432 described above, that bisects each trend line and that may be moved along the x-axis to a desired time. As explained above, the timeline 612 may include an instantaneous value for each patient monitoring parameter at the time coinciding with the position of the timeline 612.

The trends GUI 600 further includes time range control buttons displayed along a bottom of the set of trends 610. For example, a first time range control button 614 may be selected to show the set of trends over a first time range (e.g., 10 minutes), a second time range control button 616 may be selected to show the set of trends over a second time range (e.g., 30 minutes), and a third time range control button 618 may be selected to show the set of trends over a third time range (e.g., the entirety of the case/procedure). However, other time ranges are possible without departing from the scope of this disclosure.

As shown in FIG. 6, the displayed physiological parameter trends include heart rate, blood pressure, SpO2, temperature, FiO2, EtCO2, tidal volume (TV), respiration rate (RR), and positive end expiratory pressure (PEEP). The displayed machine setting trends include machine mode (herein, the machine is controlled in a volume control ventilation (VCV) mode). The displayed trends may be customized by the user, for example by selecting the edit button 608 and deleting displayed trends or adding trends to be displayed (e.g., from a list of possible patient monitoring parameter trends). While each of the trends shown in FIG. 6 are formatted as trend lines, in some embodiments one or more of the patient monitoring parameter trends may be displayed in a different format, such as a series of bar graphs.

As explained above, the trends GUI 600 may include a timeline when prompted. In some embodiments, the timeline may be displayed in response to a first user input, such as a single touch input entered to the display along the time points displayed above the set of trends 610. While the timeline may show respective values for each of the patient monitoring parameters at a single point in time, it may be beneficial for the user to view changes in the patient monitoring parameters in a more quantifiable manner (e.g., rather than having to guess at an overall trend based on the trend lines). Accordingly, a set of timelines may be displayed in response to a second user input, such as two concurrent touch inputs made to the display at the set of trends 610 (e.g., two fingers touching the display at the same time). A respective timeline may then be displayed at times corresponding to the location of the touch inputs, as shown in FIG. 7.

Figure 7:
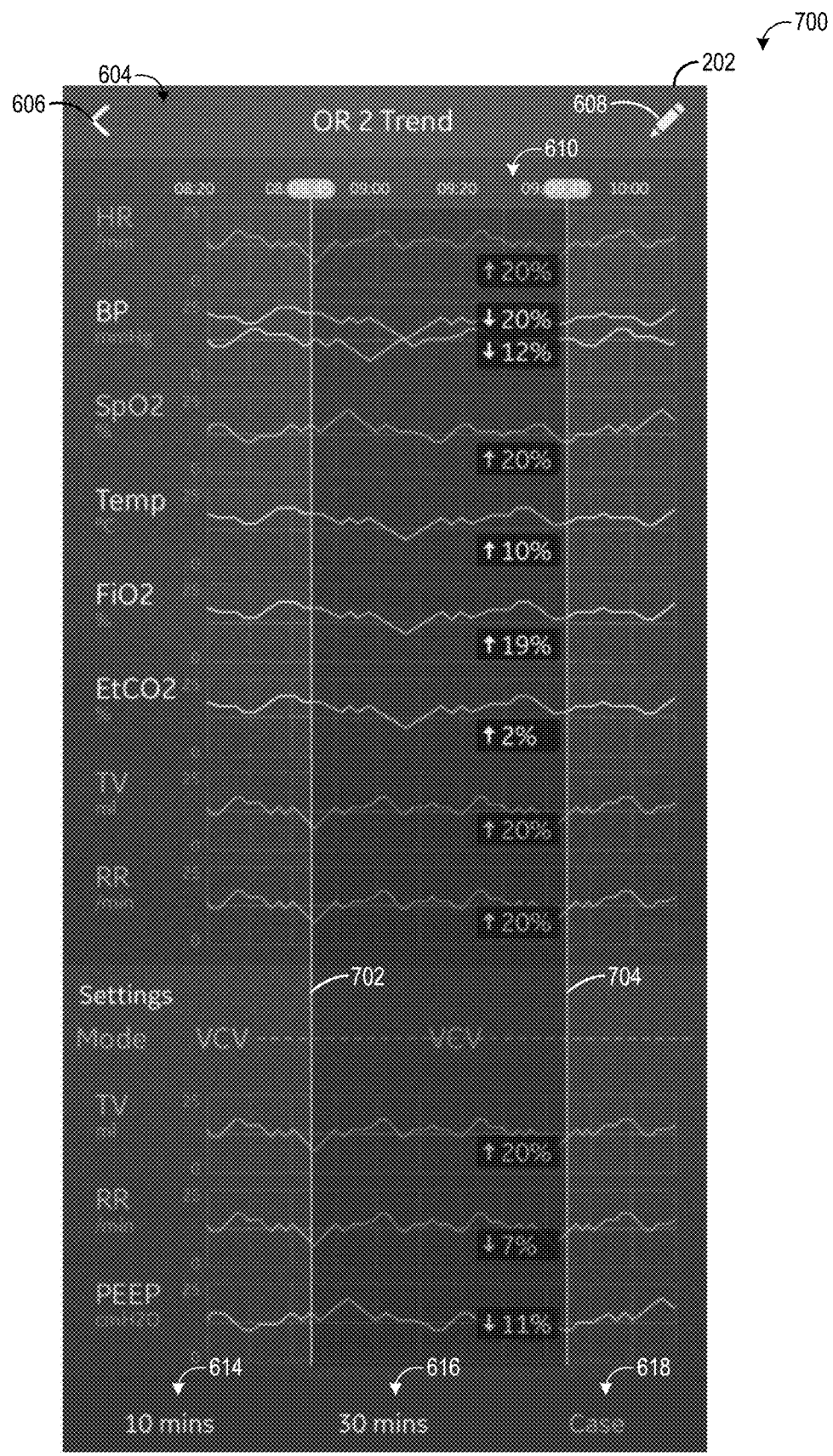

FIG. 7 shows a view 700 of the trends GUI 600 of FIG. 6 with two timelines displayed on the set of trends 610. The timelines include a first timeline 702 and a second timeline 704. First timeline 702 may be positioned at a location corresponding to a first touch input (e.g., at 08:45) and second timeline 704 may be positioned at a location corresponding to a second touch input (e.g., at 09:45) of two concurrent touch inputs. The two timelines may be moved in response to a third touch input, such as the two timelines being brought closer together or moved further apart in response to concurrent touch inputs to the two timelines followed by dragging of the timelines closer together or further apart.

When the two timelines are displayed as shown in FIG. 7, rather than displaying corresponding instantaneous values for each displayed patient monitoring parameter (as shown in FIG. 6), an overall change in each patient monitoring parameter over the duration between the first timeline 702 and the second timeline 704 is displayed. For example, an overall change in heart rate may be determined from 08:45 to 09:45 (e.g., an increase of 20%) and displayed next to the trend line for heart rate.

As explained above with respect to FIG. 2, single-patient GUI 200 includes an insights tile 302, a message tile 304, and an alarms tile 306, where notifications regarding insights, messages, and alarms, respectively, specific to the patient are displayed. When an insight or alarm has been triggered, or when a message has been received, the user may select the appropriate tile to cause the insight, message, or alarm to be displayed. FIGS. 8-10 show example views of single-patient GUI 200 where the insights tile is selected, the alarm tile is selected, and the messages tile is selected, respectively.

Referring first to FIG. 8, it shows an insights view 800 of single-patient GUI 200 displayed on display device 202 where the insights tile 302 indicates that two insights have been triggered for the patient (e.g., located in OR 2). User selection of the insights tile 302 (shown schematically by hand 802) causes an insights banner 804 to be displayed. The insights banner 804 may indicate the insight(s) that have been triggered for the patient, such as an oxygen/medical gas flow via the ventilator to the patient that has been greater than 6 pounds a minute for more than 10 minutes (as shown in FIG. 8). In the example shown in FIG. 8, the insights banner 804 is showing information related to a first insight. If additional insights have been triggered for the patient, user input (e.g., a touch input swiping the insights banner) may cause the additional insight(s) to be displayed at the insights banner 804. Further, a visual notification of the additional insights may be displayed, such as the two dots shown above the insights banner 804 in FIG. 8.

Additionally, user selection of the insights tile 302 causes action buttons to be displayed, including an acknowledge button 806 and a snooze button 808. When selected, the acknowledge button 806 may indicate to the supervisory application that the user has seen the insight, and thus further notification of the insight via the current single-patient GUI 200 may be dispensed with. When selected, the snooze button 808 may indicate to the supervisory application that the user has seen the insight, but would like to be reminded of the insight again after a threshold time period has elapsed (e.g., 10 minutes).

In some embodiments, patient monitoring information relevant to the insight may be displayed along with the insights banner 804. In the example shown in FIG. 8, a set of trends 810 is displayed below the insights banner 804. The set of trends 810 includes a trend line 812 for the oxygen/medical gas flow referenced in the insight as well as trend lines for parameters related to the oxygen/medical gas flow, shown here as including the anesthesia phase, anesthesia concentration (e.g., Sev %), and patient oxygen saturation (e.g., O2%). Similar to the other sets of trends explained above, a timeline 814 may be displayed in response to user input (e.g., a touch input to a selected time point of the set of trends 810).

Referring to FIG. 9, it shows an alarm view 900 of single-patient GUI 200 displayed on display device 202 where the alarm tile 306 indicates that an alarm has been triggered for the patient (e.g., located in OR 2). User selection of the alarm tile 306 (shown schematically by hand 902) causes an alarm banner 904 to be displayed. The alarm banner 904 may indicate the alarm(s) that have been triggered for the patient, such as SpO2 being below a threshold value (as shown in FIG. 9). In the example shown in FIG. 9, the alarm banner 904 is showing information related to a first alarm. If additional alarms have been triggered for the patient, user input (e.g., a touch input swiping the insights banner 804) may cause the additional alarm(s) to be displayed at the alarm banner 904.

Additionally, user selection of the alarm tile 306 causes action buttons to be displayed, including an acknowledge button and a snooze button, similar to the acknowledge and snooze buttons presented above with respect to FIG. 8. Also shown in FIG. 9 is a settings button 906 that may be displayed when the alarm tile 306 is selected. When selected, the settings button 906 may cause display of settings/system alarms menu where the user may customize the alarms, e.g., delete existing alarms, add new alarms, and/or edit existing alarms.

Referring to FIG. 10, it shows a message view 1000 of single-patient GUI 200 displayed on display device 202 where the message tile 304 indicates that a consultation for the patient (e.g., located in OR 2) has been requested by another care provider (e.g., a subordinate care provider or other care provider located in the room with the patient). User selection of the message tile 304 (shown schematically by hand 1002) causes a message banner 1004 to be displayed. The message banner 1004 may indicate the nature of the message that has been received, such as the consultation being requested. In the example shown in FIG. 10, the message banner 1004 is showing that a consultation has been requested. However, other types of messages may be received, such as SMS-based text messages from another care provider requesting a particular type of assistance, asking questions, sharing details of current patient status, and so forth. In such examples, the message banner 1004 may indicate that a text message has been received from a care provider currently caring for that patient. Further, if additional messages have been received that are related the patient, user input (e.g., a touch input swiping the message banner) may cause the additional messages to be displayed at the message banner 1004.

Additionally, user selection of the message tile 304 and/or of message banner 1004 may cause a message thread 1006 to be displayed, where messages sent and received with the care provider who sent the triggering message may be displayed. Also shown in FIG. 9 is a message input box 1008 where the user may enter text or voice input in order to send a message to the requesting care provider. For example, as shown, the user may respond with an estimated amount of time for the user to be available for the requested consultation.

Thus, FIGS. 2-10 show various views of a single-patient GUI that may be displayed on a care provider device as part of the supervisory application. Via the single-patient GUI, a user (such as a supervising anesthesiologist or other supervising care provider) may view real-time patient monitoring parameters for a specific patient, which may include physiological parameters of the patient and/or machine settings for one or more therapy devices being used to perform a procedure on the patient. Further, via the single-patient GUI, the user may view trends for one or more patient monitoring parameters for the specific patient over time, as well as view and respond to alarms, insights, and/or messages specific to the patient. The user may customize which patient monitoring parameters to view, which trends to view, and which alarms and insights are to be triggered/received for the patient. Further, the user may select from two or more default layouts for how the single-patient GUI is to be configured visually and/or customize the layout of the single-patient GUI (e.g., square tiles arranged in an array, such as shown in FIG. 2, rectangular tiles arranged according to category as shown in FIG. 4A, etc.).

The supervisory application may also enable the user to view multi-patient GUIs where a limited amount of information is viewed for a plurality of different patients. FIGS. 11-16 show example multi-patient GUIs that may be displayed as part of the supervisory application according to embodiments of the present disclosure.

Figure 11:
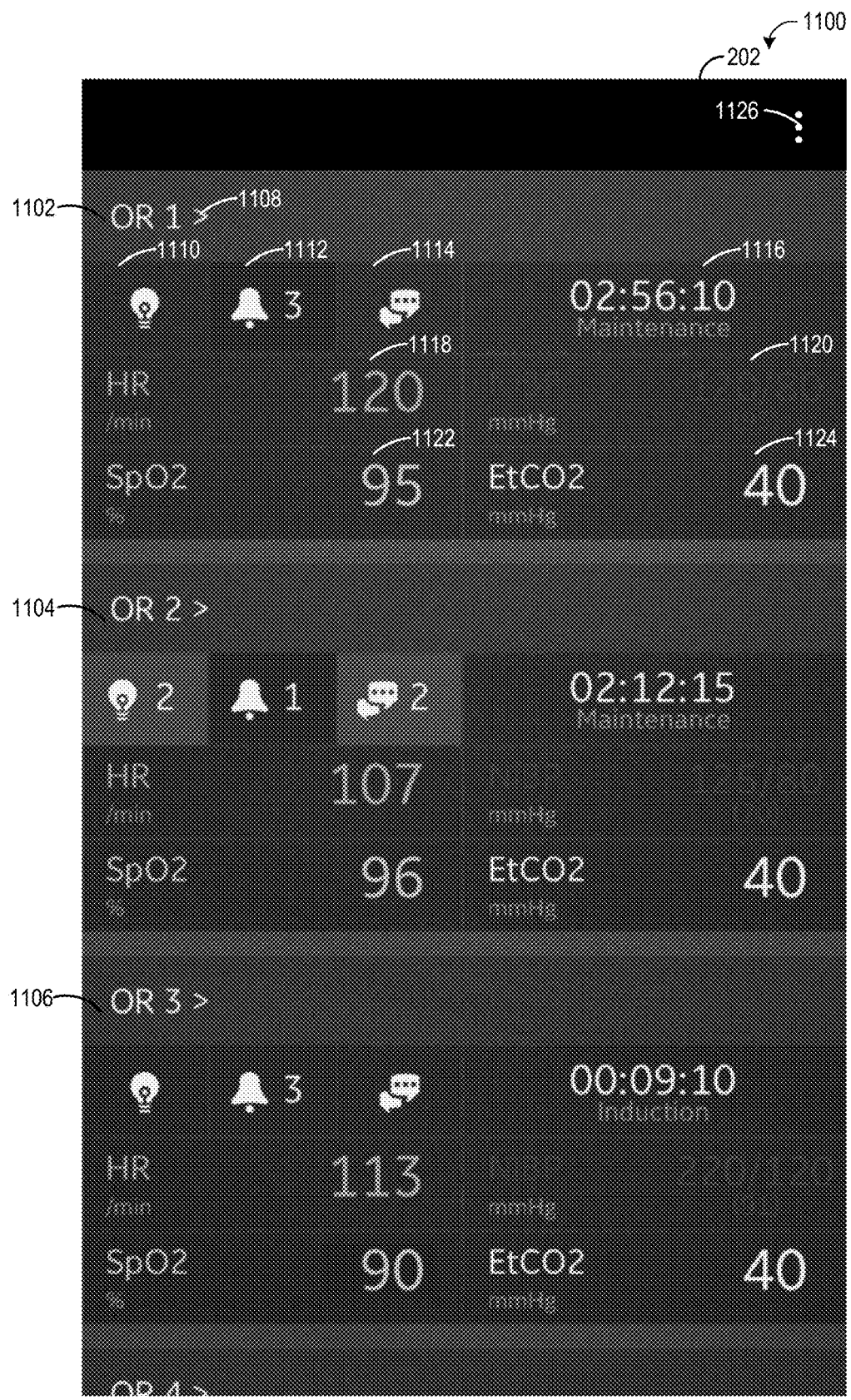
FIGS. 11-15 show the display device displaying various views of a multi-patient graphical user interface generated via the supervisory application.

FIG. 11 shows a multi-patient GUI 1100 displayed on display device 202. Multi-patient GUI 1100 may be displayed in response to launching the supervisory application and/or in response to selection of a back button from a single-patient GUI. Multi-patient GUI 1100 may display information for each of a plurality of patients being overseen by the user of the care provider device associated with display device 202, such as a supervising care provider, as explained above with respect to FIG. 2. As shown in FIG. 11, information for a first patient, a second patient, and a third patient is shown. Information for additional patients may be viewed by scrolling up or down. Each patient may be identified by a patient banner, such as patient banner 1102 (showing that information for the patient in OR 1 is being shown), patient banner 1104 (showing that information for the patient in OR 2 is being shown), and patient banner 1106 (showing that information for the patient in OR 3 is being shown). Each patient banner may include a forward button, such as forward button 1108, or other suitable action button that, when selected, may cause display of the single-patient GUI for that patient. For example, if the forward button in patient banner 1104 is selected, single-patient GUI 200 may be displayed.

A limited amount of patient monitoring information is displayed for each patient via the multi-patient GUI 1100. For example, as shown for the first patient (e.g., located in OR 1), an insights tile 1110, an alarm tile 1112, and a message tile 1114 may all be displayed, similar to the insights tile, the alarm tile, and the message tile of the single-patient GUI 200. However, due to the limited space available, each of the insights tile 1110, alarm tile 1112, and message tile 1114 may be smaller relative to the tiles in the single-patient GUI 200. As appreciated by alarm tile 1112, when an alarm has been triggered for that patient, a number may be displayed in the alarm tile 1112, indicating the number of alarms that have been triggered for that patient. Similar numbers may be displayed in the insights tile 1110 and message tile 1114 when insights or messages, respectively, are triggered or received for that patient. Further, the tile (e.g., alarm tile 1112) may have a different visual appearance when an insight, alarm, or message is triggered or received for the patient. For example, the tile may change in color, become highlighted, or otherwise change in visual appearance to signify the presence of an insight, alarm, or message. An insights tile, an alarm tile, and a message tile may be displayed for each patient.

The patient information that is displayed via the multi-patient GUI 1100 may include a procedure timing tile, such as procedure timing tile 1116, that indicates the phase of the procedure (e.g., phase of anesthesia delivery, such as maintenance) and the current duration of the procedure. Further, as shown in FIG. 11, a plurality of patient monitoring parameter tiles may be displayed for each patient, such as a first patient monitoring parameter tile 1118 (showing heart rate for the first patient), a second patient monitoring parameter tile 1120 (showing blood pressure), a third patient monitoring parameter 1122 (showing SpO2), and a fourth patient monitoring parameter 1124 (shown EtCO2). In the example shown in FIG. 11, for each patient, the same patient monitoring parameters may be displayed. The patient monitoring parameters that are displayed via the multi-patient GUI 1100 may be customized by the user, as will be explained below.

Figure 12:
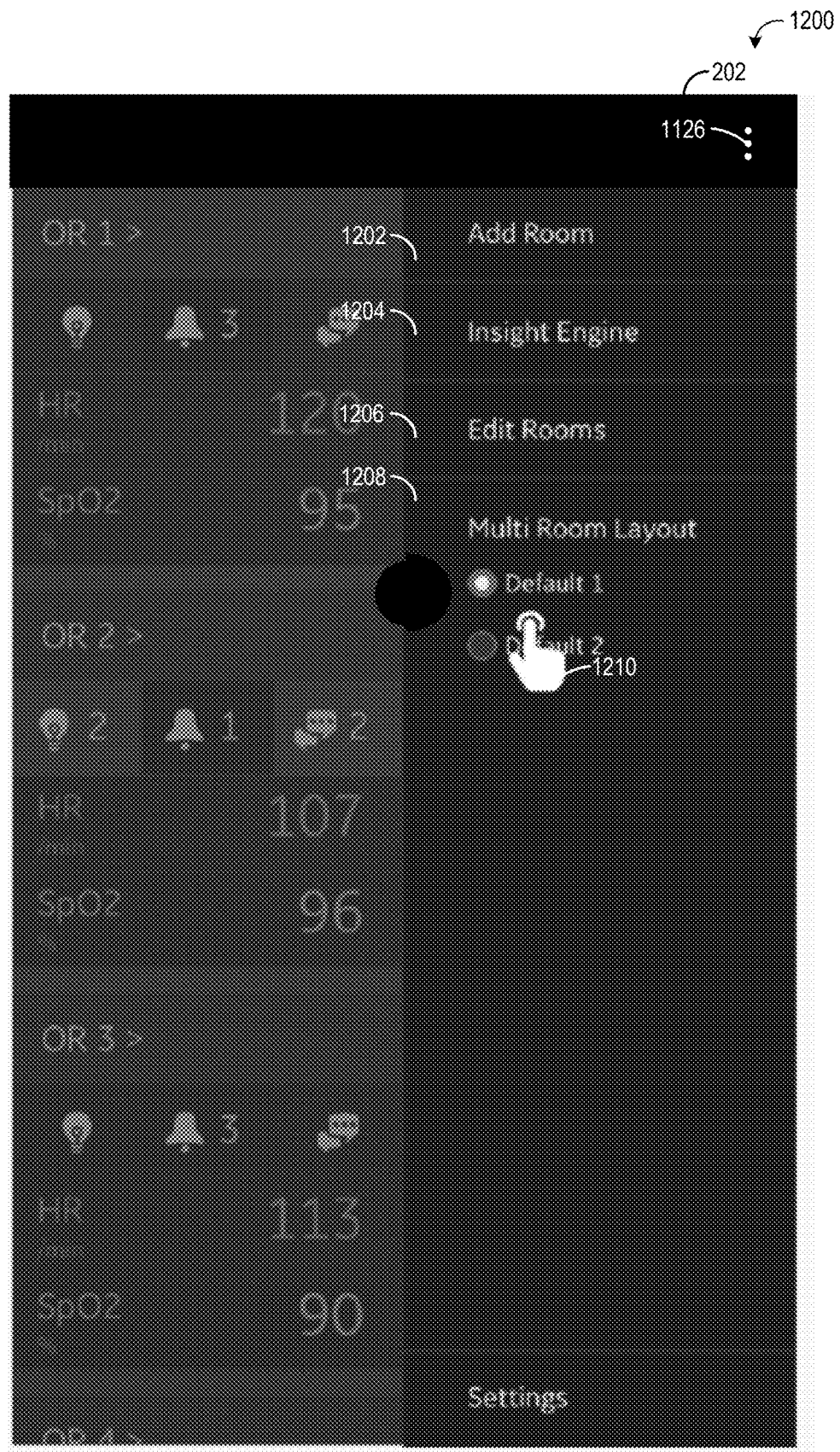

Multi-patient GUI 1100 further includes a menu button 1126. When selected, menu button 1126 may cause a context menu to be displayed, via which various aspects of the multi-patient GUI may be adjusted. FIG. 12 shows an example context menu 1200 that may be displayed on display device 202, for example in response to user selection of the menu button 1126. Context menu 1200 may be similar to context menu 500 of FIG. 5, and thus includes a plurality of control buttons that may trigger different actions. For example, the context menu 1200 may include an add room button 1202, an insights engine button 1204 (which may trigger display of an insights GUI, as will be described in more detail below with respect to FIGS. 17-20), an edit rooms button 1206, and a room layout set of buttons 1208. The room layout set of buttons 1208 may include a button for each different possible layout for how the multi-patient GUI is configured for display. For example, a first layout (e.g., corresponding to multi-patient GUI 1100) may be displayed when the "Default 1" button is selected and a second layout (e.g., corresponding to multi-patient GUI 1300 described below) may be displayed when the "Default 2" button is selected. While not shown in FIG. 12, one or more additional layouts (which may be layouts customized by the user) may be displayed when a "Customize" button is displayed. Additionally, context menu 1200 may include a settings button (shown at the bottom of the context menu) that may cause a settings GUI to be displayed, when selected. Via the settings GUI, various settings of the supervisory application may be adjusted, such as language, notification settings (e.g., sound, vibration), room set-up, add new room, and system alarms. For example, in the system alarms page, preset alarms (e.g., for heart rate, SpO2, and blood pressure) may be turned on or off, and new alarms may be set, at least in some examples.

FIG. 12 shows a user input being entered (shown schematically by hand 1210) to switch from the first layout of multi-patient GUI 1100 to a second layout of multi-patient GUI 1300 of FIG. 13. As a result of the user input, multi-patient GUI 1300 is displayed, as shown in FIG. 13. Multi-patient GUI 1300 may include less information for each patient than multi-patient GUI 1100, and thus more patients may be viewed on one screen. As shown in FIG. 13, multi-patient GUI 1300 includes a plurality of patient banners, such as patient banner 1302 (showing that information for the patient in OR 1 is being shown), patient banner 1304 (showing that information for the patient in OR 2 is being shown), and patient banner 1306 (showing that information for the patient in OR 3 is being shown). Each patient banner may include a forward button, such as forward button 1308, or other suitable action button that, when selected, may cause display of the single-patient GUI for that patient. For example, if the forward button 1301 is selected, single-patient GUI 200 may be displayed.

A limited amount of patient monitoring information is displayed for each patient via the multi-patient GUI 1300. For example, as shown for the first patient (e.g., located in OR 1), an insights tile 1310, an alarm tile 1312, and a message tile 1314 may all be displayed, similar to the insights tile, the alarm tile, and the message tile of the single-patient GUI 200. However, due to the limited space available, each of the insights tile 1310, alarm tile 1312, and message tile 1314 may be smaller relative to the tiles in the single-patient GUI 200. As appreciated by alarm tile 1312, when an alarm has been triggered for that patient, a number may be displayed in the alarm tile, indicating the number of alarms that have been triggered for that patient. Similar numbers may be displayed in the insights tile and message tile when insights or messages, respectively, are triggered or received for that patient. Further, the tile (e.g., alarm tile 1312) may have a different visual appearance when an insight, alarm, or message is triggered or received for the patient. For example, the tile may change in color, become highlighted, or otherwise change in visual appearance to signify the presence of an insight, alarm, or message. An insights tile, an alarm tile, and a message tile may be displayed for each patient. The patient information that is displayed via the multi-patient GUI 1300 may include a procedure timing tile, such as procedure timing tile 1316, that indicates the phase of the procedure (e.g., phase of anesthesia delivery, such as maintenance) and the current duration of the procedure. Multi-patient GUI 1300 also includes a menu button 1318 that may cause context menu 1200 to be displayed when selected.

Figure 14:
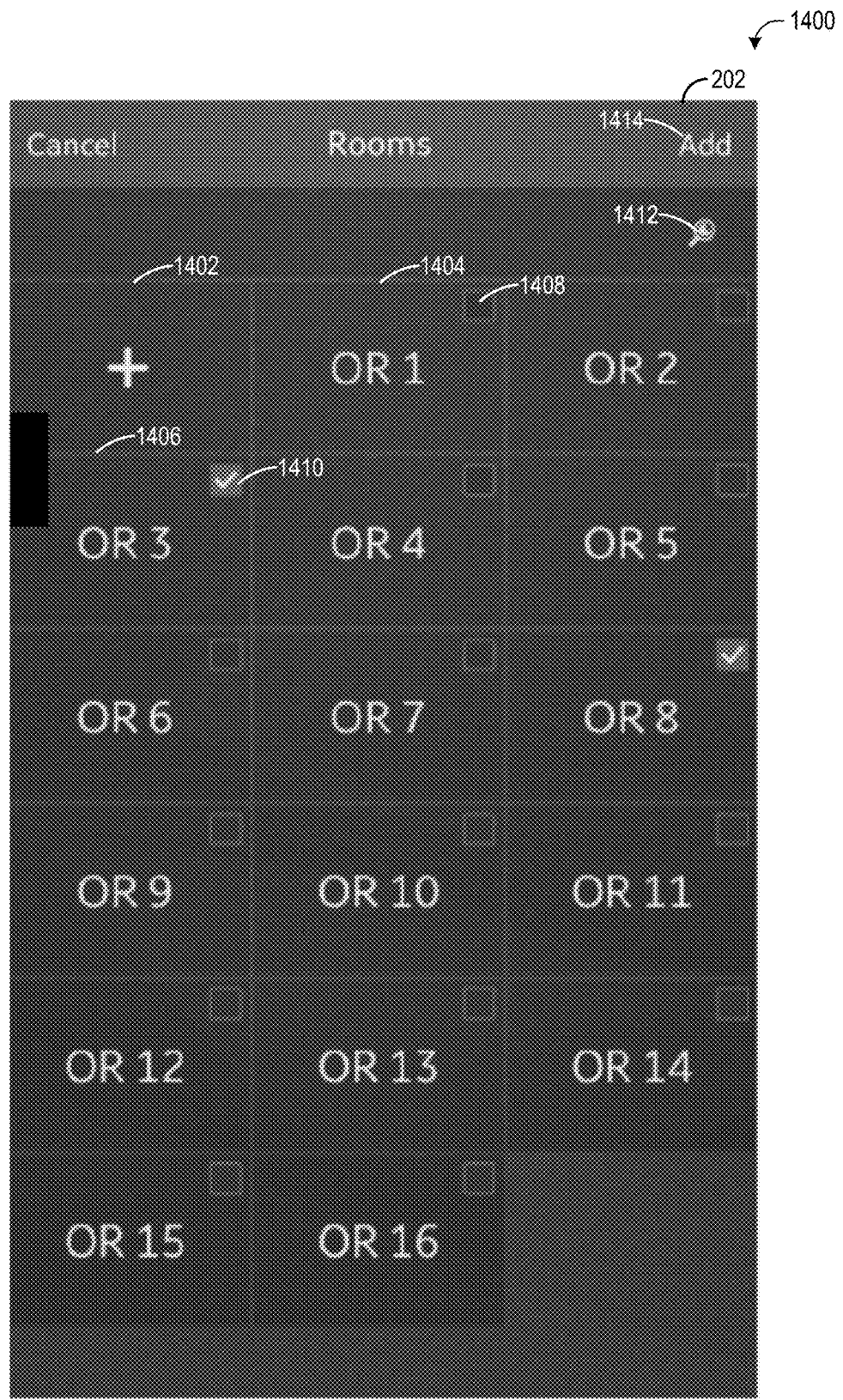

Returning to FIG. 12, as explained above, the context menu 1200 includes an add room button 1202. Selection of the add room button 1202 causes display of an add room page, such as the add room page 1400 shown in FIG. 14. As shown in FIG. 14, the add room page 1400 includes a plurality of square tiles arranged in an array, with the tiles indicating the available rooms which can be added to the multi-patient GUI 1100 or 1300. A first tile 1402 may include a new room button. When selected, the new room button may cause display of rooms not already shown in the add room page 1400. Likewise, the add room page 1400 includes a search button 1412 that may be selected to cause a search box to be displayed so that the user may search for rooms not shown on add room page 1400.

A second tile 1404 shows that OR 1 is available to be added to the multi-patient GUI and a third tile 1406 shows that OR 3 is already added (or has been selected to be added) to the multi-patient GUI. The second tile 1404 includes an unchecked box 1408, signifying that OR 1 has not been added to the multi-patient GUI. User selection of the unchecked box 1408 causes OR 1 to be added to the multi-patient GUI. The third tile 1406 includes a checked box 1410, signifying that OR 3 is already added or is chosen to be added to the multi-patient GUI. User selection of the checked box 1410 will cause OR 3 to be removed from the multi-patient GUI. Once desired rooms have been added or removed, user selection of an add button 1414 will save the added or removed rooms and update the multi-patient GUI accordingly. Changes to the multi-patient GUI, such as adding or removing rooms as explained above, may be saved in the settings/configuration database of the edge device, as explained above with respect to FIG. 1B.

Figure 15:
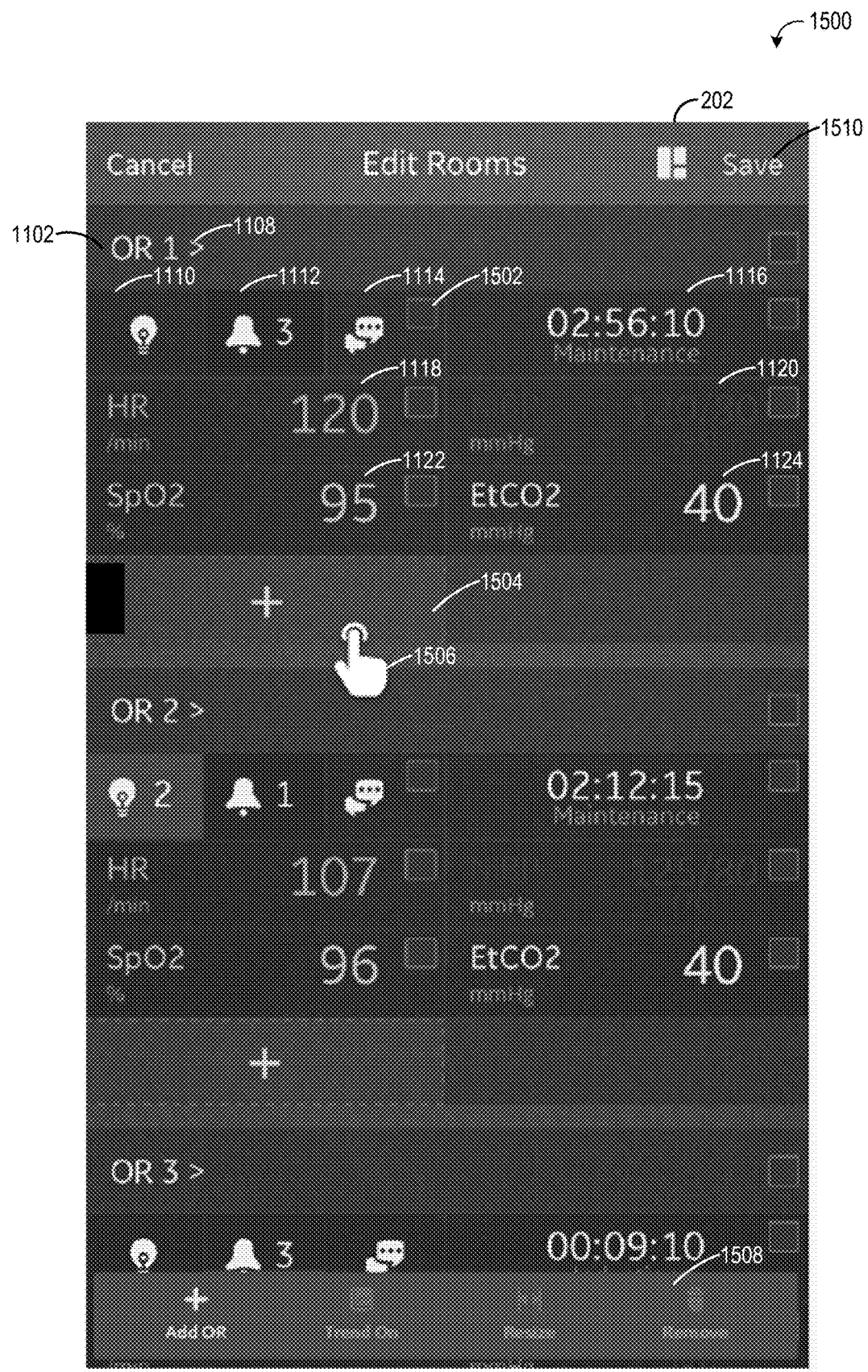

Returning again to FIG. 12, when the edit rooms button 1206 is selected, the multi-patient GUI (in the current layout) may be displayed with selectable control buttons displayed for each currently-selected patient monitoring parameter. FIG. 15 shows an example edit rooms page 1500 that may be displayed in response to selection of the edit rooms button 1206. The edit rooms page 1500 includes a view similar to multi-patient GUI 1100, but also includes selectable control buttons, such as button 1502, within each patient monitoring parameter tile (other than the insights tile and alarm tile, which may not be removed by the user, at least in some examples). User input to a control button may toggle that patient monitoring parameter between being selected (and thus included in the GUI) and not selected (and thus not included in the GUI). Further, additional patient monitoring parameter(s) may be added via an add control button, such as add control button 1504.

Additionally, the edit rooms page 1500 may include an edit banner 1508 that may include various edit functionalities, such as adding a room, turning on a trend for a particular patient monitoring parameter, resizing a patient monitoring parameter tile, and removing a patient monitoring parameter tile. For example, when the user selects a control button, such as the control button that is within tile 1118, the "trend on," "resize," and "remove" buttons may become selectable. By selecting the "trend on" button, a trend for that patient monitoring parameter may be shown, in addition or alternative to the most-recently obtained value for that patient monitoring parameter. When the "resize" button is selected, the tile for that patient monitoring parameter may resized (e.g., made larger or smaller, which may also cause more or less information associated with that patient monitoring parameter to be displayed). When the "remove" button is selected, the tile for that patient monitoring parameter may be removed. Once the user has made desired changes to the patient monitoring parameters shown for each patient, the user may select a save button 1510, which will save and apply the changes to the multi-patient GUI.

Figure 16:
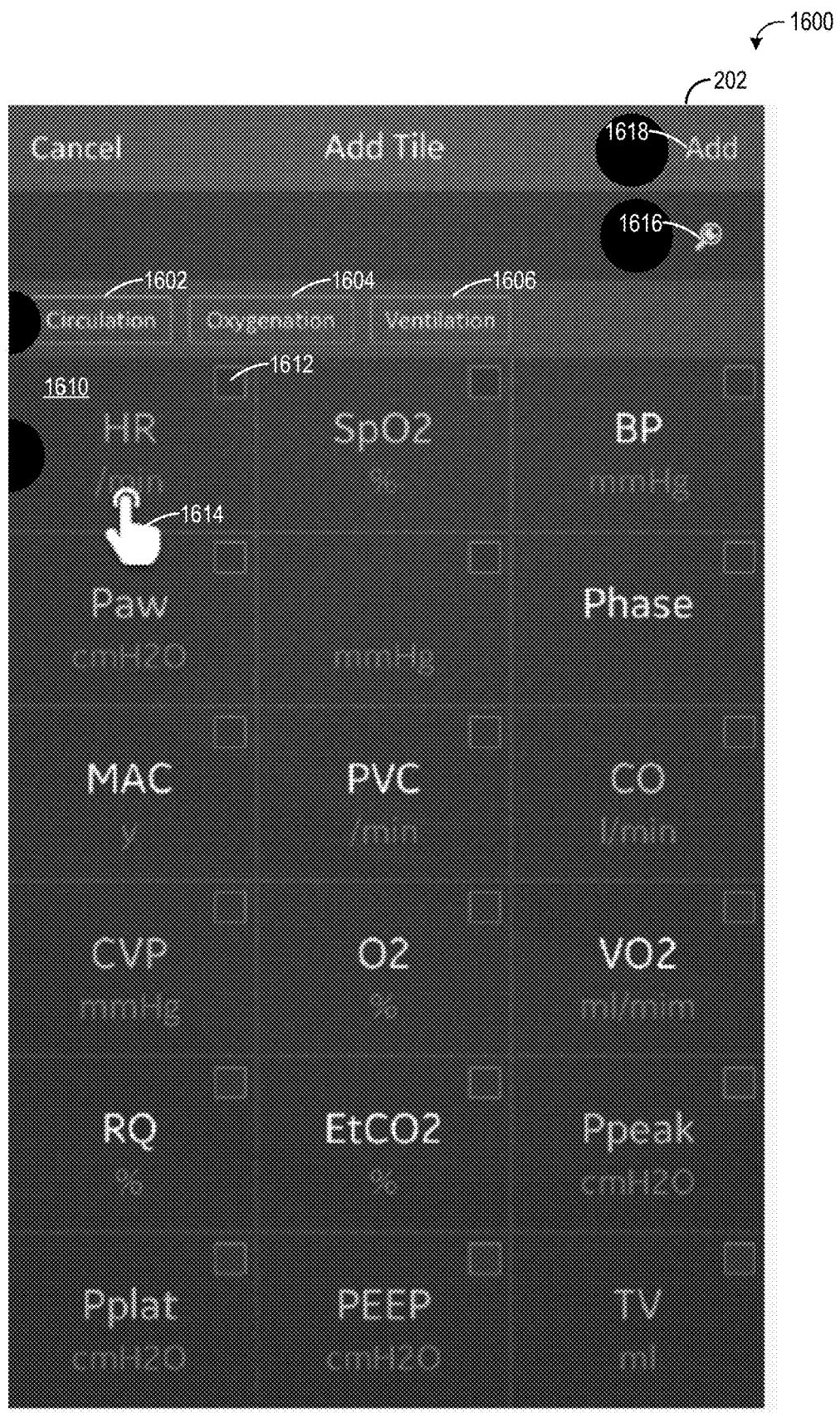
FIGS. 16-20 show the display device displaying various views of an insight graphical user interface generated via the supervisory application.

In the example shown in FIG. 15, a touch input is being entered to the add control button 1504 (shown schematically by hand 1506). As a result, an add tile page is displayed, via which the user may choose patient monitoring parameter tiles to add for the selected patient/room. FIG. 16 shows an example add tiles page 1600. The add tiles page 1600 may include a plurality of patient monitoring parameter buttons arranged in an array. The patient monitoring parameter buttons may each be associated with a patient monitoring parameter. For example, a first patient monitoring parameter button 1610 may be specific to heart rate. The patient monitoring parameter buttons may be organized and displayed by category, which may aid the user in quickly navigating through the plurality of possible patient monitoring parameters to add to the GUI. For example, as shown in FIG. 16, a circulation button 1602 has been selected, causing patient monitoring parameters related to circulation to be displayed on the add tiles page 1600. The add tiles page 1600 also includes an oxygenation button 1604 and a ventilation button 1606, which when selected cause display of patient monitoring parameters related to oxygenation and ventilation, respectively. The add tiles page 1600 also includes a search button 1616 that may cause a search box to be displayed, via which the user may enter search terms to find a desired patient monitoring parameter.

Each patient monitoring parameter button may include a box, such as box 1612. User input to the patient monitoring parameter button may cause the associated box to become checked/selected (if not selected) or unchecked/unselected (if selected). For example, user input to button 1610 (shown by hand 1614) may cause box 1612 to become checked, indicating that heart rate is being chosen to be added as a patient monitoring parameter to be displayed on the GUI. Once the user has made desired edits (e.g., adding desired patient monitoring parameters), an add button 1618 may be selected, causing the selected patient monitoring parameter(s) to be added to the appropriate GUI.

While FIGS. 15 and 16 were described above as being specific to the multi-patient GUI (such as multi-patient GUI 1100), it is to be understood that similar edit rooms and add tiles pages may be displayed when customizing a single-patient GUI. For example, an edit rooms page may be displayed in response to user selection of edit room button 506 of context menu 500, with the edit rooms page including similar functionality as the edit rooms page 1500 (e.g., control buttons to remove, resize, or add trends to patient monitoring parameters that are currently being displayed and control buttons to add patient monitoring parameter tiles).

As explained previously, the supervisory application may apply insights, which may be similar to alarms but may be based on multiple patient monitoring parameters, may be applied conditionally, and so forth, which may provide a more nuanced approach to alerting care providers when patient condition has changed. The insights may include functions that are applied on the received medical device data to determine a current patient status (not otherwise easily determined from viewing individual patient monitoring parameters), predict a future patient status, determine a current phase or portion of a medical procedure, and other applications. The functions may include simple threshold-based comparisons, including one or more patient monitoring parameters and/or limited by a scope, and also may include more complex models and/or algorithms to analyze the received medical device data. As such, the insights described herein may also be referred to as functions.

FIGS. 17-20 show example views of an insights GUI that may be displayed on a care provider device as part of supervisory application 44. Via the insights GUI, a user may be able to define and edit insight rules to be applied to patients being monitored by the user, search for and apply insights created by other users, whether locally (e.g., at the same medical facility) or globally, and view insights that have been triggered for patients being monitored by the user, as explained below.

FIG. 17 shows a first view 1700 of an insights GUI being displayed on display device 202. The insights GUI, and in some examples specifically the first view 1700, may be displayed in response to user selection of an insight engine button from a context menu (e.g., insights engine button 504 of FIG. 5 and/or insights engine button 1204 of FIG. 12) of the supervisory application, or other suitable user input. Via the first view 1700, the user may be able to browse or search for public/shared insights. For example, the first view 1700 includes a search box 1702. The user may enter search terms into the search box 1702, and the supervisory application may display any relevant insights in response.

The first view 1700 includes a first section of insights, referred to as the "quick picks" section, where insights that have been developed by other users may be browsed. For example, a first insight tile 1704 is displayed in the quick picks section. The first insight tile 1704 may include an indication of the insight rules (e.g., trigger an insight if total flow is greater than 6 pounds a minute for 10 minutes) for a first insight. The first insight tile 1704 may also include an indication of how many users have applied the first insight. The first view 1700 may include four insight tiles displayed as part of the quick picks section, but other numbers of insight tiles are possible. Further, additional insight tiles created by other users may be viewed by selecting the "view all" button within the quick picks section.

The insights that are displayed as part of the quick picks section may be generated by all users, whether locally or at other medical facilities. In some examples, the insights in the quick picks section may be organized by popularity, such that the insights that have been applied by the most users may be displayed first. However, other methods for organizing and presenting the insights are possible, such as by patient monitoring parameter.

The first view 1700 further includes a second insights section, referred to as a "hospital insights" section, where insights created by users at the same medical facility may be browsed. For example, the hospital insights section includes a second insight tile 1706, where insight rules for a second insight are displayed, along with the number of users applying the insight and the author of the insight. The first view 1700 may include four insight tiles displayed as part of the hospital insights section, but other numbers of insight tiles are possible. Further, additional insight tiles created by other users at the medical facility may be viewed by selecting the "view all" button within the hospital insights section.

The insights that are displayed as part of the hospital insights section may be generated only by users that attend to patients at the medical facility where the user interacting with the first view 1700 (e.g., the user of the care provider device associated with display device 202) attends to patients. In this way, the user may browse insights from trusted sources that conform to any internal standards or guidelines applied by the medical facility or other administrative organization. In some examples, the insights in the hospital insights section may be organized by popularity, by patient monitoring parameter, by date the insight was created, etc.

The first view 1700 includes a plurality of control buttons displayed along a bottom of the first view 1700. The control buttons include a discover button 1708, an activity button 1710, and a my insights button 1712. When the discover button 1708 is selected, the first view 1700 may displayed, which may enable the user to discover/search for new insights. When the activity button 1710 is selected, a second view of the insights GUI may be displayed where a list of the user's selected insights, and in some examples alarms, that have been applied to a patient may be viewed. When the my insights button 1712 is selected, a third view of the insights GUI may be displayed where the user may add, remove, and edit insights.

Figure 18:
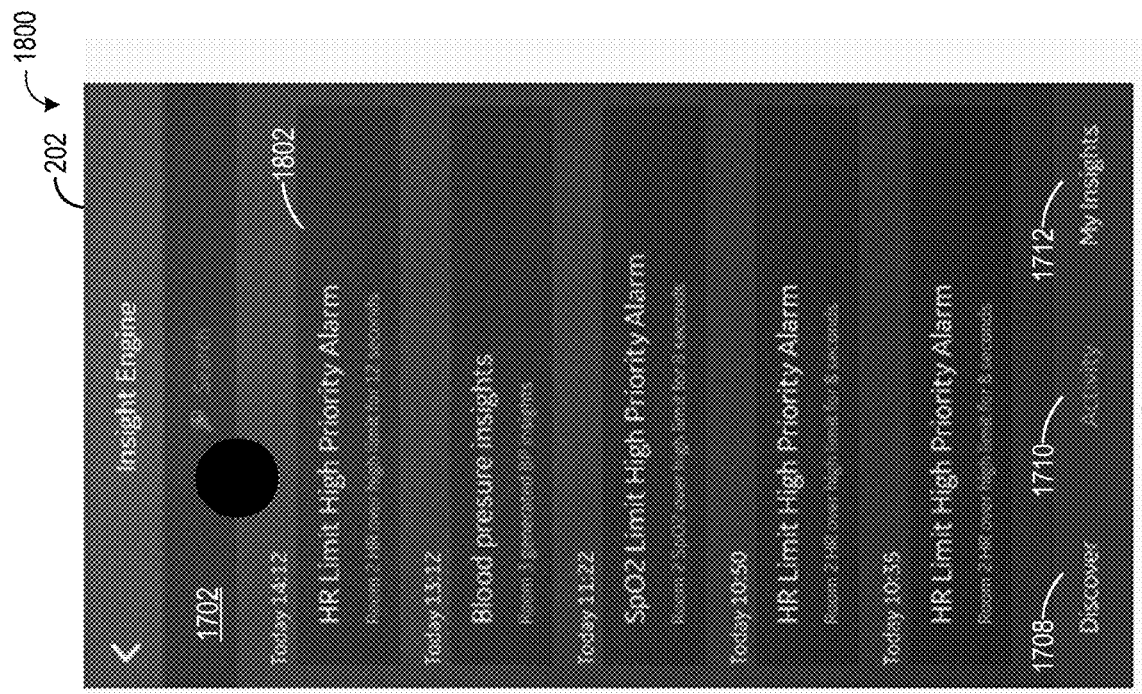

FIG. 18 shows an example of a second view 1800 of the insights GUI that may be displayed in response to user selection of an activity button, such as activity button 1710. The second view 1800 includes the search box 1702, the discover button 1708, the activity button 1710, and the my insights button 1712, similar to the first view 1700. The second view includes a list of insights and alarms that have been applied to one or more patients. The insights and alarms that are listed in the second view 1800 may include insights and alarms chosen by the user to be applied to the patients being monitored by the user, that were applied to a patient during the course of a procedure where the patient was being monitored/treated by one or more of the medical devices described herein. For example, a first applied insight tile 1802 is displayed in the first view 1800. The first applied insight tile 1802 includes an indication of the rules of the insight/alarm that was applied, herein a heart rate limit high priority alarm. The tile 1802 further includes an indication of when the insight/alarm was triggered (e.g., today at 14:12), on which patient (e.g., the patient in room 2), and for how long the triggering condition persisted (e.g., for 12 seconds).

The applied insights/alarm tiles may be organized chronologically, reverse-chronologically, or in another suitable manner.

Figure 19:

FIG. 19 shows an example of a third view 1900 of an insights GUI that may be displayed in response to user selection of a my insights button (e.g., my insights button 1712). The third view 1900 includes the discover button 1708, the activity button 1710, and the my insights button 1712, similar to the first view 1700 and second view 1800. In the third view 1900, a list of all alarms and insights saved/selected by the user are shown, including alarms/insights that are selected to be applied and alarms/insights that are currently not being applied. For example, a first tile 1902 includes an indication of the rules of the alarm/insight (e.g., SpO2 high alarm) and an indication of which patients that alarm/insight is be applied to (e.g., all patients). The tile 1902 also includes an on/off button 1904 showing that the alarm/insight is on, which indicates that the alarm/insight will be applied with patient monitoring parameters meeting the alarm/insight rules. The third view 1900 includes a second tile 1906 that includes alarm/insight rules (e.g., arterial mean pressure high alarm) and who the alarm/insight applies to (e.g., all). The second tile 1906 includes an on/off button 1908 showing that the alarm/insight is no longer being applied.

If the user selects an alarm or insight listed in the third view 1900, or if the user selects an add alarm/insight button 1910, a fourth view 2000 of the insights GUI may be displayed, as shown in FIG. 20. Via the fourth view 2000, aspects of the alarm/insight may be edited. For example, the fourth view 2000 includes an information tile 2002 for the selected insight/alarm, which indicates the insight rules (e.g., if heart rate is greater than 150 beats/minute for 5 minutes during maintenance phase), priority level (e.g., level 1), and who the insight is to be applied to (e.g., all rooms). The tile 2002 includes a toggle button 2004 that the user may move to turn the insight on (as shown) or off. Further, the fourth view 2000 includes an edit button 2006 and a delete button 2008. When selected, the edit 2006 button may cause display of an edit page, where aspects of the insight may be changed. When selected, the delete button 2008 may cause the selected insight to be removed from the user's list of insights (e.g., the insight will not be shown in the third view 1900). In some examples, the fourth view 2000 may include a share insight button 2010 that may change the privacy settings of the displayed insight from private to public when selected. For example, the insight displayed in FIG. 20 is marked as private, but selection of share insight button 2010 may switch the privacy setting to public. Once the privacy setting is changed to public, other users may view and apply the insight, if desired.

Figure 21:
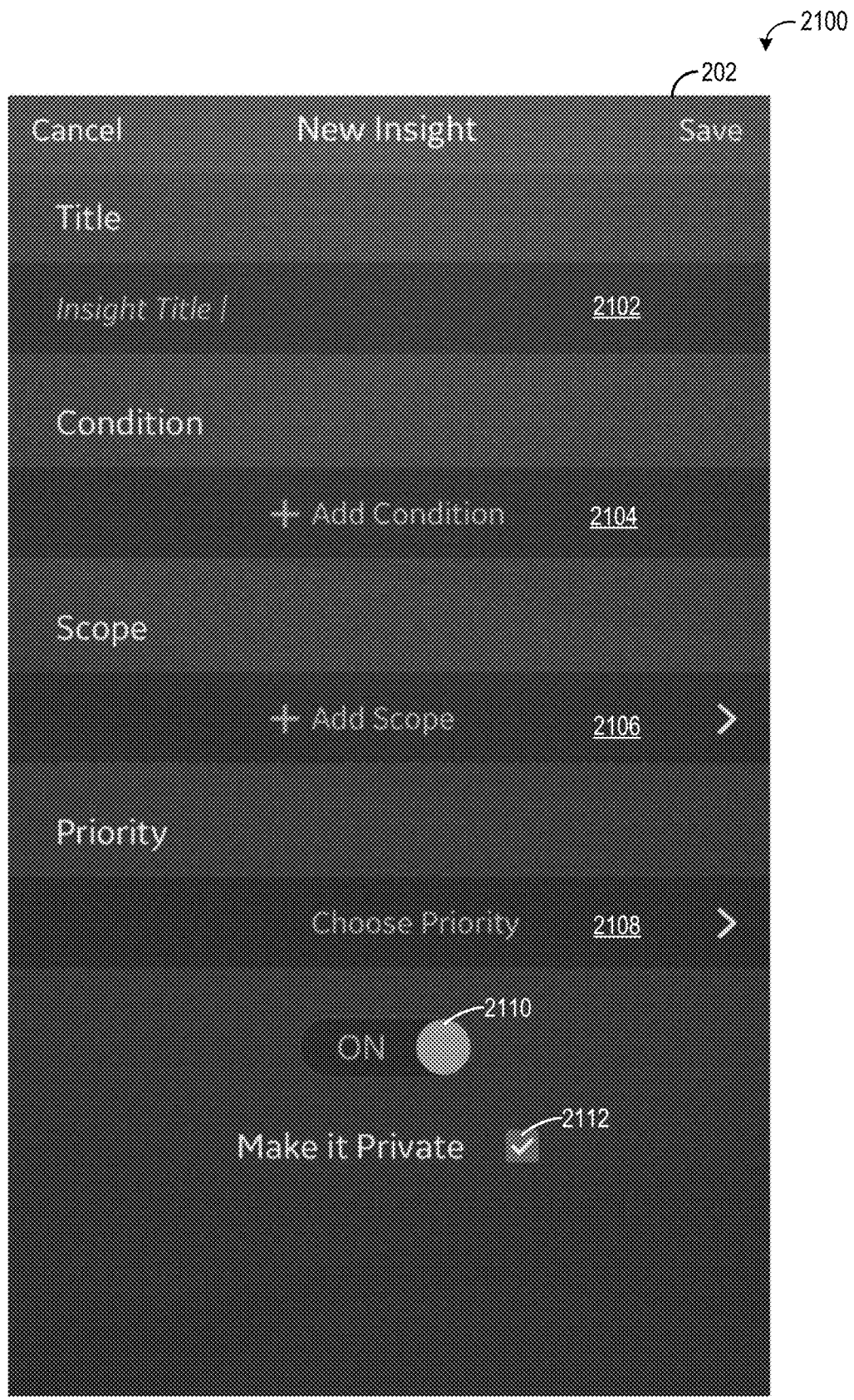
FIG. 21 shows the display device displaying a new insights view generated via the supervisory application.

The example insight shown in FIG. 20 may include a condition (heart rate being greater than 150 beats per minute) and two scopes, the condition persisting for a specified amount of time (e.g., five minutes) and the condition occurring during a particular time of the procedure (e.g., during maintenance phase). The user may create the example insight via a new insights view of the insights GUI. FIG. 21 shows an example new insights view 2100 that may be displayed on display device 202 in response to a user request to create a new insight, such as in response to user selection of a new insight button (e.g., button 1910 of FIG. 19). Via the new insights view 2100, a user may enter a title for the insight in a title box 2102, add a condition for the insight via a condition menu 2104, add a scope for the condition via a scope menu 2106, and select a priority for the insight (e.g., low, medium, or high) via a priority menu 2108.

The condition(s) that may be added via the condition menu 2104 may be selected from a predefined set of parameters. The predefined set of parameters may include any patient monitoring parameter available in the system, and thus selection of the condition menu 2104 may launch a view that is similar to the view shown in FIG. 16 where available patient monitoring parameters are shown and may be selected for the condition. The predefined set of parameters may include other insights that the user has created or selected to be applied. Once a patient monitoring parameter is selected, a threshold for that parameter may be entered. The scope for the condition may be fully user defined (e.g., the user may enter text to define the scope) or the scope menu 2106 may include different types of scopes from which the user may select (e.g., number of minutes the condition is to persist, the phase of the procedure the condition is to occur in, etc.). The scope menu may include a predefined set of operators, such as "and", "or", "while", and so forth, that may allow the user to create an insight having multiple parameters and/or multiple scopes. In doing so, the user may gain more knowledge of patient status than by relying on the machine-generated alarms, which may only track a single patient monitoring parameter.

Further, the user may select to turn on the insight via an on/off button 2110 and may adjust the privacy setting of the insight, such as share the insight or make the insight private, via a share selection box 2112. Once the user has created the insight and set all the insight parameters, the insight may be saved by selecting the save button.

While the insights presented above primarily include threshold or limit-based insights (e.g., if mean arterial blood pressure is above a threshold for a given duration) intended to notify a user of a patient condition that is already occurring, some insights (referred to herein as "signs of trouble" or predictive insights) may provide predictions of future patient conditions based on past and current patient monitoring parameters, patient data, etc. For example, a hypoxia predictive insight may provide a risk score indicative of how likely a patient is to exhibit hypoxia within a given time period (e.g., in the next five minutes, in the next minute). The predictive insights described herein (more details are provided below about the predictive insights) may allow a user to be notified of a potential patient condition before any individual patient monitoring parameter has reached an alarm state. In the example hypoxia predictive insight described above, a prediction of potential hypoxia may be provided while patient oxygen levels are still within a normal or allowable range. Thus, the hypoxia predictive insight may inform on the possibility of a future drop in patient oxygen saturation before the patient's measured SpO2 indicates a low enough oxygen saturation condition that would itself trigger an alarm.

When an insight for a patient is triggered (such as when a risk score reaches a predetermined condition relative to a threshold), a user, such as the supervising care provider, may be notified of the triggered insight via the supervisory application (e.g., an insight button on the supervisory application GUI for the patient may be adjusted to show an insight has been triggered). The user may access additional information via the supervisory application related to the insight, such as the patient monitoring parameters that contributed to the insight, trends of those patient monitoring parameters, etc., which may allow the user to assess the urgency and/or accuracy of the insight or alarm. The additional information may inform the user if the patient condition that triggered the insight requires immediate attention (which may result in the user having to leave the patient the user is currently attending to), if the patient can be attended to by another user (e.g., a subordinate care provider), and/or if care of the patient by the user can be delayed.

Examples of a predictive insight and additional information accompanying notification of the predictive insight are presented below with respect to FIGS. 22-25.

Figure 22:
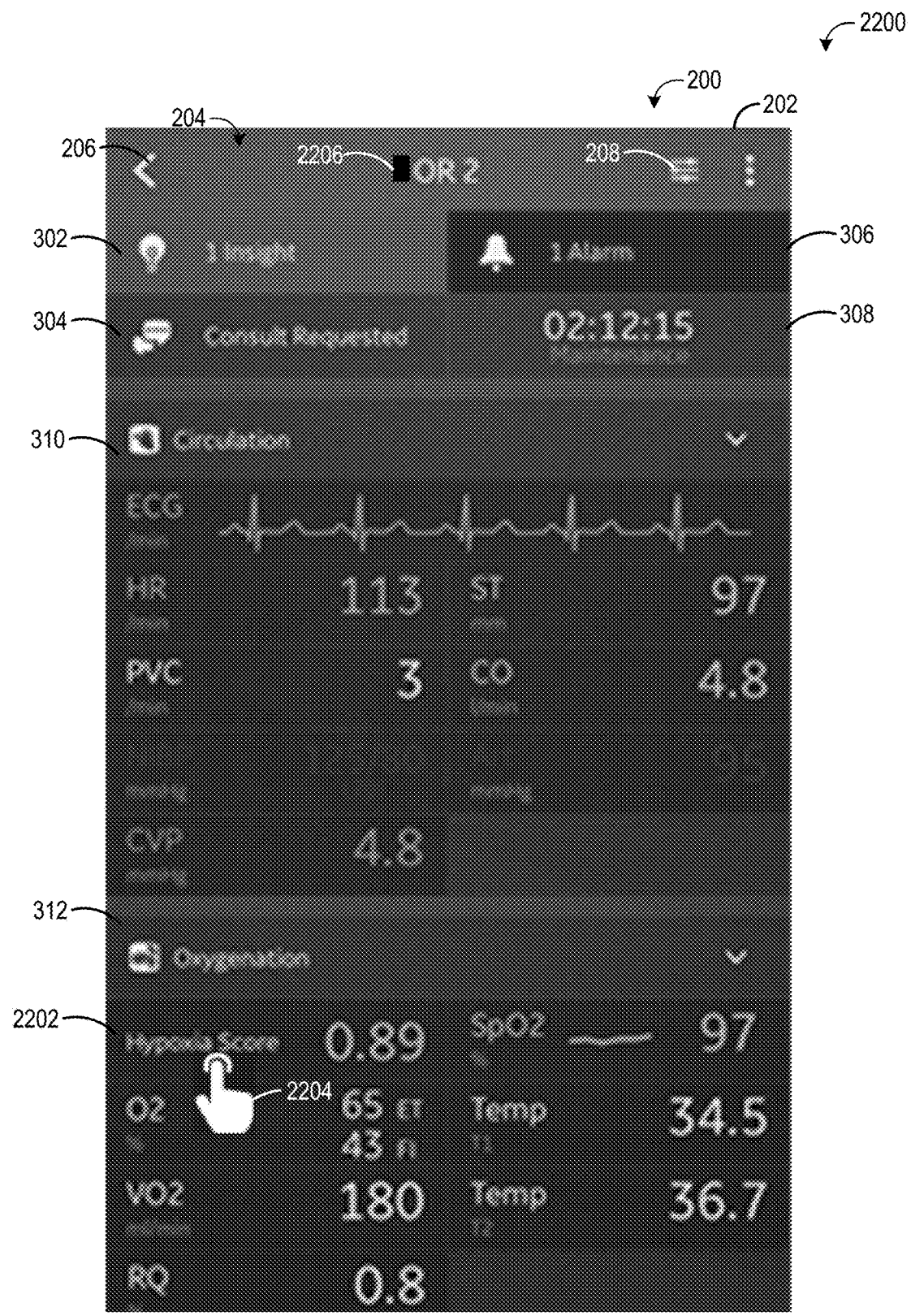
FIG. 22 shows the display device displaying a first insight view of the single-patient graphical user interface generated via the supervisory application.

FIG. 22 shows a first insight view 2200 of single-patient GUI 200 (described above with respect to FIGS. 2-10) displayed on display device 202. The first insight view 2200 includes the insights tile 302, the message tile 304, the alarms tile 306, and the procedure timing tile 308. In the first insight view 2200, an insight has been triggered, which is reflected in the insights tile 302. Likewise, an alarm has been triggered, which is reflected in the alarm tile 306. In the example shown in FIG. 22, the triggered insight is a hypoxia predictive insight, which is explained in more detail below. However, it is to be understood that other insights may be triggered, and that any triggered insight will be reflected in the insights tile 302.

In the first insight view 2200, the user has selected two categories to expand (the circulation category 310 and the oxygenation category 312). As explained above, the circulation category 310 includes eight patient monitoring parameters (e.g., an ECG waveform, a most-recently determined heart rate, and so forth) each related to circulation. The oxygenation category 312 includes the six patient monitoring parameters (e.g., a most-recently determined SpO2) each related to oxygenation discussed above with respect to FIG. 4A. In the first insight view 2200 of single-patient GUI 200, the oxygenation category 312 further includes a hypoxia score tile 2202. The hypoxia score tile 2202 displays the output of the hypoxia predictive insight. The hypoxia predictive insight may include a deep learning or other suitable model that utilizes a plurality of time series data signals of a plurality of patient monitoring parameters as input and outputs a hypoxia risk score that indicates a relative likelihood that the patient is undergoing or is about to undergo hypoxia. In the example shown in FIG. 22, the hypoxia score is on a scale of −1.00-1.00, with −1.00 indicating a lowest risk of hypoxia and 1.00 indicating a highest risk of hypoxia. However, other scores are possible, such as on a scale from 0-10 or 0-100 or a text-based score (e.g., low, intermediate, high). Additional details regarding the hypoxia predictive insight are presented below with respect to FIG. 29.

The hypoxia predictive insight is one example of a predictive insight, and other predictive insights may be applied. The other predictive insights may include predictions of hyperoxia, sepsis, hypotension, hypertension, elevated or depressed heart rate, respiratory depression, and other patient conditions that could impact patient care. Further, more than one predictive insight may be applied. The predictive insight(s) may be applied to each patient the user is attending to/has selected. The risk scores from each predictive insight, for each patient, may be normalized (e.g., all presented on a scale from 0-1) to facilitate direct comparison of severity/urgency of each predictive insight for each patient. In this way, the user may be notified when one or more patients exhibit the potential for deterioration, along with an indication of the potential severity of each potential deterioration. By presenting the normalized risk scores to the user, the user may make an informed decision regarding which patient(s) to prioritize if urgent care is indicated.

As shown in FIG. 22, the hypoxia score tile 2202 is displayed as part of the oxygenation category 312. The user may select which category a selected risk score tile (also referred to as a predictive tile herein) is to be displayed, at least in some examples. In other examples, the category in which a selected risk score tile is to be displayed may be determined automatically and/or set by the creator of the predictive insight. Different output from different predictive insights may be displayed in different categories. For example, the output from a hypotension predictive insight may be displayed as part of a hypotension score tile in the circulation category. In still further examples, the risk score tile(s) may be displayed in an area of the GUI 200 that is separate from the various categories described herein (e.g., in a "predictive insights" category) or not displayed on the GUI 200 at all, unless the user selects the insights tile 302.

To facilitate rapid notification of predictive insights in a manner that allows the user to quickly assess relative severity, the GUI 200 may include a patient severity indicator, such as patient severity indicator 2206. The patient severity indicator may be a color-coded or shape-coded symbol that is displayed in the header 204 or other easily-visualized location. In the example shown in FIG. 22, the patient severity indicator 2206 is a box displayed in header 204 next to the patient identification information (herein, in the form of the operating room in which the patient is located). The color of the box may convey the relative severity of the potential patient deterioration as determined from the output of the one or more predictive insights. For example, red (as shown) may indicate high severity, while yellow may indicate intermediate severity and green may indicate low severity. The high severity of the indicator 2206 may reflect the relatively high hypoxia score as shown in the hypoxia score tile 2202. For example, scores of 0.75-1.00 may be considered high severity, scores of 0.50-0.74 may be considered intermediate severity, while scores below 0.50 may be considered low severity. The thresholds for indicating whether a risk score is high severity, intermediate severity, or low severity may be set by a user. When multiple predictive insights are applied for a patient, the highest score may be used to determine the patient's severity for coding the indicator. In other examples, the scores may be averaged or summed to generate an overall score usable to determine the severity of the patient for coding the indicator. A patient severity indicator may be displayed for each patient, such as in the multi-patient GUI 1300.

In some examples, the user (e.g., the supervising care provider) may opt for the hypoxia score tile 2202 to be displayed in the oxygenation category (or another suitable category) at all times. In other examples, the user may opt for the hypoxia score tile 2202 to be displayed in the oxygenation category only when the hypoxia score is above a threshold, such as above 0.50. In some examples, this threshold may be the same threshold as applied to trigger the insight notification for the hypoxia predictive insight (e.g., the hypoxia score tile may be displayed only when the hypoxia predictive insight has been triggered and the insight tile reflects that the insight has been triggered).

Figure 23A:
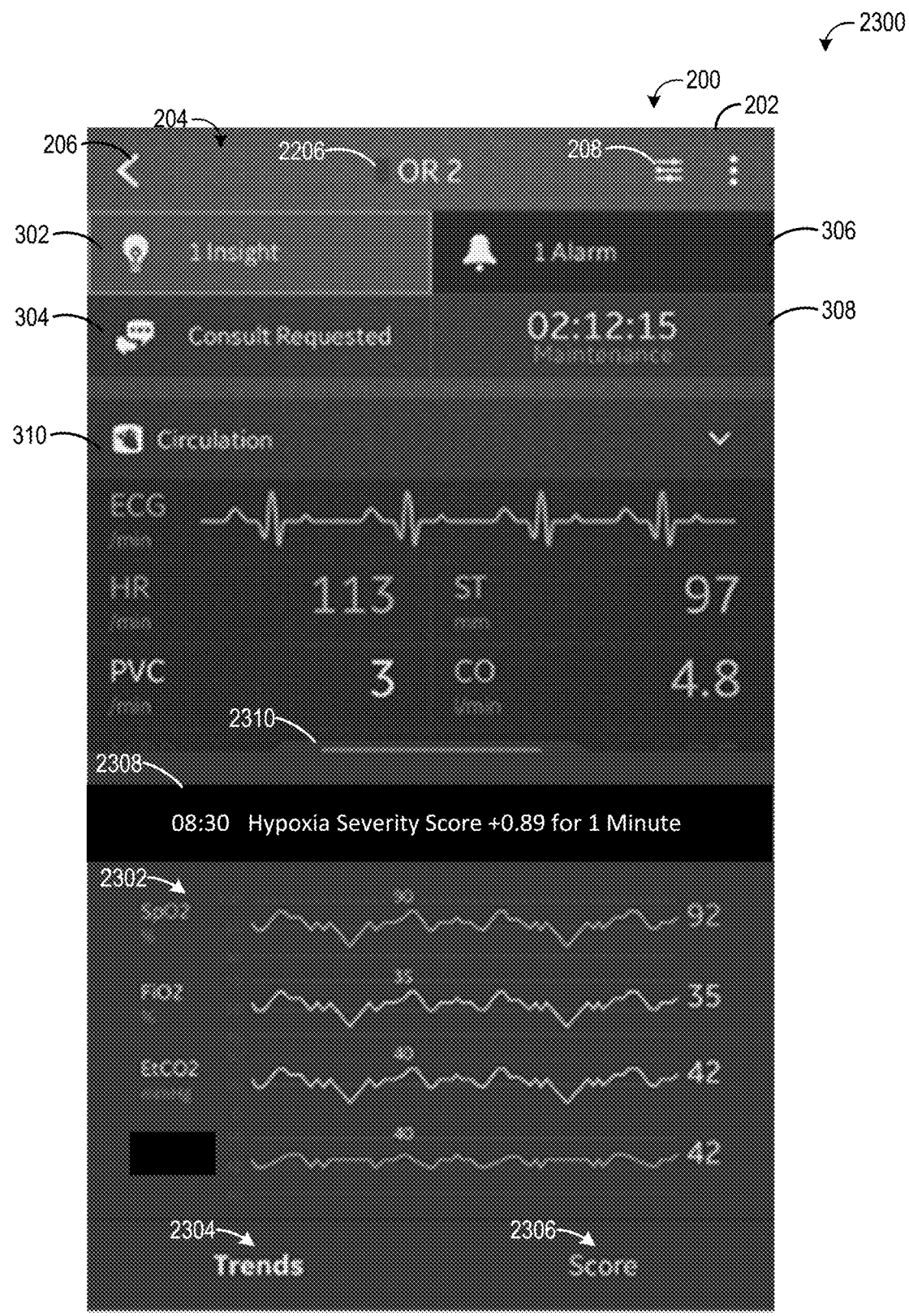
FIGS. 23A-23D show the display device displaying different examples of a second insight view of the single-patient graphical user interface generated via the supervisory application.

The user may enter an input to insights tile 302 or to the hypoxia score tile 2202, such as a single touch input (schematically shown by hand 2204). Selection of the insights tile 302 or hypoxia score tile 2202 may trigger a second insight view 2300 to be displayed, as shown in FIG. 23A. The second insight view 2300 may display additional information related to the hypoxia score, including at least a subset of the patient parameters (e.g., SpO2, end-tidal CO2) that contributed to the hypoxia score, which may allow the user to assess the accuracy and/or urgency of the hypoxia risk of the patient.

Figure 25:
FIG. 25 shows the display device displaying a fourth insight view of the single-patient graphical user interface generated via the supervisory application.

FIG. 23A shows a first example of a second insight view 2300 of the single-patient GUI 200. A set of trends 2302 is displayed at a bottom portion of the single-patient GUI 200. In some examples, the set of trends 2302 may be displayed by default in response to the selection of the insight tile 302 or the hypoxia score tile 2202. In other examples, the set of trends 2302 may be displayed in response to selection of a trends button 2304 shown at the bottom of the second insight view 2300 of the single-patient GUI. The second insight view 2300 of the single-patient GUI 200 further includes a score button 2306 that may trigger display of a set of score trends of the determined hypoxia score, which is shown in FIG. 25 and described in more detail below.

The set of trends 2302 includes a trend line for each of one or more patient parameters/input signals that were determined to contribute (e.g., positively) to the hypoxia score output by the hypoxia predictive insight. As explained above, the hypoxia predictive insight may utilize a plurality of patient parameters as inputs, such as 10 or more inputs. However, not each patient parameter may contribute to the determined hypoxia score. For example, some patient parameters may not be relevant to the hypoxia score, or the determined values for some patient parameters may be normal and/or not changing and thus are not indicative of potential hypoxia. Thus, the set of trends 2302 may include trend lines of only the patient parameters determined by the hypoxia predictive insight to have contributed (or contributed in a significant way) to the hypoxia score. As will be explained in more detail below with respect to FIG. 29, the hypoxia insight may rank each input patient parameter in an order of contribution to the hypoxia score, and the highest ranking (e.g., highest four) patient monitoring parameters may be included in the set of trends.

In the example shown in FIG. 23A, a respective trend line is shown for SpO2, FiO2, EtCO2, and BP_dias. Each trend line is plotted on its own y-axis, such that the values of each patient monitoring parameter may be plotted on different scales and with different units where applicable. Each trend line is plotted on a common x-axis, so that the trend lines are time-aligned. The trend lines may be stacked vertically. In this way, relationships or correspondence of changes among the displayed patient monitoring parameters may be easily identified by the user. Further, a most recent value for each patient monitoring parameter is shown to the right of each trend line.

Figure 24:
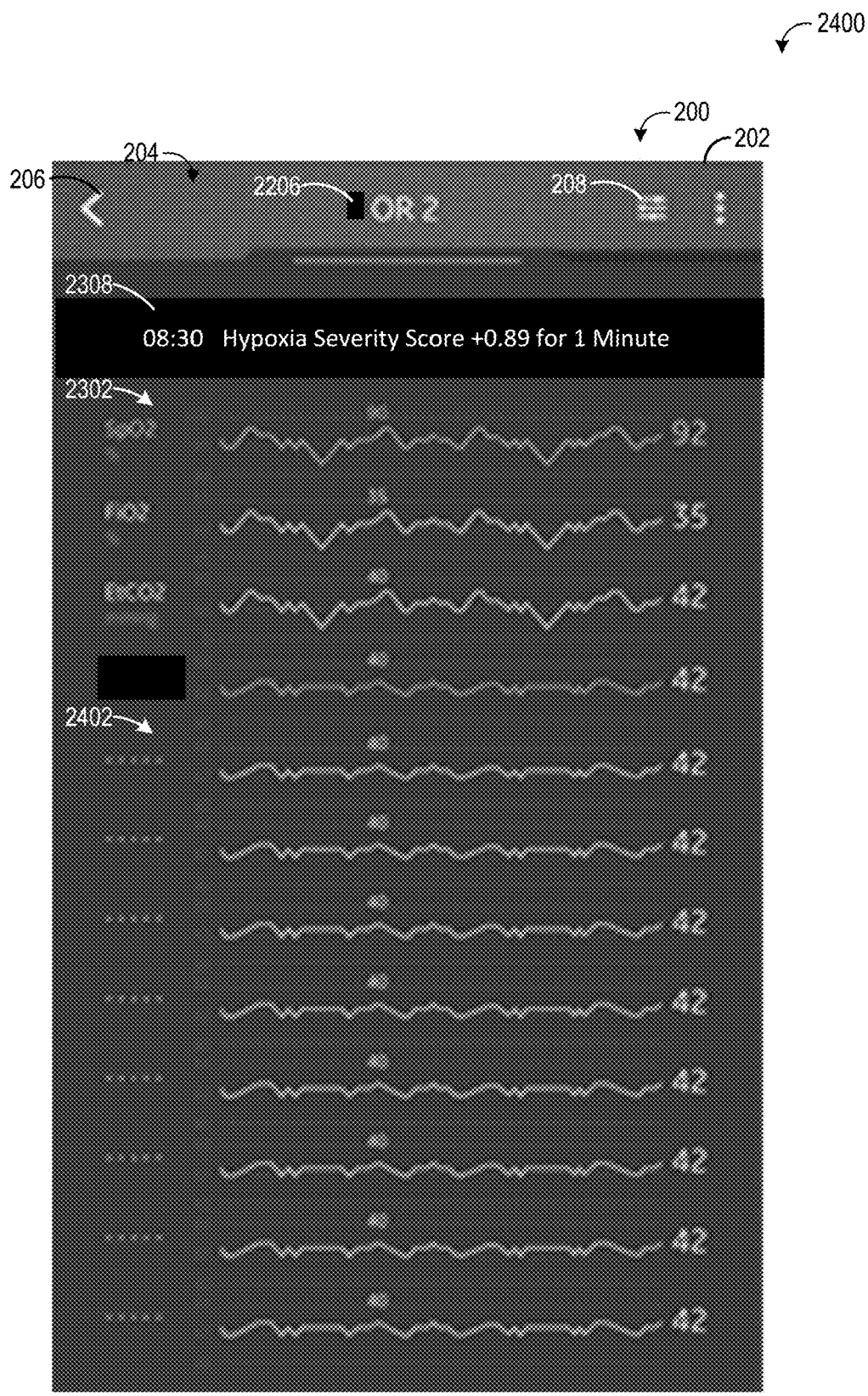
FIG. 24 shows the display device displaying a third insight view of the single-patient graphical user interface generated via the supervisory application.

Additionally, the second insight view 2300 includes an information banner 2308 and a swipe tab 2310. The information banner 2308 may include information related to the selected predictive insight, herein a current time (e.g., 08:30), the current hypoxia score, and the amount of time that the current hypoxia score has persisted (or the amount of time that the hypoxia score has been above a threshold, such as 0.50). When the user makes a down-swipe motion to the swipe tab 2310, the set of trends 2302 may collapse to reveal the categories/patient monitoring parameters displayed in the first insight view 2202. When the user makes an up-swipe motion to the swipe tab 2310, additional trend lines may be shown. FIG. 24 shows a third insight view 2400. The third insight view 2400 includes the set of trends 2302 as well as one or more additional trends 2402. The one or more additional trends may include trend lines for one or more additional patient monitoring parameters. The additional patient monitoring parameters shown as part of the one or more additional trends 2402 may be patient monitoring parameters that contributed to the hypoxia score (though with a less significant contribution than the patient monitoring parameters shown as part of the set of trends 2302) and/or patient monitoring parameters that did not contribute to the hypoxia score. For example, the third insight view 2400 may include a plurality of trend lines displayed in order of contribution to the hypoxia score (e.g., from the parameters that resulted in high, positive scores to parameters resulting in low, negative scores).

Returning to FIG. 23A, the window of time over which the patient monitoring parameters of the set of trends 2302 are shown may be a default window of time that does not change based on the risk score, the patient, the contributing patient monitoring parameters, or other factors. For example, each time a set of trends is displayed in response to selection of the insight tile, the risk score tile, or the trends button, the resultant set of trends that is displayed may include values for the selected patient monitoring parameters over a predefined window of time, such as the most recent 15 minutes, the most recent 30 minutes, etc. However, in some examples, the window of time may be adjusted based on the patient monitoring parameter(s) and/or feature(s) of the patient monitoring parameter(s) that were determined to contribute significantly to the risk score.

Figure 23B:
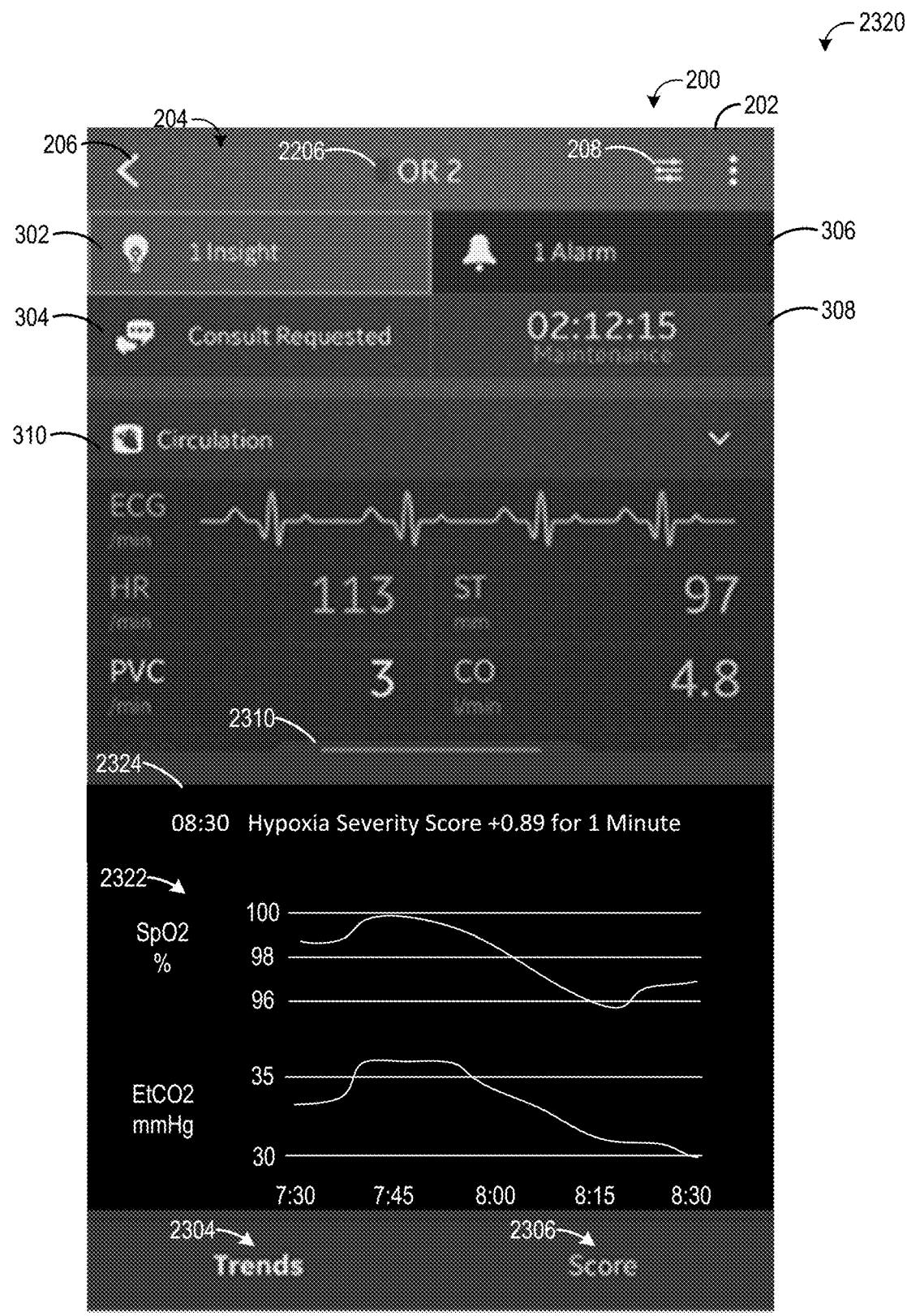

FIG. 23B shows a second example 2320 of the second insight view of the single-patient GUI 200 displayed on display 202. In the second example, a second set of trends 2322 is shown. The second set of trends includes fewer trend lines than the first set of trends, as only two patient monitoring parameters (SpO2 and EtCO2) were determined to contribute positively to the hypoxia score. The second example 2320 also includes labeled time points across the bottom of the second set of trends 2322, indicating that the values for SpO2 and EtCO2 shown in the second set of trends 2322 are plotted over the prior 60 minutes of time. As can be appreciated by the second set of trends 2322, both SpO2 and EtCO2 started decreasing around 7:45-8:00, and continued decreasing at steady rates until about 8:15. Thus, the selected 60 minutes of time over which the patient monitoring parameters are plotted allows the contributing features of the selecting patient monitoring parameters (e.g., the decrease in the values of the SpO2 and EtCO2) to be visualized at the same time. The second example 2320 also includes a second information banner 2324, showing the time, the risk score, and the duration of the current risk score.

Figure 23C:
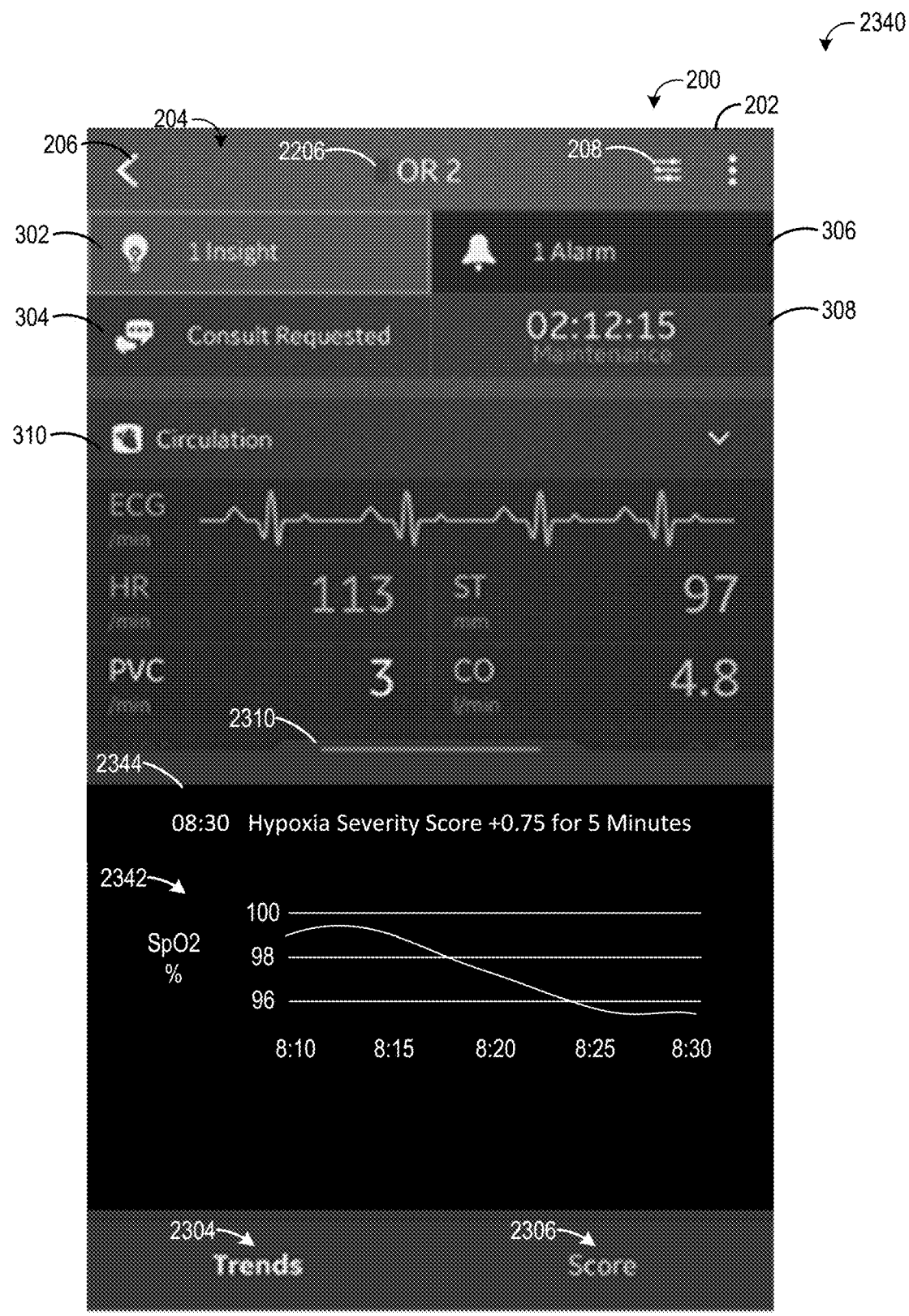

FIG. 23C shows a third example 2340 of the second insight view of the single-patient GUI 200 displayed on display 202. In the third example, a third set of trends 2342 is shown. The third set of trends includes fewer trend lines than the first and second sets of trends, as only one patient monitoring parameter (SpO2) was determined to contribute positively to the hypoxia score. The third example 2340 also includes labeled time points across the bottom of the third set of trends 2342, indicating that the values for SpO2 shown in the third set of trends 2342 are plotted over the prior 20 minutes of time. As can be appreciated by the third set of trends 2342, SpO2 started decreasing around 8:13, and continued decreasing at a steady rate until about 8:25. By showing a smaller window of time (e.g., relative to the window of time shown in the second example described above with respect to FIG. 23B), the duration over which the SpO2 dropped may be visualized in high detail. However, in some examples, the window of time may be expanded to include SpO2 values prior to when SpO2 started decreasing, to allow the user to confirm a baseline SpO2 for the patient. The third example 2340 also includes a third information banner 2344, showing the time, the risk score, and the duration of the current risk score. In the example shown, the hypoxia score may be determined to be caused by a relatively rapid drop in SpO2 (e.g., a drop of 5 percentage points over 12 minutes). However, the SpO2 is still on the higher side (e.g., 95%) and no other patient monitoring parameters are indicating potential hypoxia, which may result in a lower score (e.g., 0.75) than the second example presented above where the hypoxia score was 0.89.

Figure 23D:
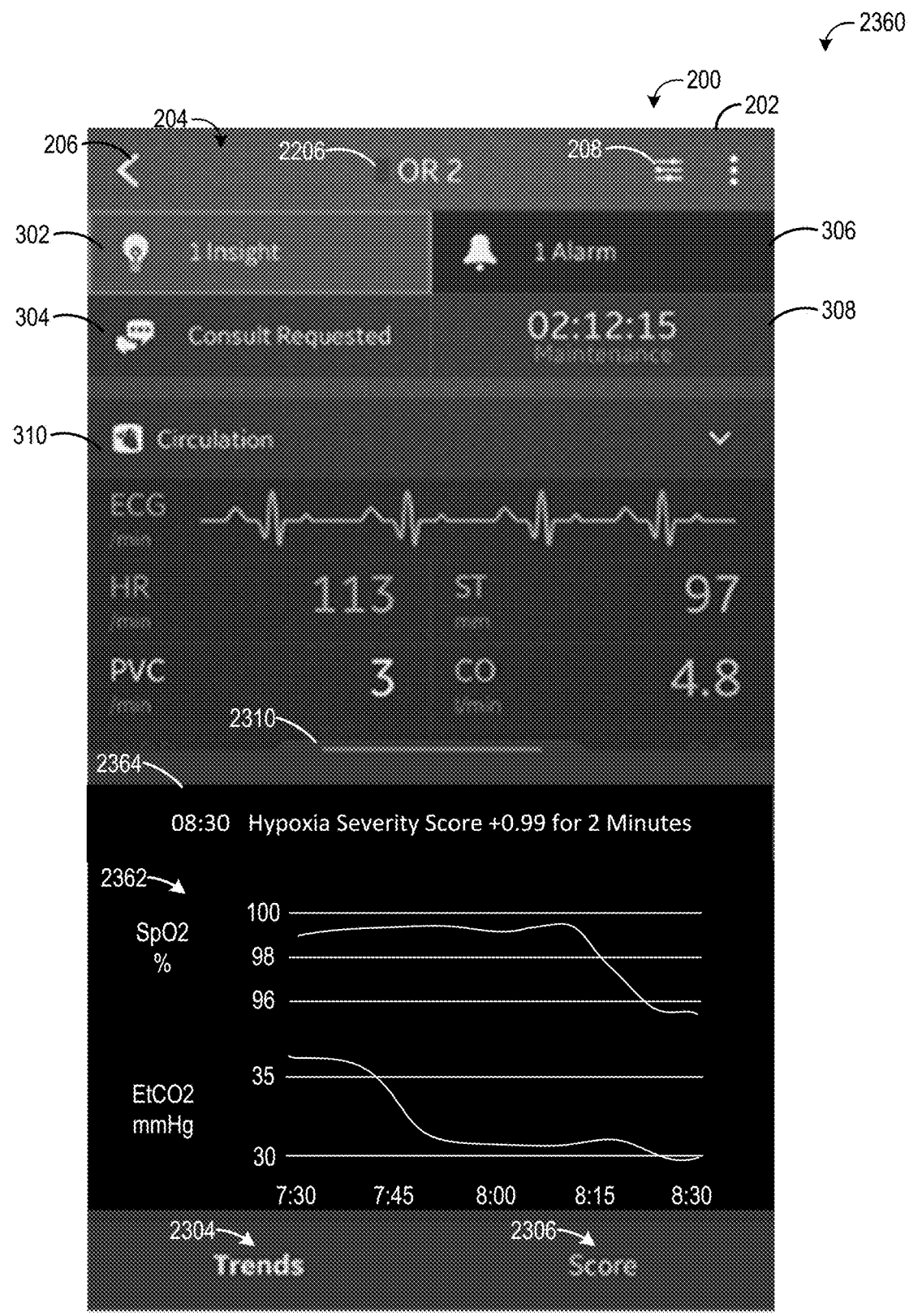

FIG. 23D shows a fourth example 2360 of the second insight view of the single-patient GUI 200 displayed on display 202. In the fourth example, a fourth set of trends 2362 is shown. The fourth set of trends includes two trend lines representing two patient monitoring parameters (SpO2 and EtCO2) determined to have contributed positively to the hypoxia score. The fourth example 2360 also includes labeled time points across the bottom of the fourth set of trends 2362, indicating that the values for SpO2 and EtCO2 shown in the fourth set of trends 2362 are plotted over the prior 60 minutes of time. As can be appreciated by the fourth set of trends 2362, SpO2 stayed relatively steady until about 8:15, at which point SpO2 decreased at a steady, relatively rapid rate until about 8:25. EtCO2 decreased earlier in time, exhibiting a relative rapid decrease from about 7:40 until about 7:50, at which point the EtCO2 stayed steady until dropping slightly again around 8:25.

The window of time shown in the fourth example may be selected so that the initial decrease in EtCO2 is shown along with the decrease in SpO2. The decrease in SpO2 shown in the fourth set of trends 2362 may be similar to the decrease in SpO2 shown by the third set of trends 2342. However, the window of time shown in the fourth example of FIG. 23D may be larger than the window of time shown in the third example of FIG. 23C in order to visualize the contribution to the hypoxia score by the EtCO2.

The fourth example 2360 also includes a fourth information banner 2364, showing the time, the risk score, and the duration of the current risk score. In the example shown, the hypoxia score may be determined to be caused by a relatively rapid drop in SpO2 (e.g., a drop of 5 percentage points over 12 minutes) and by a relatively rapid drop in EtCO2, resulting in a higher score (e.g., 0.99) than the second and third examples presented above where the hypoxia score was 0.89 and 0.75, respectively. It should be noted in some examples, the initial drop in EtCO2 may not be sufficient to result in a hypoxia score that triggers a notification, but the combination of the drop in EtCO2 and the drop in SpO2 may result in a high enough hypoxia score to trigger a notification. In other examples, a notification may have been triggered when the EtCO2 initially dropped.

FIG. 25 shows a fourth insight view 2500 of the single-patient GUI 200. In the fourth insight view 2500, a set of score trends 2502 of the contribution to the hypoxia score of each parameter over time is shown. In some examples, the set of score trends 2502 may be displayed by default in response to the selection of the insight tile 302 or the hypoxia score tile 2202. In other examples, the set of score trends 2502 may be displayed in response to selection of the score button 2306.

The set of score trends 2502 may include the same patient monitoring parameters as shown in the set of trends 2302 of FIG. 23A (e.g., the patient monitoring parameters that contributed to the hypoxia score). Rather than depicting each patient monitoring parameter on a separate y-axis (and hence providing different units/scales for each patient monitoring parameter), each patient monitoring parameter of the set of score trends 2502 is plotted on a common y-axis that depicts the contribution score for each parameter (e.g., on a scale of −0.8-0.8). In the example shown in FIG. 25, the hypoxia score is a value between −1.5 and +1.5. Each patient monitoring parameter (e.g., SpO2, EtCO2, etc.) may be assigned a contribution score indicative of how much that patient monitoring parameter is contributing to the calculated risk (e.g., hypoxia) score. Adding the contribution score of all parameters results in the total risk score. A positive score of a parameter indicates that the parameter was driving the total score higher, indicative of a hypoxia event. In this way, the relative contribution of each selected parameter to the risk score may be visualized over time, in a normalized manner (e.g., such that parameters may be directly compared to each other). The normalization is done as part of the predictive insight/function interpretability feature (described in more detail below) to assess relative contribution of each parameter.

The fourth insight view 2500 may further include a stacked bar plot 2504 that indicates the relative contribution of each parameter towards the total score at the current instance. Parameters in 'Red' have positive values and ones in 'Blue' have negative values. If a parameter is not contributing at the current instance (score=0), it is left out from the stacked bar plot. Additionally, due to space constraints, only a few key contributing factors would be shown at every instance.

Thus, the supervisory application may allow a user, such as a supervising care provider, to oversee multiple patients at one time, from any location within a medical facility. The supervisory application may present patient monitoring parameters in real-time, as well as historical data such as changes in patient monitoring parameters over time, via a plurality of GUIs, as explained above. The GUIs presented above with respect to FIGS. 2-25 may be a first set of GUIs that are displayable if the user is a supervising care provider. For example, upon initially launching the supervisory application, the user may be authenticated via a suitable authentication mechanism. The authentication process may include determining if the user is a supervising care provider (e.g., anesthesiologist supervising multiple nurse anesthesiologists) or if the user is a subordinate care provider (e.g., one of the nurse anesthesiologists). Once the supervisory application has confirmed the identity of the user via the authentication process, the supervisory application may access care provider information stored in memory of a device of the hospital network (e.g., on the edge device, on a hospital operations system device) or available remotely (e.g., via the MDD processing system or other cloud-based service) to determine which care providers the user is supervising (if the user is a supervising care provider) or determine which care provider is supervising the user (if the user is a subordinate care provider), in order to coordinate communication among the supervising care providers and the associated one or more subordinate care providers. If the user is identified as a supervising care provider, the GUIs presented above with respect to FIGS. 2-25 may be displayed on the user's device when prompted. However, if the user is identified as a subordinate care provider, the GUIs presented above may not be displayed. Instead, an in-room GUI that presents information for only for a single patient may be displayed, which may present real-time patient monitoring parameters for a patient and alarm notifications, similar to the single-patient GUIs described above. The in-room GUI may also facilitate rapid communication between the in-room (e.g., subordinate) care provider and the supervising care provider via a one-touch/click consultation button (which requests a consultation with the supervising care provider), a message button that launches a message thread with the supervising care provider, and a snapshot button that captures an image of the current patient monitoring parameters being viewed via the in-room GUI. This image may be sent to the supervising care provider, which may allow the supervising care provider to quickly assess patient state without having to navigate to the supervising care provider's own single-patient GUI for that patient.

Figure 26:
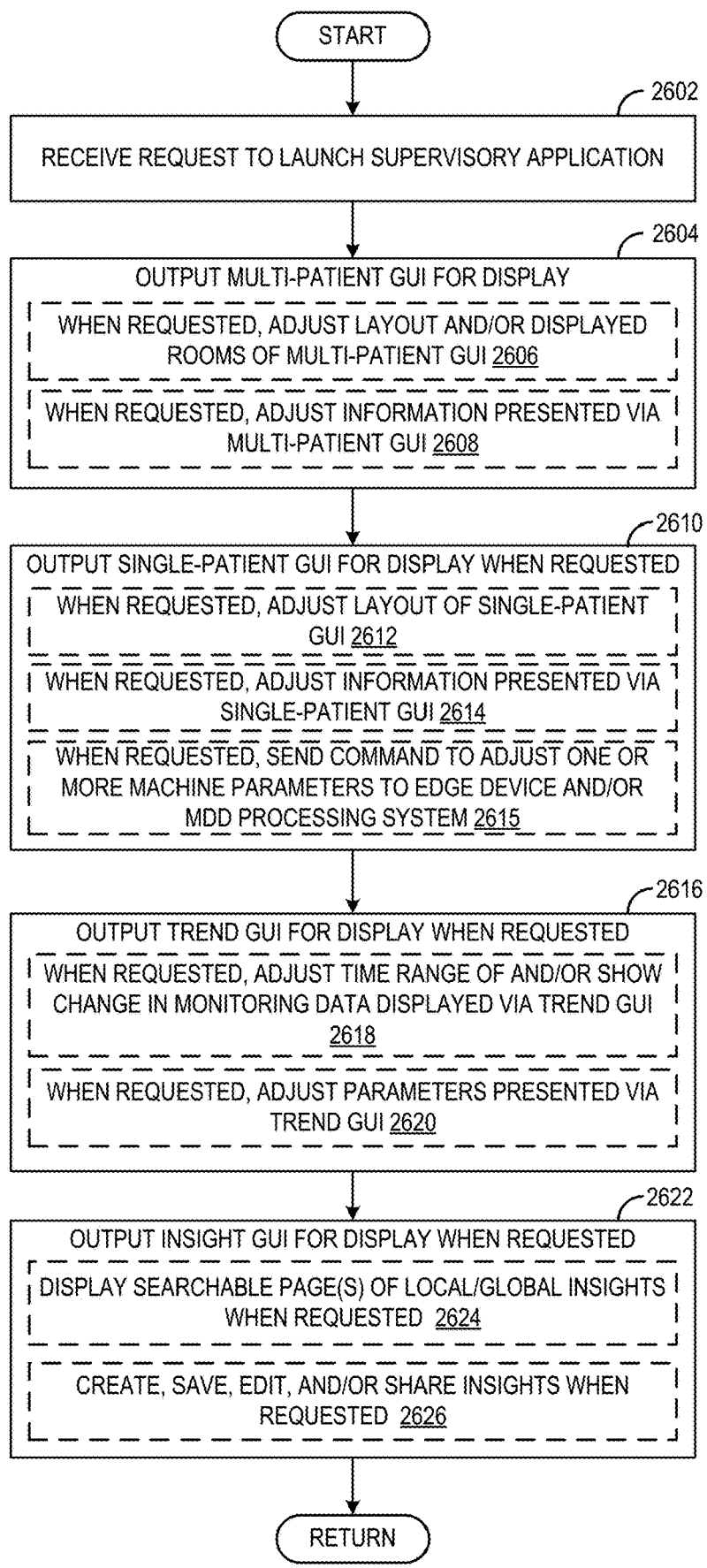
FIG. 26 is a flow chart illustrating an example method for displaying supervising graphical user interfaces generated via the supervisory application.

FIG. 26 is a flow chart illustrating an example method for displaying supervising graphical user interfaces generated via a supervisory application on a display device associated with a care provider device. Method 2600 may be implemented by a care provider device (such as care provider device 134) being used by a supervising care provider in combination with an edge device connected to the care provider device (e.g., edge device 20), a cloud in communication with the edge device and/or care provider device (e.g., MDD processing system 12), or any appropriate combination thereof.

At 2602, a request to launch the supervisory application is received. The request to launch the supervisory application may be received via user input, such as a user of the care provider device selecting a supervisory application icon displayed on a home page or other location of the display device associated with the care provider device. Upon the request to launch the supervisory application being received, a multi-patient GUI is output for display on the display device, as indicated at 2604. In some examples, the multi-patient GUI may be the default page for the supervisory application, such that any time the supervisory application is launched from an unlaunched state, the multi-patient GUI is displayed. Further, in some examples, prior to displaying the multi-patient GUI and after the request to launch the supervisory application is received, an authentication/log-in page may be displayed, via which the user may enter log-in information via text input, via a captured image (e.g., facial recognition), via a fingerprint, or other suitable mechanism for entering credentials for authentication. Once the user is authenticated, the multi-patient GUI may be launched. In still further examples, if the user has not already set up their view of the supervisory application, a set-up page may be displayed after user authentication, via which the user may select which rooms/patients to display in the multi-patient GUI.

As an example, after launching the supervisory application and authenticating the user, the supervisory application may display an initial set-up page, which may include a menu button (similar to menu button 1126 of FIG. 11) that, when selected, causes display of a context menu that includes an add room button, similar to the context menu 1200 and the add room button 1202 of FIG. 12. When the user selects the add room button, an add rooms page may be displayed, similar to the add rooms view 1400 of FIG. 14. The user may then select which rooms/patients are to be added to the multi-patient GUI. In some examples, the initial set-up page may include an add room box or other more direct mechanism that when selected by the user causes display of the add rooms view.

The multi-patient GUI may include limited information for each of a plurality of patients. For example, the multi-patient GUI 1100 of FIG. 11 includes, for each selected room/patient, a subset of all available patient monitoring parameters that may be viewed for that patient (e.g., the patient monitoring parameter tiles 1118, 1120, 1122, and 1124) and one or more alert and timing tiles, such as an alarm tile (e.g., alarm tile 1112), a message tile (e.g., message tile 1114), an insights tile (e.g., insights tile 1110), and a procedure timing tile (e.g., procedure timing tile 1116). The layout of the multi-patient GUI and/or the rooms that are displayed as part of the multi-patient GUI may be adjusted when requested, as indicated at 2606. For example, the multi-patient GUI 1100 of FIG. 11 may be a first layout for the multi-patient GUI, and the user may select to switch to a different layout, such as the layout of the multi-patient GUI 1300 of FIG. 13, by selecting the appropriate layout from the context menu. The second layout shown in FIG. 13 may include the alert and timing tiles, but may not include any patient monitoring parameter tiles. Further, the user may add or remove rooms/patients from the multi-patient GUI by selecting the add rooms button of the context menu (e.g., button 1202 of menu 1200), which may launch the add rooms view 1400. As explained above, via the add rooms view, the user may add rooms/patients to the multi-patient GUI and may also remove rooms/patients from the multi-patient GUI.

In some examples, the user may further customize the layout of the multi-patient GUI by adjusting the information presented via the multi-patient GUI, as indicated at 2608. As explained previously, the multi-patient GUI may display, via the subset of patient monitoring parameters, real-time determined values for each of the patient monitoring parameters, as received from one or more medical devices (e.g., the medical devices 16 of FIG. 1A, which may include physiological monitoring devices 16*a* as well as patient therapy devices 16*b*, e.g., anesthesia delivery machines) and streamed from an intermediary device (e.g., streamed from the streaming server 114 of the edge device 20). The user may customize which patient monitoring parameters are included in the multi-patient GUI by selecting an edit rooms button of the context menu, such as edit rooms button 1206 of menu 1200, which may cause an edit rooms view to be displayed, such as the edit rooms page 1500 of FIG. 15. Via the edit rooms view, the user may add or remove patient monitoring parameters to the multi-patient GUI in a patient/room-specific manner, select to view the patient monitoring parameters as trends or single values, and/or resize the tiles for the patient monitoring parameters.

At 2610, a single-patient GUI may be output for display when requested. The single-patient GUI may include notifications/alerts and/or patient monitoring parameters for a single patient, rather than multiple patients. Example single-patient GUIs are shown in FIGS. 2, 4A, and 23A and explained above. The single-patient GUI may be output for display in response to a user request, such as the user selecting a room/patient from the multi-patient GUI. For example, referring to FIG. 13, user selection of the forward button 1301 may cause single-patient GUI 200 to be displayed. The single-patient GUI may include more information for the selected patient than the corresponding information in the multi-patient GUI for that patient, thus allowing the care provider to drill down to a more-detailed for a single patient when desired.

The single-patient GUI, similar to the multi-patient GUI, may be customized by the user to have a desired layout, display desired information, and so forth. Thus, as indicated at 2612, the layout of the single-patient GUI may be adjusted when requested. The layout may be adjusted similarly to the layout adjustment of the multi-patient GUI, e.g., in response to user selection of a desired layout from a context menu (e.g., context menu 500 of FIG. 5). Further, as indicated at 2614, the information presented via the single-patient GUI may be adjusted when requested. Similar to the multi-patient GUI, the single-patient GUI may be adjusted via an edit rooms view and/or add tiles view similar to the edit rooms page 1500 of FIG. 15 and add tiles page 1600 of FIG. 16.

In some examples, a user may request to add a patient monitoring parameter to the single-patient GUI, remove a patient monitoring parameter from the single-patient GUI, request to view a patient monitoring parameter as a value or as a trend in a tile, request to view the result of an insight (including predictive insights) as a tile on the single-patient GUI, or perform another action that may cause the layout of the single-patient GUI to change. In such examples, one or more of the remaining patient monitoring parameter tiles on the single-patient GUI may be adjusted in response to the user action. For example, one or more patient monitoring parameter tiles may be moved, resized, scaled, etc., to accommodate a newly added tile, take up space left by a removed tile, and so forth. The adjustments may be performed automatically by the supervisory application in some examples. When a tile is resized, different information may be displayed in a smaller tile versus a larger tile. As an example, if a user chooses to view a patient monitoring parameter as a trend rather than or in addition to a value, that patient monitoring parameter tile may be increased in size and more information may be displayed. If a patient monitoring parameter tile is reduced in size, less information may be shown. Further, each patient monitoring parameter tile may have seven states: a numerical state, an edit state, a selected state, a trend state, a waveform state, an alarm state, and a drag state, which may be displayed according to user input. The numerical state may show only a value for that parameter, the edit state may include a checkbox allowing the user to select or deselect the parameter (thus adding or deleing the tile), the selected state may include a visual indication that the tile has been selected by the user (e.g., highlighting), the trend state may include a trend of the parameter over time (e.g., a trend line), the waveform state may show the parameter as a waveform rather than value (e.g., ECG waveform), the alarm state may highlight the value of the parameter if an alarm condition is reached, and the drag state may include the tile having a visual appearance indicating the user is dragging the tile (e.g., to a new location), such as the tile changing color or transparency.

As explained previously, the patient monitoring parameters that may be displayed via the single-patient GUI may include physiological parameters such as measured or inferred heart rate, blood pressure, temperature, and so forth. The patient monitoring parameters may further include, at least in some examples, machine settings for one or more therapy devices being used to carry out a procedure on the patient (or being used in support of the procedure being carried out on the patient), such as settings for an anesthesia delivery machine. The settings may include anesthetic agent concentration, medical gas flow rate, ventilator settings, and so forth. While viewing these settings may be helpful for a user who is located in a different location than the patient (e.g., attending to another patient), the supervisory application may also allow for the user to directly adjust one or more machine settings remotely, without having to actually be in the room where the therapy device is located. Accordingly, as indicated at 2615, a command to adjust one or more machine parameters may be sent to the edge device and/or MDD processing system, when requested. At 2616, a trends GUI may be output for display when requested. The trends GUI may include trends in selected patient monitoring parameters over time. FIG. 6 shows an example trends GUI, where each trend is visualized as a trend line over the same time duration (e.g., 10 minutes, 30 minutes, or the entire case). The trends GUI may be displayed in response to user selection of a trends button of a single-patient GUI context menu, such as trends button 502 of menu 500. In other examples, the trends GUI may be displayed in response to user selection of a trends icon displayed on the single-patient GUI, such as trends icon 474 of FIG. 4D. The time range of the patient monitoring parameter values displayed in the trends GUI may be adjusted when requested, as indicated at 2618. For example, the trends GUI may include a plurality of buttons each corresponding to a different time range, and user selection of one of the buttons may cause the time range of the displayed trends to change. Further, as also indicated at 2618, the trends GUI may show a quantified change in patient monitoring/medical device data over a specified time period when requested. The quantified change may include an overall percent change between two specified time points, as shown in FIG. 7, which may be requested in response to user input (e.g., a concurrent two touch input to the trends GUI). The trends of the patient monitoring parameters presented via the trends GUI may be adjusted when requested, as indicated at 2620. For example, the trends GUI may include an edit button, such as edit button 608, that causes a trend edit page to be displayed. Via the trend edit page, patient monitoring parameters may be added or removed from the trends GUI. Further, the relative location of each trend on the trends GUI (e.g., the order in which the trends are presented) may be adjusted via the trend edit page.

At 2622, an insights GUI may be output for display when requested. The insights GUI may present insights, which are similar to threshold-based alarms but may be based on more parameters, have limitations on when the insights are applied, and other factors that may make the insights more nuanced and less binary than threshold-based alarms. The insights GUI may be output for display in response to a user request, such as a user selection of an insight engine button from a context menu (e.g., selection of insights engine button 1204 of menu 1200) or other suitable user input. As indicated at 2624, outputting the insights GUI may include displaying a searchable page(s) of local and/or global insights, generated by other users, when requested. FIG. 17 shows an example of a searchable page of the insights GUI, where insights generated by other users at the medical facility where the user is employed (e.g., the local insights) may be displayed, browsed, and/or searched, and where insights generated by other users at other medical facilities (e.g., the global insights) may be displayed, browsed, and/or searched. The user may select one or more insights to be applied to the user's patients/rooms. As indicated at 2626, outputting the insights GUI may include creating, saving, and/or sharing insights when requested. For example, FIG. 19 shows a "my insights" view of the insights GUI where the user may view all insights saved and/or created by the user. When an insight is selected, an insight edit page may be displayed, where the user may turn on or off an insight or edit the rules for the insight. A user may create an insight, such as via the new insights view shown in FIG. 21. Further, an insight may be shared in response to user request (e.g., via selection of a share insight button, such as button 2010 of FIG. 20). When an insight is shared, the privacy setting of the insight may be adjusted to allow other users to view and apply the insight. This may include the insight being sent to another device and/or the cloud, where other users may access the insight. Method 2600 then returns.

Figure 27:
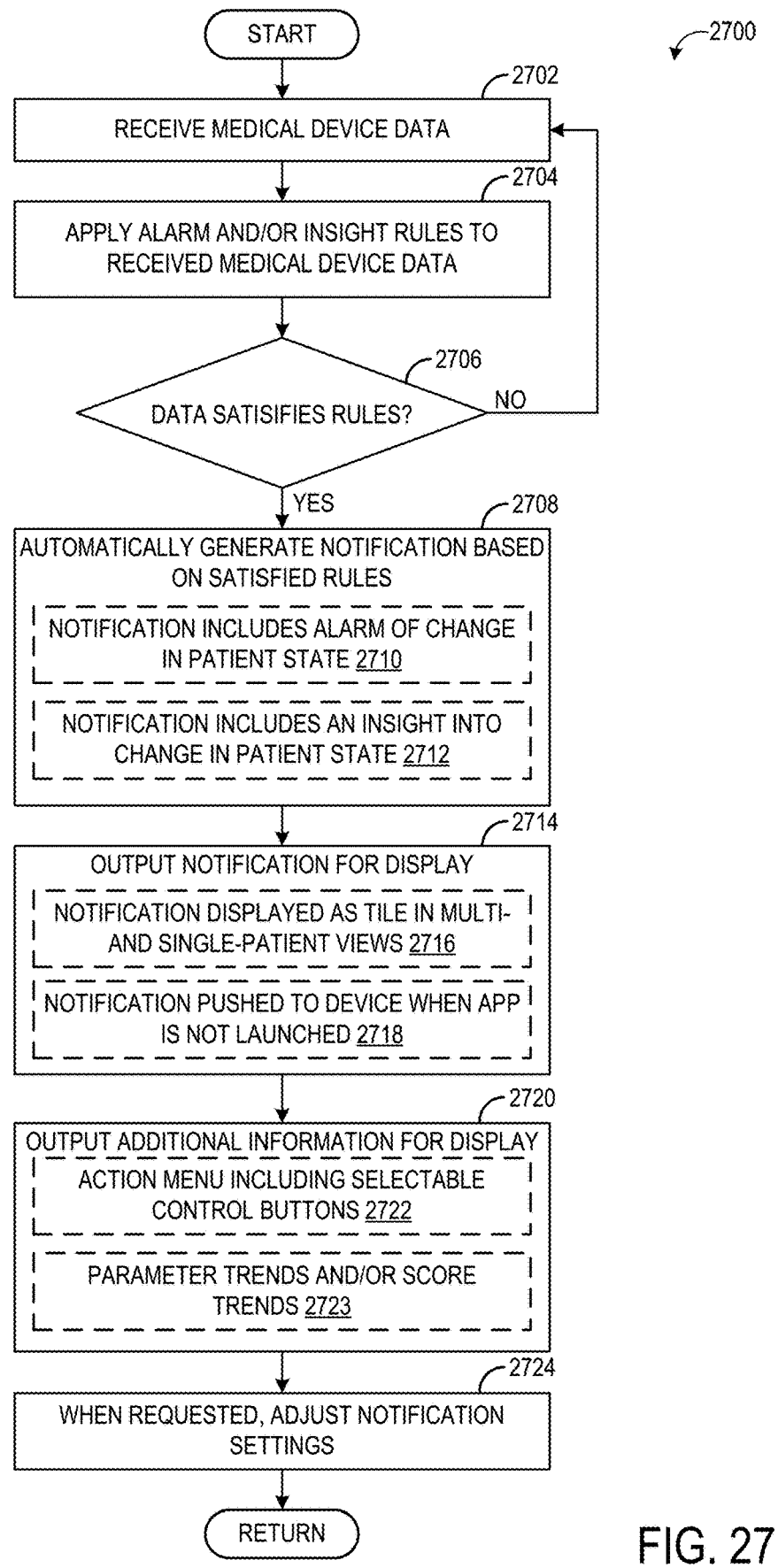
FIG. 27 is a flow chart illustrating an example method for generating and outputting notifications via the supervisory application.

FIG. 27 is a flow chart illustrating an example method 2700 for generating and outputting notifications via the supervisory application. The notifications that are output via the method 2700 of FIG. 27 may be output on a display device associated with a care provider device. Method 2700 may be implemented by a care provider device (such as care provider device 134) in combination with an edge device connected to the care provider device (e.g., edge device 20), a cloud in communication with the edge device and/or care provider device (e.g., MDD processing system 12), or any appropriate combination thereof.

At 2702, medical device data is received. The medical device data may be received from one or more medical devices, such as the medical devices 16 of FIG. 1A. The medical device data may be received by a data ingestion module of the edge device, for example, and in some examples may be processed by a stream processing module of the edge device, as explained above with respect to FIG. 1B. At 2704, alarm and/or insight rules are applied to the received medical device data. For example, the medical device data that is received may be supplied to a rules engine and/or an inference engine of the edge device, which may apply insight rules in order to determine if the received medical device data satisfies any of the saved insight rules. The insight rules may include a plurality of sets of insight rules with each set of insight rules including a condition and a scope of the condition. For example, the condition may include a specified patient monitoring parameter and a condition relative to a threshold for that patient monitoring parameter (e.g., heart rate being greater than 150 beats per minute) and the scope may include a duration of the condition and/or procedure phase in which the condition is to occur in order to trigger the insight, such as for five minutes and/or during maintenance phase of anesthesia delivery. Each set of alarm rules and each set of insight rules may also include an indication of which patient(s) the rules are applicable to and may also include an indication of which user(s) of the supervisory application should receive a notification if the alarm rules or insight rules are satisfied. In some examples, such as when the insight is a predictive insight, the insight rules may include a more complex model, such as a deep learning model. Additional details about applying a predictive insight are provided below with respect to FIG. 29.

The alarm rules may include a plurality of sets of alarm rules, with each set of alarm rules including a specified patient monitoring parameter (e.g., heart rate) meeting a condition relative to a threshold (e.g., being greater than 150 beats per minute). In some examples, the alarms described herein may be generated by individual medical devices and sent to the edge device, which then outputs the alarm to the appropriate care provider device (as explained below). In such cases, the only alarm rules that may be applied by the supervisory application may include whether a user has chosen to receive a particular alarm or has chosen to not be notified of a particular alarm.

At 2706, method 2700 includes determining if the received medical device data satisfies the alarm rules and/or the insight rules, such that an alarm or an insight is triggered. For example, if medical device data specific to a first patient indicates that the heart rate of the patient is greater than 150 beats per minute, and if the rules engine includes a set of alarm rules indicating that an alarm should be output if the first patient's heart rate is greater than 150 beats per minute, then the medical device data satisfies that set of alarm rules. If no alarm or insight rules have been triggered, method 2700 loops back to 2702 and continues to receive medical device data and apply the alarm and/or insight rules to the received data.

If the received medical device data satisfies at least one set of alarm rules or one set of insight rules, method 2700 proceeds to 2708 to automatically generate a notification based on the satisfied rules. Generating the notification may include, as indicated at 2710, generating a notification that includes an alarm of a change in patient state. If a set of alarm rules is satisfied, an alarm may be generated. The alarm may include an indication of which alarm rules were satisfied, the patient the alarm is for, the user(s) who should receive the alarm, and/or the time the alarm was triggered. Further, generating the notification may include, as indicated at 2712, generating a notification that includes an insight into a change in patient state. If a set of insight rules is satisfied, an insight notification may be generated. The insight notification may include an indication of which insight rules were satisfied, the patient the insight is specific to, the user(s) who should receive the insight notification, and/or the time the insight was triggered. In some examples, the insight notification may include processed data, a prediction of future patient state, a determination of current patient state or procedure phase, or other non-alert result. In such examples, the result of the insight may be displayed as a tile on a single-patient GUI and/or multi-patient GUI during all conditions. An example of a predictive insight that may trigger a notification of a prediction of a future patient state is provided below with respect to FIG. 29.

At 2714, the notification is output for display. In some examples, the notification may be generated by the edge device and sent to the appropriate care provider device directly (e.g., via a hospital network communicatively coupling the edge device and the care provider device) or indirectly (e.g., via cloud-based service). When the care provider device receives the notification, the care provider device may display the notification as a tile in a multi-patient GUI and/or a single-patient GUI, as indicated at 2716. For example, as shown in FIG. 9, a brief notification of an alarm may be displayed in an alarm tile (e.g., tile 306) and a more detailed notification of the alarm may be displayed when requested by the user (e.g., as the alarm banner 904). In another example, when an insight is triggered (such as the hypoxia predictive insight described above with respect to FIGS. 22-25), a notification of the insight may be displayed in an insights tile (e.g., insights tile 302) and/or output from the insight (e.g., a risk score) may be displayed as a tile in a single-patient GUI (e.g., a hypoxia risk score may be displayed in the hypoxia score tile 2202 of FIG. 22).

In some examples, as indicated at 2718, the notification is pushed to the care provider device (e.g., via the cloud-based service), even when the supervisory application is in an unlaunched state on the care provider device. In such an example, when the supervisory application is not launched on the care provider device, the care provider device may output the notification for display on a notification page, a home page, and/or a sleep page of the care provider device.

At 2720, additional information may be output for display. The additional information that is output may be related to the triggered alarm or the triggered insight, and may be output in response to a user request or output automatically. The additional information that is output may include an action menu including selectable control buttons, as indicated at 2722. The action menu may be displayed when an alarm or insight tile of a multi-patient or single-patient GUI is selected, such as the acknowledge button 806 and snooze button 808 of FIG. 8 that are displayed in response to user selection of the insights tile 302. An action dictated by the selected control button may be performed when requested. For example, if the user selects the snooze button, the notification of the triggered alarm or insight may be output again after a predetermined amount of time, such as 10 minutes.

In some examples, the additional information may include trends of parameters that contributed to an insight risk score and/or a set of score trends of the parameters that contributed to a risk score, as indicated at 2723, when the insight is a predictive insight as described above. For example, user selection of an insights tile or a risk score tile may cause a set of parameter trends to be displayed, where the set of parameter trends includes trend lines showing change in parameter value over time for one or more patient monitoring parameters determined to have contributed to the predictive insight risk score, such as the set of trends 2302 of FIG. 23A. Further, in some examples, a set of score trends may be displayed, showing normalized trends of the contribution of each of one or more parameters determined to contribute to the risk score and/or a relative contribution of each parameter to a risk score, as shown in FIG. 25.

At 2724, the notification settings for a specific user (and hence the user's care provider device) may be adjusted when requested. For example, if a settings button is selected (e.g., button 906 of FIG. 9), an alarms setting page may be displayed where saved alarms may be turned on, turned off, or removed, and where new alarms may be added. In another example, via input to a displayed insight in a "my insights" view of an insights GUI of the supervisory application, an edit insight page may be displayed (e.g., as shown in FIG. 20) where saved insights may be turned on, turned off, edited, or deleted, and where new insights may be created. In a still further example, insights created by other users may be searched or browsed via a "discovery" view of the insights GUI (as shown in FIG. 17), and any selected insights from the discovery view may be saved to be applied for that user. Method 2700 then returns.

Figure 28:
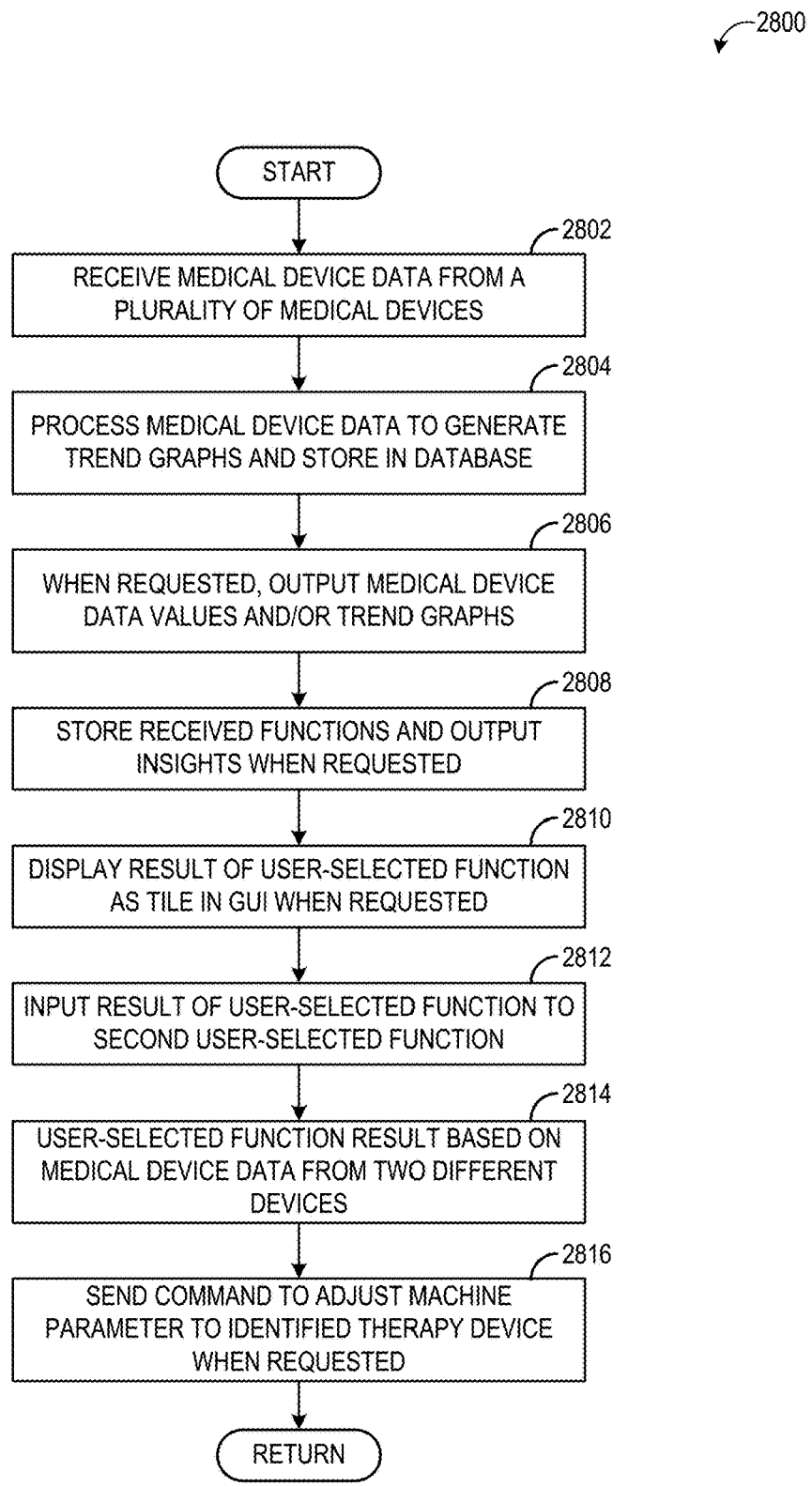
FIG. 28 is a flow chart illustrating an example method for a supervisory application.

FIG. 28 is a flow chart illustrating an example method 2800 for a supervisory application. Method 2800 may be implemented by an edge device connected to the care provider device (e.g., edge device 20), a cloud in communication with the edge device and/or care provider device (e.g., MDD processing system 12), a care provider device (such as care provider device 134), or any appropriate combination thereof.

At 2802, medical device data from a plurality of medical devices is received. The medical device data may be received from one or more medical devices, such as the medical devices 16 of FIG. 1A. The medical device data may be received by a data ingestion module of the edge device, for example, and in some examples may be processed by a stream processing module of the edge device, as explained above with respect to FIG. 1B. Additionally or alternatively, the medical device data may be sent to a cloud-based device, such as the MDD processing system 12 of FIG. 1A, where the medical device data may be ingested by an ingestion module (e.g., high speed ingestion module 22).

At 2804, the medical device data may be processed to generate trend graphs and the trend graphs are stored in a database. For example, each stream of medical device data may be stored, at least temporarily, as a trend graph (which may be a line graph, a series of bar graphs, or another suitable representation of data values over time) in a data storage location, such as data storage 104 of FIG. 1B and/or operation case storage 30 of FIG. 1A.

At 2806, medical device data values and/or trend graphs are output when requested. For example, when a supervisory application (such as supervisory application 44) is launched on a care provider device (such as care provider device 134), a single-patient GUI (e.g., single patient GUI 200 of FIG. 2) or a multi-patient GUI (e.g. multi-patient GUI 1100 of FIG. 11 or multi-patient GUI 1300 of FIG. 13) may be displayed on a display of the care provider device. When one of these GUIs is displayed, the supervisory application may stream real-time medical device data values to the care provider device, via a streaming server such as streaming server 114 of FIG. 1B. In another example, a trends GUI may be displayed on the display of the care provider device, and selected assembled/stored trend graphs may be output to the care provider device to be displayed as part of the trends GUI. In a further example, when the single-patient GUI is displayed on the display of the care provider device, user selection of a patient monitoring parameter tile may cause display of a trend graph for that patient monitoring parameter and/or additional trend graphs of related patient monitoring parameters, and the selected assembled/stored trend graphs may be output to the care provider device to be displayed as part of the single-patient GUI. In a still further example, when a predictive insight has been triggered and an insights tile or a risk score tile is selected by a user, a set of selected assembled/stored trend graphs may be output to the care provider device, in the form of the sets of trends shown in FIGS. 23A-23D and 24 or the set of normalized trends shown in FIG. 25.

At 2808, received functions are stored and selected stored functions are output when requested. The received functions may be received from the care provider device, for example in response to user-creation of a function (e.g., an insight) via an insights GUI (e.g., insights GUI 1700) displayed on the display of the care provider device. Functions may be created via other mechanisms, and may include models, algorithms, or other routines to process the medical device data from one or more medical devices and produce a result based on the medical device data. Functions may be received by other care provider devices at one or more medical facilities. The received functions may be stored at the edge device and/or on the MDD processing system. Further, when a user creates a function, that function may be shared with other users in response to a request from the user. Thus, if a request to share a function is received, that function may be output to a different storage location (e.g., the rules defining the insight may be sent from the edge device to the MDD processing system or other cloud-based service). In other examples, such as when all functions are stored on the cloud, the function may not be output to a different location when shared, but the privacy setting of the function may be changed to allow the function to be shared with other users. The predictive insights described herein are examples of functions that may be received and stored. Additional details about the predictive insights/functions are described below with respect to FIG. 29.

At 2810, the result of a user-selected function is displayed as a tile in a GUI, such as a single-patient GUI, when requested. For example, a user may select to apply a function for a specific patient or room, such as by selecting a function created by another user via the insights GUI 1700 or by selecting to apply a function created by the user, for example by generating a function via the new insights view 2100 and selecting to apply that function. The user-selected function may produce a transient result, such as a notification that is only triggered when a condition and a scope of the condition are met by the medical device data for the patient. As another example, the user-selected function may produce a persistent result that may generated under some or all of the duration of the patient monitoring for the patient, such as a determination of the anesthesia phase or an indication of a determined current patient state, such as a sepsis risk or a hypoxia risk. In the example of the function that produces a risk score indicating a likelihood that a patient will exhibit a particular condition in a subsequent time frame, such as sepsis risk result, the sepsis risk result may be on a scale of 1-10, classified as low, medium, or high, or another representation of the risk, and the representation of the risk may be determined and output at any time over the course of the patient monitoring. If the function produces a transient result, the result of the function may be displayed as a tile (e.g., as an insights tile) in a single-patient GUI specific to the patient or room and/or in a multi-patient GUI only in response to the rules of the function (e.g., the condition/scope) being met. If the function produces a persistent result, the result from the function may be displayed as a tile in the single-patient GUI for the patient in response to a user request to display the tile, and may only be removed from the GUI in response to a user request to remove the tile.

At 2812, the result of a user-selected function is input into a second user-selected function, when requested. As explained above, some functions may include the output of another function as an input, along with the medical device data. If a second user-selected function includes the result of a first user-selected function as an input, the result of the first user-selected function may be determined and then supplied to the second user-selected function. For example, a first function may produce current anesthesia phase as a result and a second function may include a notification being output as a result when heart rate is greater than a threshold during maintenance phase of anesthesia. The result of the first function may be used by the second function to determine the result of the second function along with the received medical device data (e.g., the anesthesia phase may be analyzed along with the heart rate as determined from a medical device monitoring a patient to determine if a notification should be output). As another example, a first function may produce sepsis risk as a result and a second function may include a notification being output as a result when heart rate is greater than a first threshold and when sepsis risk is greater than a second threshold. The result of the first function may be used by the second function to determine the result of the second function along with the received medical device data (e.g., the sepsis risk as determined by the first function may be analyzed along with the heart rate as determined from a medical device monitoring a patient to determine if a notification should be output).

At 2814, in some examples, the result of a user-selected function is based on medical device data from at least two different medical devices, and the respective patient monitoring values or trends from each of the two different medical devices may be displayed as respective tiles on a single-patient GUI, and in some examples, the result of the user-selected function is displayed as a separate tile on the single-patient GUI. For example, a function that produces a hypoxia risk value (e.g., on a scale of 0-1) may determine the hypoxia risk score based on, among other parameters, SpO2, FiO2, EtCO2, and blood pressure. SpO2 may be determined from first medical device data output by a first medical device (e.g., a pulse oximeter) and blood pressure may be determined from second medical device data output by a second medical device (e.g., a blood pressure monitor). The SpO2 may be displayed in a first patient monitoring parameter tile on a single-patient GUI, the blood pressure may be displayed in a second patient monitoring parameter tile on the single-patient GUI, and the hypoxia risk score may be displayed as a third tile on the single-patient GUI.

As another example, a function that produces a notification when a change in heart rate over a specified duration is above a threshold change and when body temperature is above threshold temperature may include as input into the function heart rate as determined from first medical device data output by a first medical device (e.g., a heart rate monitor) and body temperature as determined from second medical device data output by a second medical device (e.g., a temperature sensor). The heart rate may be displayed in a first patient monitoring parameter tile on a single-patient GUI, the body temperature may be displayed in a second patient monitoring parameter tile on the single-patient GUI, and the notification output as a result of the function may be displayed as a third tile on the single-patient GUI, at least when the specified conditions trigger the notification. In this way, user-selected functions may utilize medical device data, which may include medical device data from two or more devices in some examples, and may also use the results of other functions to provide insights into current or future patient state that may not be possible by monitoring the output of individual medical devices in isolation. For example, a heart rate monitor may be configured to output an alarm when heart rate is very high, such as greater than 150 beats per minute. While such an alarm may be useful, the alarm may miss earlier or more subtle signs that the patient may be undergoing duress. Thus, a function that combines a change in heart rate with body temperature may be able to provide an earlier potential warning of sepsis or other deterioration in patient state than by relying solely on heart rate reaching a predefined threshold. If the patient has a low resting heart rate, for example, the relative change in heart rate may be more informative than the absolute number of beats per minute, and by combining the change in heart rate with body temperature, the change in heart rate may be put into better context and thus provide different information to a care provider than if heart rate changed while body temperature remained stable.

At 2816, a command to adjust a machine parameter is sent to an identified therapy device if requested. For example, a determination may be made if a request to change a machine parameter has been received. As explained above, a user of the supervisory application (e.g., the supervising care provider interacting with the supervising application on a care provider device) may request a machine parameter or setting be adjusted via an adjustment box displayed as part of the single-patient GUI. The care provider device may send a request to the edge device to adjust the machine parameter. The therapy device may be identified based on the received request from the care provider device, which may specify which machine (e.g., therapy device) is to be adjusted and which parameter of the machine is to be adjusted (and by how much). Method 2800 then returns.

Figure 29:
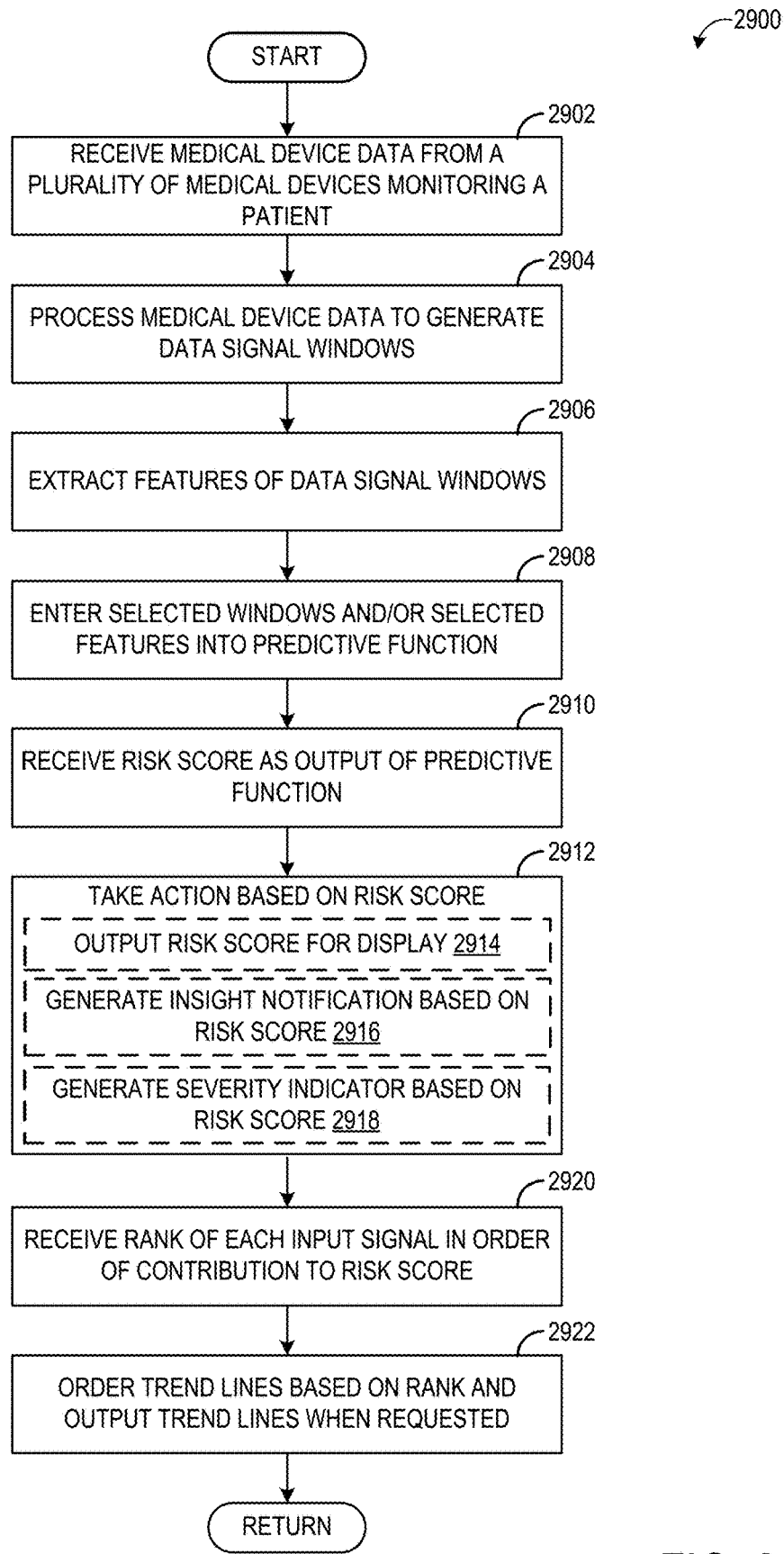
FIG. 29 is a flow chart illustrating an example method for generating a risk score a using predictive function via the supervisory application and taking one or more actions based on the risk score.

FIG. 29 is a flow chart illustrating an example method 2900 for generating a risk score via a predictive function of a supervisory application. Method 2900 may be implemented by an edge device connected to the care provider device (e.g., edge device 20), a cloud in communication with the edge device and/or care provider device (e.g., MDD processing system 12), a care provider device (such as care provider device 134), or any appropriate combination thereof.

At 2902, medical device data from a plurality of medical devices monitoring a patient is received. The medical device data may be received from one or more medical devices, such as the medical devices 16 of FIG. 1A. The medical device data may be received by a data ingestion module of the edge device, for example, and in some examples may be processed by a stream processing module of the edge device, as explained above with respect to FIG. 1B. Additionally or alternatively, the medical device data may be sent to a cloud-based device, such as the MDD processing system 12 of FIG. 1A, where the medical device data may be ingested by an ingestion module (e.g., high speed ingestion module 22).

Figure 30:
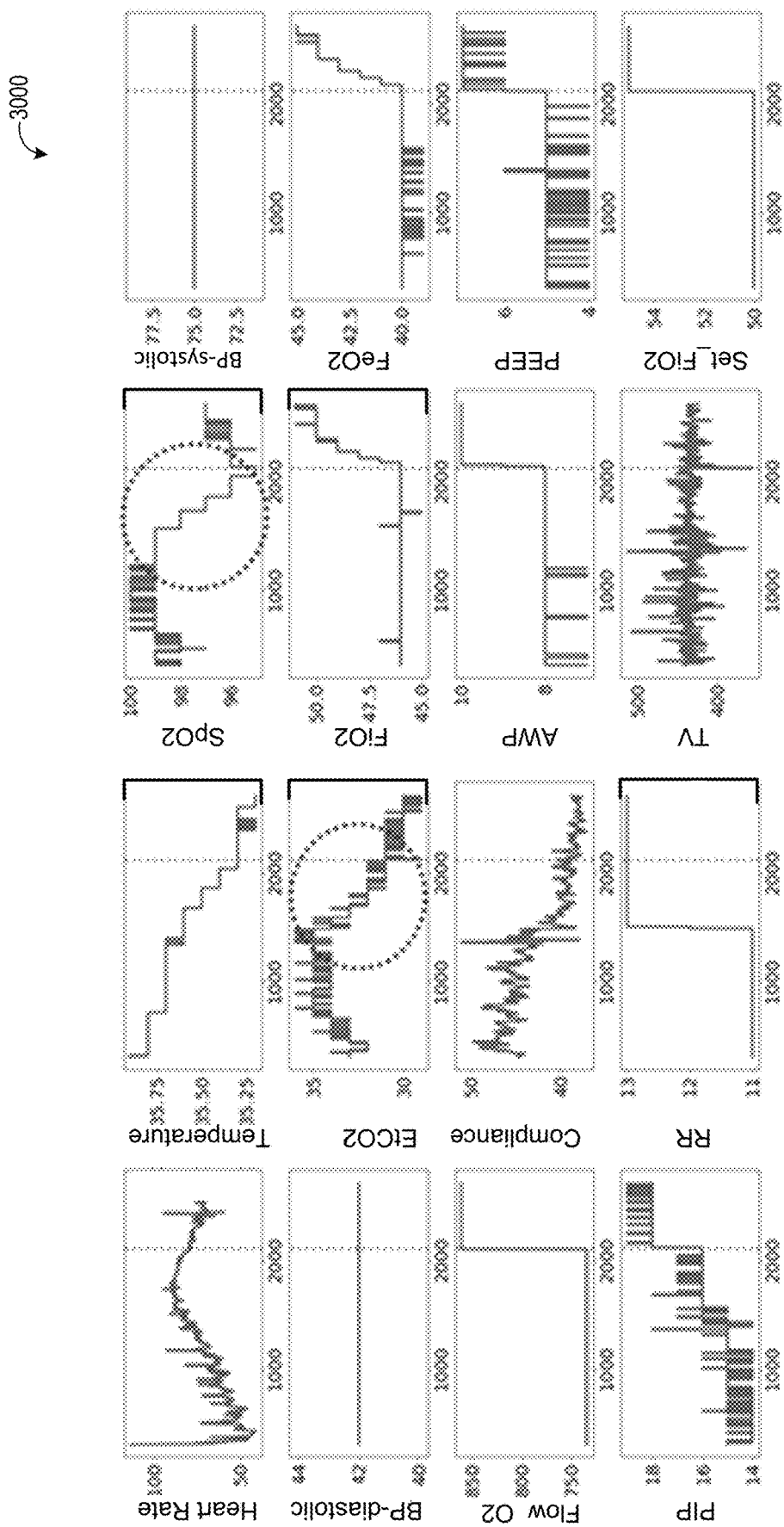
FIG. 30 illustrates a set of data signal windows that may be entered as input to a predictive function and/or used to train the predictive insight.

At 2904, the medical device data may be processed to generate a plurality of data signal windows for the patient. Each data signal window may be generated from the time series streams of medical device data described above with respect to FIGS. 1A and 1B. For example, a respective data signal from each medical device over a window of time (e.g., the prior 10 minutes, the prior 15 minutes, the prior hour, the entire duration of a current monitoring session for a patient) may be processed into a data signal window that includes values for that medical device data signal over the window of time. The data signal may be a plot/graph (e.g., as shown in FIG. 30 and explained in more detail below), a series of values, or another suitable format. In some examples, the number of data signal windows that are generated corresponds to the number of patient monitoring parameters that are currently being monitored by the medical devices for that patient (e.g., if the patient is being monitored for 15 different parameters, 15 different data signal windows may be generated, each corresponding to a respective patient monitoring parameter), such that a data signal window is generated for each patient monitoring parameter that is received for the patient. In other examples, only a subset of the medical device data signals may be processed to generate the plurality of data signal windows, depending on the predictive function(s) that are currently being executed. For example, when the predictive function is a hypoxia predictive function, a first subset of the medical device data signals may be processed into the data signal windows described herein, while when the predictive function is a sepsis predictive function, a second, different subset of the medical device data signals may be processed into the data signal windows described herein.

At 2906, method 2900 optionally includes extracting features of the plurality of data signal windows. The extracted features may include, for each data signal window, a mean value of the data signal over the window, minimum and maximum values of the data signal over the window, and skewness, kurtosis, etc., of the data signal over the window. In some examples, the extracted features may include entropy, coefficients of Fourier/wavelet transforms, absolute energy, etc., of the data signal over the window.

At 2908, selected data signal windows and/or features of the data signal windows are entered into a predictive function. The predictive function may include a deep learning or other machine learning model, at least in some examples. The predictive function may generate a risk score based on the input data signal windows and/or features of the data signal windows, where the risk score indicates a relative likelihood that the patient will exhibit a condition specified by the predictive function. The predictive function may be a hypoxia function that predicts a likelihood of the patient exhibiting hypoxia, a hyperoxia function that predicts a likelihood of the patient exhibiting hyperoxia, a hypotension function that predicts a likelihood of the patient exhibiting hypotension, etc. The risk score that is output by the predictive function may indicate a relatively likelihood of the patient exhibiting the condition within a predetermined period of time, such as in the next 5 minutes, the next 10 minutes, or the next 15 minutes. Each predictive function may output a different risk score indicative of the likelihood of the patient exhibiting a different condition within a period of time. In other examples, one predictive function may output two or more different risk scores each indicative of a likelihood of a patient exhibiting a different condition within a period of time.

Different predictive functions may utilize different input data signals, as explained above. Thus, the selected data signal windows and/or extracted features that are entered as input may depend on the predictive function that is being applied. FIG. 30 shows an example set of input data signal windows 3000 of a patient that may be input into a hypoxia predictive function. The set of input data signal windows 3000 shown in FIG. 30 includes, for each data signal window, that data signal plotted as a function of time. Each window of time is the same (e.g., 2500 seconds) in the example shown, although in some examples, different windows of time for different data signals may be generated.

The input signals shown in FIG. 30 include heart rate, diastolic blood pressure, oxygen flow, and peak inspiratory pressure (PIP) in the first column of data signals; temperature, end tidal CO2 (EtCO2), lung compliance, and respiration rate in the second column of data signals; SpO2, fraction of inspired oxygen (FiO2), airway pressure (AWP), and tidal volume (TV) in the third column of data signals; and systolic blood pressure, fraction of expired oxygen (FeO2), and positive end-expiratory pressure (PEEP) in the fourth column of input signals.

Also shown in FIG. 30 is a set fraction of inspired oxygen (Set FiO2) which may indicate when the oxygen concentration on the ventilator connected to the patient was increased. The set FiO2 may represent when hypoxia in the patient was detected and may serve as the ground truth for training the hypoxia predictive function. During training of the hypoxia predictive function, training data sets may be fed to the untrained, unvalidated model. Each training data set may include data signal windows similar to those shown in FIG. 30 along with a corresponding ground truth (e.g., the set FiO2). In the example of FIG. 30 where a hypoxia score is output, the ground truths are generated by looking at changes in setting of FiO2, where a positive change indicates a hypoxia event which the model is then trained to predict. Thus, the setting of FiO2 is used to annotate data on presence or absence of hypoxia events (1 or 0) which is then used for model training. The model is used to solve a classification problem and therefore predicts a likelihood of hypoxia events. This likelihood is converted to a severity score which when exceeds a threshold indicates a high probability of hypoxia event. Each training dataset may be obtained from and is specific to a different (reference) patient. While only dynamic patient monitoring parameter data signals are shown in FIG. 30, in some examples static information may also be input to a predictive function, such as patient demographic information (e.g., age, weight, height, geographic location), prior diagnosed patient conditions (e.g., prior diagnoses of heart issues or lung issues), etc.

Returning to FIG. 29, at 2910, a risk score is received as output from the predictive function. The risk score may convey a relative risk of the patient exhibiting the condition of the predictive function (e.g., hypoxia), as explained above. The risk score may be a numerical value from a suitable range, such as a value in a range of −1.50-+1.50, a value in a range of 1-10, etc. At 2912, one or more actions are taken based on the risk score. As indicated at 2914, the one or more actions may include outputting the risk score for display on a display device (e.g., display 202). For example, the risk score may be output for display on a care provider device (such as care provider device 134) as part of a predictive or risk score tile of a single-patient GUI (e.g., hypoxia score tile 2202 of single patient GUI 200 of FIG. 22), as part of a trends view or score view on the single-patient GUI (e.g., as shown in FIGS. 23A-25), and/or in response to user-selection of an insights tile of the single-patient GUI. As indicated at 2916, the one or more actions may include generating a notification based on the risk score. The notification that is generated may be a notification that an insight has been triggered, which may be displayed as part of an insights tile, such as insights tile 302 of single-patient GUI 200.

Further, as indicated at 2918, the one or more actions may include generating or adjusting a severity indicator based on the risk score, and outputting the severity indicator for display on the care provider device (e.g., as part of the single-patient GUI, such as the severity indicator 2206 shown in FIG. 22 and/or as part of a multi-patient GUI). As explained above with respect to FIG. 22, the severity indicator may indicate, via color coding or another suitable coding (e.g., pattern or shape), a relative severity of the patient condition is determined from the risk score. For example, when the risk score is a value selected from a range of −1.5 to +1.5, a risk score of 0 or below may indicate low risk, a risk score greater than 0 but less than 1 may indicate intermediate risk, and a risk score greater than 1 may indicate high risk. The color of the severity indicator may be adjusted based on the risk score, e.g., if the risk score increases from 0.9 to 1.1, the color of the severity indicator may be adjusted from yellow to red.

Figure 31:
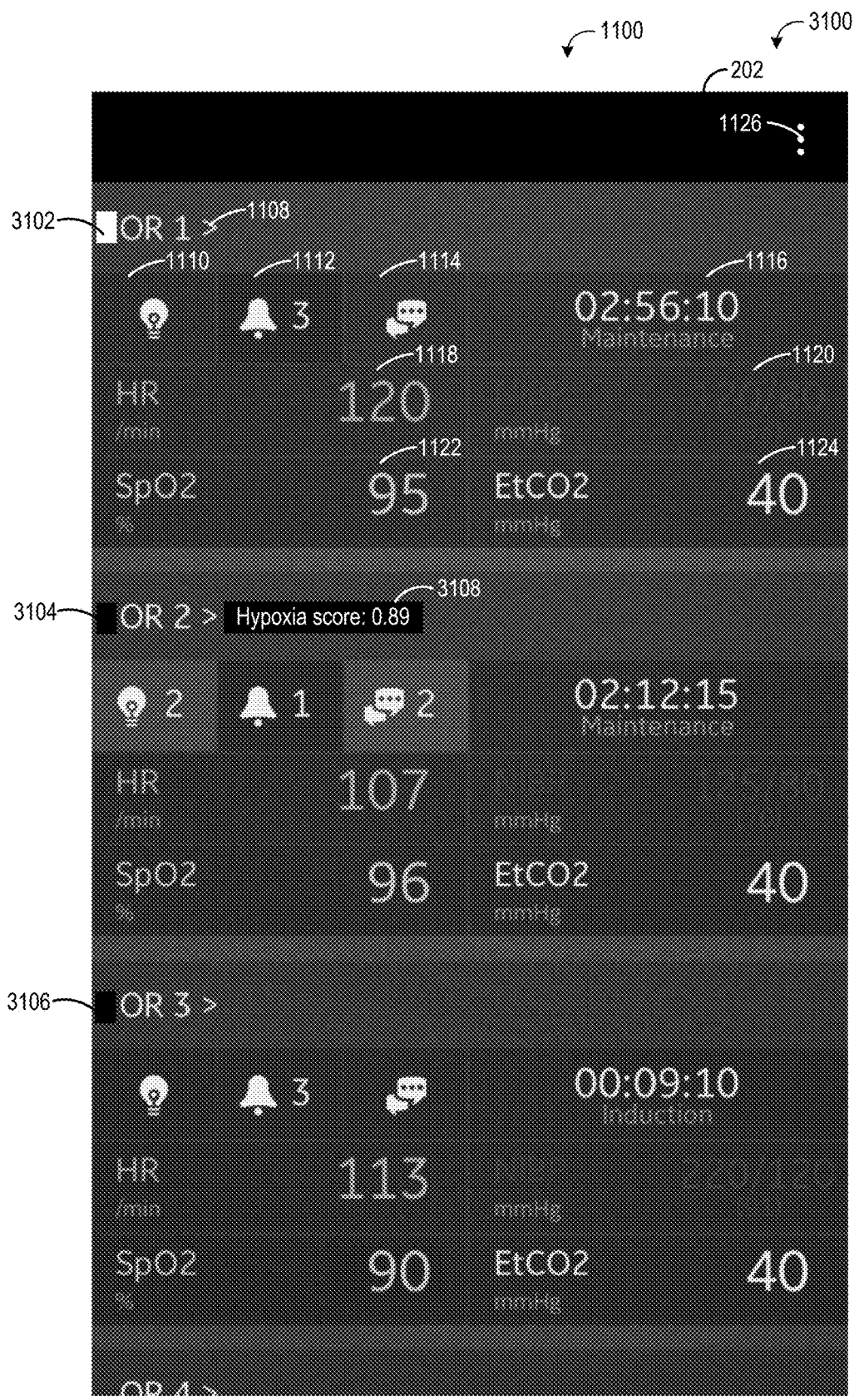
FIG. 31 shows the display device displaying the multi-patient graphical user interface generated via the supervisory application along with a plurality of severity indicators.

FIG. 31 shows an example insight view 3100 of multi-patient GUI 1100. Insight view 3100 may be similar to the view of multi-patient GUI 1100 presented in FIG. 11, and thus includes a plurality of patient banners, each specific to a different patient/operating room and including a forward button, an insights tile, an alarm tile, a message tile, and a procedure timing tile, such as procedure timing tile, as well as a limited view of patient monitoring tiles. In the insights view 3100, severity indicators are displayed next to each patient/operating room name in the respective patient banner. For example, a first severity indicator 3102 is displayed next to OR1, a second severity indicator 3104 is displayed next to OR2, and a third severity indicator 3106 is displayed next to OR3. The color of each severity indicator may indicate the relative severity of each patient condition. For example, the first severity indicator 3102 is yellow, indicating intermediate severity, the second severity indicator 3104 is red indicating high severity, and the third severity indicator 3106 is green, indicating low severity. In some examples, risk score tiles for one or more patients may be shown, such as risk score tile 3108. The risk score shown in a risk score tile may an individual risk score for one predictive insight (e.g., the hypoxia score), or the risk score shown in in the risk score tile may be an overall score that represents two or more risk scores from two or more predictive insights. The overall score may be a sum of the two or more risk scores or the overall score may be the highest of the two or more risk scores. In this way, the severity of each predicted patient condition may be quickly assessed and compared to one another, so that the care provider may decide which patient has the most urgent care need. While not shown, a multi-patient GUI similar to multi-patient GUI 1300 may also display severity indicators in the manner described above.

Returning to FIG. 29, at 2920, a rank of each data signal that is input to the predictive function is received, where the rank is in order of the input signals' contribution to the risk score output by the predictive function. For example, the predictive function may include an interpretability feature that assigns each input signal (and/or each feature of each input signal) an importance value for that iteration of the predictive function. The interpretability feature assesses the effect of the input signals/features on the output using a game theory approach. The interpretability feature may utilize an approach similar to Shapley values from co-operative game theory through computing marginal contribution from each input signal towards a prediction. This approach utilizes a mathematical framework through averaging over marginal contributions from every possible combination of input signals. The input signals may be ranked in decreasing order of importance. Referring again to FIG. 30, two input data signals have been identified by the interpretability feature as contributing significantly to the hypoxia score that would be generated from the input signals shown in FIG. 30. The first input signal identified by the interpretability feature is EtCO2 and the second input signal identified by the interpretability feature is SpO2. The circles in FIG. 30 illustrate the features of each input signal that contributed to/resulted in a high positive risk score, e.g., decreasing EtCO2 and decreasing SpO2. It should be noted that at least in some examples, a risk score may be output that indicates a relatively high risk for a condition (e.g., hypoxia) before any device- or parameter-specific alarms are triggered. For example, a high risk for hypoxia may be determined based on the risk score, before an SpO2 or EtCO2 alarm is triggered. Further, the input signals/features contributing to the risk score may change for different patients or different iterations of the predictive function.

At 2922, a plurality of trend lines may be ordered based on the rank and the trend lines may be output when requested. The trend lines may be plots of values for each medical device data signal for the patient over time, with each trend line corresponding to a data signal that is input into the predictive function. For example, the predictive function may include data signal windows for SpO2, EtCO2, FiO2, and diastolic blood pressure as inputs, and the trend lines may include trend lines of SpO2, EtCO2, FiO2, and diastolic blood pressure. In some examples, the trend lines may be the same as the data signals that are input to the predictive function (e.g., the same values and the same window of time). In other examples, the trend lines may include values over a different window of time (e.g., a shorter window of time, a longer window of time, and/or a different window of time, such as a more recent window of time). In some examples, the window of time over which the trend lines are plotted may be based on when the features contributing to the risk score occurred, so that each feature may be visualized together. The trend lines may be ordered so that the trend lines corresponding to input signals resulting in high positive scores are on the top and the trend lines corresponding to input signals resulting in low negative scores are at the bottom. The trend lines may be displayed in the order described above when the user requests to the view the trend lines contributing to the risk score (e.g., as shown in FIGS. 23A-23D and 24). Method 2900 then returns.

Thus, the systems and methods described herein provide for risk prediction of a patient condition deteriorating using preoperative patient data and real-time multivariate time series data during a medical procedure such as surgery. The supervisory application described herein may include or facilitate application of a predictive insight/predictive function that provides clinical decision support to an anesthesiologist supervising single or multiple surgeries in a hospital. The predictive insights described herein may identify the type of distress and may provide explainability with signals contributing to the reported severity/risk score.

A supervising anesthesiologist may oversee multiple operation rooms (ORs) simultaneously to reduce costs for healthcare providers. Typically, a supervising anesthesiologist is located in an OR during induction and emergence phases of anesthesia, and then the anesthesiologist may leave the patient to the attending non-physician/trained nurse who operates the anesthesia machine during the maintenance phase. If there is an emergency, the anesthesiologist may be called back in to the OR. However, if there are multiple emergencies simultaneously, or when multiple emergences need to happen at the same time, care provider resources may be stretched thin, and currently these multiple emergency or multiple emergence scenarios are not well-managed. Additionally, simply knowing what patient the anesthesiologist should pay more attention to in general is not known.

Thus, the predictive functions described herein may utilize preoperative data to determine overall patient risk, combined with real-time data regarding negative trending to proactively indicate which operating room/patient could be the most important for the anesthesiologist to be in or to be close by at any given time. The predictive functions may use data from multiple sources: patient medical history, precondition, etc., and real-time patient data during the medical procedure from patient monitors, anesthesia machine (numerics/waveforms on patient vitals and drugs administered) to predict if in the next 5 or 10 or 15 minutes the patient condition is going to deteriorate or not. If the predictive function determines that the patient condition is going to deteriorate, the predictive function may notify the anesthesiologist of the type of distress and a predicted severity score/level of the distress/deterioration in patient condition. The predictive functions may also identify the specific factors/signals which contributed to the severity/risk score based on which the predictive function arrived at the decision. The severity/risk score calculated by the predictive function for these expected patient conditions (hypoxia, hypotension, etc.) would be available to the clinician to access and visualize just like any other patient vital. The predictive function for each of the adverse events may be built through understanding of the factors which specifically affect the physiology contributing to and indicative of a deteriorating condition.

As patient data is accumulated over time during the medical procedure, basic statistical features may be extracted from the time series data, such as mean, min/max, skewness, kurtosis, etc., and also more advanced dynamics features such as entropy, coefficients of Fourier/wavelet transforms, absolute energy, autocorrelation coefficients among others. During the offline training of the predictive functions, it is known when an adverse event happened and these extracted features and their evolution during the medical procedure are mapped to the presence or absence of these events. These mappings or models also enable the filtration of these features based on their relative importance and only the features contributing significantly are retained for building the final model for deployment. Once a prediction is made by the model, there may be a post-analysis of output that traces the features that contributed to the model output, e.g., it segregates the features which contributed to making the predicted severity score higher from the ones which were driving the score lower. This allows the clinicians to understand how the model arrived at those results which they can trust more and can help them take an informed decision.

In the event of the same patient experiencing multiple adverse events, the severity scores for each of these multiple events may be normalized and compared to prioritize for the care provider/user. These predicted risk/severity scores may be used to prioritize patient condition in multiple ORs in a hospital to allow the anesthesiologist focus their attention where it is needed most. Again, in the event where multiple patients are going through these events, the severity scores from each of these events from different patients may be normalized and compared to prioritize the risk for the care provider. For example, the normalized adversity scores from multiple models (for multiple events like hypoxia, hypotension, etc.) for a single patient can be summed up or the maximum of all these can be used as a single risk score for the patient. This single score for multiple patients can then be ranked in order of decreasing severity. Also, there can be simple color coding for the patient condition (green/yellow/red) based on a range of threshold values of the total score. Further, the predictive insights/models may be continuously trained and improved when deployed at a particular site. The annotations provided by the clinicians in the form of notes, event markings on time series data, and/or use of heuristics for auto-annotation of adverse events may be used to incrementally train the model through continuous learning to improve prediction accuracy for specific type of patients and surgeries seen by a particular hospital. An aspect of continuous learning that will be used is based on context-based information retrieval, where records of same or similar patients from past are retrieved to reinforce and improve model predictions. The model accuracy and the score prediction with interpretability helps the anesthesiologist take a call to intervene or not in the hope that they do not miss any adverse event and at the same time do not experience alarm fatigue.

A technical effect of a supervisory application that displays medical device data aggregated from multiple medical devices on a single graphical user interface in a user-configurable manner is that a user, such as a care provider, may view desired patient monitoring parameters for a patient the user is monitoring on a limited display area, with as much data as possible displayed on the limited display area. The displaying of the medical device data from multiple medical devices on the single graphical user interface in a user-configurable manner also allows the user to monitor patient status from any location and provide instructions via the supervisory application. The user may view new medical device data as new medical devices are coupled to the patient. The user may define functions and/or access functions defined by other users via the supervisory application that may transform and/or analyze the medical device data (from multiple medical devices) to provide results of patient status not detectable from single values of the medical device data. The functions may be created and accessed at any time, which may allow new functions to be defined and applied as new devices are added. A technical effect of displaying one or more risk scores determined via a predictive insight on a GUI of the supervisory application is that prediction of future patient states may be presented to a user of the supervisory application, which may assist the user in prioritizing patients needing care. A technical effect of displaying additional information related to each determined risk score, when requested, is that the user of the supervisory application may assess the accuracy of each risk score, which may further assist in patient care prioritization. Via the supervisory application, the user may locate and view desired data without having to navigate through multiple menus, which may increase user efficiency in interacting with a computing device.

An embodiment relates to a system including a display; and a computing device operably coupled to the display and storing instructions executable to: output, to the display, a graphical user interface (GUI) that includes real-time medical device data determined from output of one or more medical devices each monitoring a patient, and where at least some of the real-time medical device data displayed via the GUI is displayed as a plurality of patient monitoring parameter tiles, the GUI further including a predictive tile including a risk score indicative of a relative likelihood that the patient will exhibit a specified condition within a predetermined period of time; and responsive to a user input, display, on the GUI, a set of trend lines each showing values for a respective patient monitoring parameter over a time range, each trend line of the set of trend lines selected based on a contribution of each respective patient monitoring parameter to the risk score. In a first example of the system, each patient monitoring parameter tile shows a most-recently determined value for that patient monitoring parameter, and wherein the values for each respective patient monitoring parameter for the set of trend lines are determined from the output of the one or more medical devices. In a second example of the system, which optionally includes the first example, the user input comprises selection of the predictive tile. In a fourth example of the system, which optionally includes one or more or each of the first through third examples, the user input is a first user input, and wherein the instructions are executable to, responsive to a second user input, display, on the GUI, the set of trend lines and an additional set of trend lines, each trend line of the additional set of trend lines showing values for a respective patient monitoring parameter over the time range, where the patient monitoring parameters represented in the set of trend lines contribute more to the risk score than the patient monitoring parameters represented in the additional set of trend lines. In a third example of the system, which optionally includes one or both of the first and second examples, the instructions are executable to display, on the GUI, a severity indicator that has a color, shape, and/or pattern selected based on the risk score. In a fifth example of the system, which optionally includes one or more or each of the first through fourth examples, the GUI is a single-patient GUI and the user input is a first user input, and wherein the instructions are executable to, responsive to a second user input, display a multi-patient GUI including real-time medical device data determined from output of a plurality of medical devices monitoring a plurality of patients, the plurality of patients including the patient and one or more additional patients. In a sixth example of the system, which optionally includes one or more or each of the first through fifth examples, the instructions are executable to display, on the multi-patient GUI, a first severity indicator for the patient, the first severity indicator having a color, a shape, and/or a pattern selected based on the risk score, and a respective severity indicator for each of the one or more additional patients, each respective severity indicator having a color, a shape, and/or a pattern selected based on a corresponding risk score for that patient. In a seventh example of the system, which optionally includes one or more or each of the first through sixth examples, the time range is selected based on a respective timing of each of one or more features of each respective patient monitoring parameter determined to have contributed to the risk score.

An embodiment relates to a system including a computing device storing instructions executable to: receive real-time medical device data determined from output from a plurality of medical devices monitoring a patient; determine a risk score for the patient based on the real-time medical device data over a first window of time, the risk score indicating a relative likelihood that the patient will exhibit a given condition within a second window of time; and responsive to the risk score being greater than a threshold, output a notification for display on a display. In a first example of the system, the real-time medical device data is processed to generate a plurality of input signals, each input signal including values for a respective patient monitoring parameter over the first window of time. In a second example of the system, which optionally includes the first example, the instructions are executable to input the plurality of input signals to a predictive function, the predictive function trained to generate the risk score from the plurality of input signals. In a third example of the system, which optionally includes one or both of the first and second examples, the predictive function is further configured to rank each input signal in order of contribution to the risk score. In a fourth example of the system, which optionally includes one or more or each of the first through third examples, the instructions are further executable to, responsive to a user input, output a set of trend lines for display on the display, each trend line of the set of trend lines including values for a respective patient monitoring parameter over the first window of time, the set of trend lines selected based on the rank of each input signal. In a fifth example of the system, which optionally includes one or more or each of the first through fourth examples, the instructions are further executable to, responsive to a user input, output a set of trend lines for display on the display, each trend line of the set of trend lines including values for a respective patient monitoring parameter over a selected window of time, the set of trend lines selected based on the rank of each input signal, the selected window of time determined based on a timing of one or more features of one or more input signals determined to have contributed to the risk score.

An embodiment relates to a method including outputting, to a display, a multi-patient graphical user interface (GUI) that includes a respective severity indicator for each patient of a plurality of patients, each severity indicator representing a relative severity of a condition for a respective patient, the relative severity determined based on one or more risk scores determined for each patient of the plurality of patients; responsive to a user input selecting a first patient of the plurality of patients, outputting, to the display, a single-patient GUI that includes real-time medical device data determined from output of one or more medical devices each monitoring the first patient, and where at least some of the real-time medical device data displayed via the single-patient GUI is displayed as a plurality of patient monitoring parameter tiles, each patient monitoring parameter tile showing a most-recently determined value for that patient monitoring parameter, and the single-patient GUI further includes a risk score tile including a first risk score determined for the first patient; and responsive to a user input selecting the risk score tile, outputting, to the display, additional information related to the determination of the first risk score for the first patient. In a first example of the method, outputting the additional information comprises outputting a set of trend lines, each trend line of the set of trend lines including values for a respective patient monitoring parameter of the patient over a window of time, the set of trend lines selected based on a contribution of each respective patient monitoring parameter to the first risk score. In a second example of the method, which optionally includes the first example, the window of time is selected based on a respective timing of each of one or more features of each respective patient monitoring parameter determined to have contributed to the first risk score. In a third example of the method, which optionally includes one or both of the first and second examples, the method further includes, responsive to a user input selecting a second patient of the plurality of patients, outputting, to the display, a second single-patient GUI that includes real-time medical device data determined from output of one or more medical devices each monitoring the second patient, the second single-patient GUI further including a second risk score tile including a second risk score determined for the second patient. In a fourth example of the method, which optionally includes one or more or each of the first through third examples, the method further includes, responsive to a user input selecting the second risk score tile, outputting, to the display, additional information related to the determination of the second risk score for the second patient, the additional information related to the determination of the second risk score for the second patient different than the additional information related to the determination of the first risk score for the first patient. In a fifth example of the method, which optionally includes one or more or each of the first through fourth examples, the first risk score indicates a first relative likelihood that the first patient will exhibit a given condition within a window of time and the second risk score indicates a second relative likelihood that the second patient will exhibit the given condition within the window of time.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
a display; and
a computing device operably coupled to the display and storing instructions executable to:
output, to the display, a graphical user interface (GUI) that includes real-time medical device data determined from output of one or more medical devices each monitoring a patient, and where at least some of the real-time medical device data displayed via the GUI is displayed as a plurality of patient monitoring parameter tiles, the GUI further including a predictive tile including a risk score indicative of a relative likelihood that the patient will exhibit a specified condition within a predetermined period of time, where a selected set of patient monitoring parameters of the real-time medical device data is input to a predictive function to determine the risk score;

responsive to a user input, display, on the GUI, one or more trend lines each showing values for a respective patient monitoring parameter of the selected set of patient monitoring parameters over a time range, each of the one or more respective patient monitoring parameters of the selected set of patient monitoring parameters being determined to have contributed positively to the risk score, where one or more remaining patient monitoring parameters of the selected set of patient monitoring parameters determined to not be indicative of the specified condition are excluded from the one or more trend lines being displayed, wherein the time range is selected based on a respective timing of each of one or more features of each respective patient monitoring parameter determined to have contributed positively to the risk score.

2. The system of claim 1, wherein each patient monitoring parameter tile shows a most-recently determined value for that patient monitoring parameter, and wherein the values for each respective patient monitoring parameter for the one or more trend lines are determined from the output of the one or more medical devices.

3. The system of claim 1, wherein the user input comprises selection of the predictive tile, and wherein only two patient monitoring parameters of the selected set of patient monitoring parameters are determined to have contributed positively to the risk score, and wherein the one or more trend lines that are displayed on the GUI include only two trend lines, the two trend lines showing values for the two patient monitoring parameters over the time range.

4. The system of claim 1, wherein the user input is a first user input, and wherein the instructions are executable to, responsive to a second user input, display, on the GUI, the one or more trend lines and an additional set of trend lines, each trend line of the additional set of trend lines showing values for a respective patient monitoring parameter of the selected set of patient monitoring parameters over the time range, where the patient monitoring parameters represented in the one or more trend lines contribute more to the risk score than the patient monitoring parameters represented in the additional set of trend lines.

5. The system of claim 1, wherein the instructions are executable to display, on the GUI, a severity indicator that has a color, shape, and/or pattern selected based on the risk score.

6. The system of claim 1, wherein the GUI is a single-patient GUI and the user input is a first user input, and wherein the instructions are executable to, responsive to a second user input, display a multi-patient GUI including real-time medical device data determined from output of a plurality of medical devices monitoring a plurality of patients, the plurality of patients including the patient and one or more additional patients.

7. The system of claim 6, wherein the instructions are executable to display, on the multi-patient GUI, a first severity indicator for the patient, the first severity indicator having a color, a shape, and/or a pattern selected based on the risk score, and a respective severity indicator for each of the one or more additional patients, each respective severity indicator having a color, a shape, and/or a pattern selected based on a corresponding risk score for that patient.

8. The system of claim 1, wherein the time range is selected based on a respective timing of each of one or more features of each respective patient monitoring parameter determined to have contributed to the risk score.

9. A system comprising:
a computing device storing instructions executable to:
receive real-time medical device data determined from output from a plurality of medical devices monitoring a patient;
determine a risk score for the patient based on the real-time medical device data over a first window of time, the risk score indicating a relative likelihood that the patient will exhibit a given condition within a second window of time, wherein the real-time medical device data is processed to generate a plurality of input signals, each input signal including multiple time series values for a respective patient monitoring parameter over the first window of time, and wherein the plurality of input signals are processed to extract one or more features over the first window of time that are input to a predictive function configured to output the risk score, the predictive function configured to rank each input signal in order of contribution to the risk score;
responsive to the risk score being greater than a threshold, output a notification for display on a display; and
responsive to a user input, output a set of trend lines for display on the display, each trend line of the set of trend lines including values for a respective patient monitoring parameter over a selected window of time, the set of trend lines ordered according to the rank of each input signal,
wherein the selected window of time is determined based on a timing of one or more features of one or more input signals determined to have contributed positively to the risk score.

10. The system of claim 9, wherein the one or more features include one or more of a mean value, a minimum value, and a maximum value of each input signal.

11. The system of claim 9, wherein the one or more features include one or more of skewness, kurtosis, entropy, transform coefficients, and absolute energy of each input signal.

12. The system of claim 9, wherein the selected window of time is determined based on a timing of one or more features of one or more input signals determined to have contributed to the risk score.

13. A method, comprising:
outputting, to a display, a multi-patient graphical user interface (GUI) that includes a respective severity indicator for each patient of a plurality of patients, each severity indicator representing a relative severity of a condition for a respective patient, the relative severity determined based on one or more risk scores determined for each patient of the plurality of patients;
responsive to a user input selecting a first patient of the plurality of patients, outputting, to the display, a single-patient GUI that includes real-time medical device data determined from output of one or more medical devices each monitoring the first patient, and where at least some of the real-time medical device data displayed via the single-patient GUI is displayed as a plurality of patient monitoring parameter tiles, each patient monitoring parameter tile showing a most-recently determined value for that patient monitoring parameter, and the single-patient GUI further includes a risk score tile including a first risk score determined for the first patient determined based on a plurality of patient monitoring parameters; and
responsive to a user input selecting the risk score tile, outputting, to the display, additional information related to the determination of the first risk score for the first patient, including outputting a set of trend lines, each trend line of the set of trend lines including values for a respective patient monitoring parameter of the patient over a window of time, the set of trend lines selected based on a contribution of each respective patient monitoring parameter to the first risk score such that patient monitoring parameters determined not to have contributed positively to the first risk score are excluded and only patient monitoring parameters determined to have contributed positively to the first risk score are included in the set of trend lines, wherein the window of time is selected based on a respective timing of each of one or more features of each respective patient monitoring parameter determined to have contributed to the first risk score, wherein the selected window of time is determined based on a timing of one or more features of one or more input signals determined to have contributed positively to the risk score.

14. The method of claim 13, further comprising, responsive to a user input selecting a second patient of the plurality of patients, outputting, to the display, a second single-patient GUI that includes real-time medical device data determined from output of one or more medical devices each monitoring the second patient, the second single-patient GUI further including a second risk score tile including a second risk score determined for the second patient.

15. The method of claim 14, further comprising responsive to a user input selecting the second risk score tile, outputting, to the display, additional information related to the determination of the second risk score for the second patient, the additional information related to the determination of the second risk score for the second patient different than the additional information related to the determination of the first risk score for the first patient.

16. The method of claim 15, wherein the first risk score indicates a first relative likelihood that the first patient will exhibit a given condition within a window of time and the second risk score indicates a second relative likelihood that the second patient will exhibit the given condition within the window of time.

* * * * *